(12) United States Patent
Balmayor et al.

(10) Patent No.: US 12,263,229 B2
(45) Date of Patent: *Apr. 1, 2025

(54) INDUCTION OF OSTEOGENESIS BY DELIVERING BMP ENCODING RNA

(71) Applicant: ethris GmbH, Planegg (DE)

(72) Inventors: Elizabeth Balmayor, Ried (DE); Carsten Rudolph, Krailling (DE); Christian Plank, Wessling (DE)

(73) Assignee: ethris GmbH, Planegg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/525,701

(22) PCT Filed: Nov. 10, 2015

(86) PCT No.: PCT/EP2015/076238
§ 371 (c)(1),
(2) Date: May 10, 2017

(87) PCT Pub. No.: WO2016/075154
PCT Pub. Date: May 19, 2016

(65) Prior Publication Data
US 2018/0214572 A1    Aug. 2, 2018

(30) Foreign Application Priority Data

Nov. 10, 2014  (EP) .................................... 14192539

(51) Int. Cl.
*A61K 47/00*        (2006.01)
*A61K 9/1271*       (2025.01)
*A61K 31/7105*      (2006.01)
*A61K 35/28*        (2015.01)
*A61K 35/33*        (2015.01)
*A61K 48/00*        (2006.01)
*A61P 19/08*        (2006.01)

(52) U.S. Cl.
CPC .......... *A61K 48/005* (2013.01); *A61K 9/1271* (2013.01); *A61K 35/28* (2013.01); *A61K 35/33* (2013.01); *A61P 19/08* (2018.01)

(58) Field of Classification Search
None
See application file for complete search history.

(56) References Cited

U.S. PATENT DOCUMENTS

| | | | |
|---|---|---|---|
| 8,450,298 B2 | 5/2013 | Mahon et al. | |
| 2012/0021042 A1 | 1/2012 | Panzner | |
| 2012/0195936 A1 | 8/2012 | Rudolph et al. | |
| 2012/0301512 A1 | 11/2012 | Xu et al. | |
| 2017/0021036 A1 | 1/2017 | Dohmen et al. | |

FOREIGN PATENT DOCUMENTS

| | | | |
|---|---|---|---|
| CN | 102695525 A | 9/2012 | |
| JP | 2004528101 A | 9/2004 | |
| WO | WO 2000/009086 | 2/2000 | |
| WO | WO 00/27795 | 5/2000 | |
| WO | WO 2003/029429 A2 | 4/2003 | |
| WO | WO 2006/066001 A2 | 6/2006 | |
| WO | WO 2006/072623 A1 | 7/2006 | |
| WO | WO 2010/053572 | 5/2010 | |
| WO | WO 2010/065660 A2 | 6/2010 | |
| WO | WO 2011/012316 A2 | 2/2011 | |
| WO | WO 2011/154331 | 12/2011 | |
| WO | WO 13/090648 | * 6/2013 | |
| WO | WO2013/090648 A1 | 6/2013 | |
| WO | WO2013/151736 | * 10/2013 | ............ A61K 48/00 |
| WO | WO 2013/151736 A2 | 10/2013 | |
| WO | WO 14/028487 | * 2/2014 | |
| WO | WO 2014/066811 | 5/2014 | |

(Continued)

OTHER PUBLICATIONS

Diwan et al. (Indian J Orthop. Nov.-Dec. 2013; 47(6): 540-546). (Year: 2013).*
Oreffo et al. (Stem Cell Reviews. 2005; 1: 169-178). (Year: 2005).*
Schrier et al. (AAPS PharmsciTech 2001; 2 (3) article 18, pp. 1-8). (Year: 2001).*
Ou et al., Biomaterials, 2009, 30: 5804-5814.*
Li et al., J. Biomed. Mater. Res., Part A, 2020, 95A: 973-981.*
Kormann et al., Nature Biotechnol., 2011, p. 1-5.*
Dong et al., Proc. Natl. Acad. Sci USA. Feb. 10, 2014, 111: 3955-3960.*
Fang, Jianming, et al. "Stimulation of new bone formation by direct transfer of osteogenic plasmid genes." *Proceedings of the National Academy of Sciences* 93.12 (1996): 5753-5758.
Scherer, Franz, et al. "Nonviral vector loaded collagen sponges for sustained gene delivery in vitro and in vivo." *The Journal of Gene Medicine: A cross-disciplinary journal for research on the science of gene transfer and its clinical applications* 4.6 (2002): 634-643.

(Continued)

*Primary Examiner* — Ileana Popa
(74) *Attorney, Agent, or Firm* — Morse, Barnes-Brown & Pendleton, P.C.; Lisa M. Warren, Esq.; Erin E. Bryan, Esq.

(57) ABSTRACT

The present invention relates to a pharmaceutical composition comprising a polyribonucleotide (RNA) with a sequence which encodes a bone morphogenetic protein (BMP) for use in (i) treating or preventing a bone disease, bone disorder or bone injury; and/or (ii) inducing or enhancing osteogenic differentiation, osteogenesis, ossification, bone regeneration and/or bone morphogenesis in a patient. The present invention also relates to the respective BMP encoding RNAs (BMP RNAs), in particular in its chemically modified form. The present invention also relates to complexes which comprise or are complexed with the BMP RNA, in particular to the respective transfection complexes like lipofection, magnetofection and magnetolipofection complexes. The present invention further relates to a carrier and carrier body to which the RNA or complex has been loaded and to a pharmaceutical composition comprising said carrier or carrier body. The present invention further relates to a matrix or scaffold for sustained mRNA delivery and its application in bone regeneration in vivo, ex vivo and in vitro.

Figure 1:
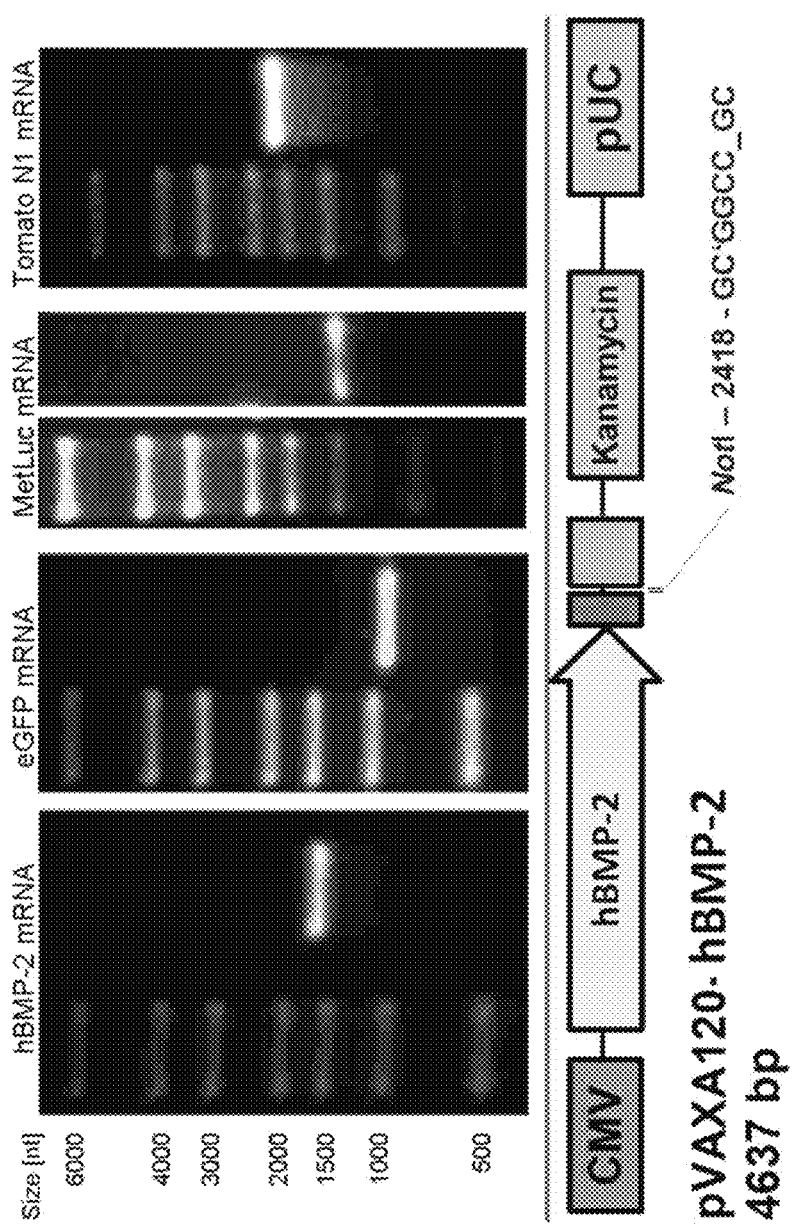

20 Claims, 37 Drawing Sheets
(17 of 37 Drawing Sheet(s) Filed in Color)
Specification includes a Sequence Listing.

(56) References Cited

FOREIGN PATENT DOCUMENTS

| WO | WO 2014/207231 | 12/2014 |
| WO | WO 2014/207231 A1 | 12/2014 |

OTHER PUBLICATIONS

Balmayor, E. R., et al. "Increased osteogenesis after delivering chemically modified messenger RNA encoding BMP-2 in mesenchymal stem cells." *Journal of Tissue Engineering and Regenerative Medicine.* vol. 8. 111 River St, Hoboken 07030-5774, NJ USA: Wiley-Blackwell, 2014.
Lattanzi, Wanda, et al. "Gene therapy for in vivo bone formation: recent advances." European review for medical and pharmacological sciences 9.3 (2005): 167.
International Preliminary Report on Patentability for International Application No. PCT/EP2015/076238, dated May 16, 2017.
Elangovan, et al., "Chemically modified RNA activated matrices enhance bone regeneration," *Journal of Controlled Release*, 218 (2015): 22-28.
Tong, Haijun, et al. "Polyethylenimine600-B-cyclodextrin: a promising nanopolymer for nonviral gene delivery of primary mesenchymal stem cells." *International journal of nanomedicine* 8 (2013): 1935-1946.
Murphy, Kaitlin C., Sophia Y. Fang, and J. Kent Leach. "Human mesenchymal stem cell spheroids in fibrin hydrogels exhibit improved cell survival and potential for bone healing." *Cell and tissue research* 357.1 (2014): 91-99.
Chang, Sophia Chia Ning, et al. "Repair of large cranial defects by hBMP-2 expressing bone marrow stromal cells: Comparison between alginate and collagen type I systems." *Journal of Biomedical Materials Research Part A* 94.2 (2010): 433-441.
Gao, C., et al. "MSC-seeded dense collagen scaffolds with a bolus dose of VEGF promote healing of large bone defects." *European Cells and Materials*, vol. 26 (2013) 195-207.
Thorwarth, M., et al., "Experimental Analysis of Surface Activation of Implants by Liposomal Vectors—A Pilot Study," Abstract 1 page.
Love, Kevin T., et al. "Lipid-like materials for low-dose, in vivo gene silencing." Proceedings of the National Academy of Sciences 107.5 (2010): 1864-1869.
Bettinger, et al., "Peptide-Mediated RNA Delivery: A Novel Approach for Enhanced Transfection of Primary and Post-Mitotic Cells," 2001, Nucleic Acids Res, 29: 3882-91.
Uzgun, et al., "PEGylation Improves Nanoparticle Formation and Transfection Efficiency of Messenger RNA," 2011, Pharm Res, 28: 2223-32.
Sunshine, Joel, et al.: "Small-Molecule End-Groups of Linear Polymer Determine Cell-type Gene-Delivery Efficacy", Advanced Materials, vol. 21, No. 48 (2009), pp. 4947-4951 (XP55095832).
Bhupathiraju et al.: "Synthesis and cellular studies of polyamine conjugates of a mercaptomethyl-carboranylporphyrin", Bioorganic & Medicinal Chemistry, vol. 21, No. 2 (2013), pp. 485-495 (XP055095834).
Aissaoui, Abderrahim et al.: "Efficient topical delivery of plasmid DANN to lung in vivo mediated by putative triggered, PEGylated pDNA nanoparticles", Journal of Controlled Release, vol. 154, No. 3 (2011), pp. 275-284 (XP028285878).
Kolli, Soumia, et al.: "pH-Triggered Nanoparticle Mediated Delivery of siRNA to Liver Cells in Vitro and in Vivo", Bioconugate Chemistry; vol. 24, No. 3 (2013) pp. 314-332 (XP055095835).
Azzam et al.: "Dextran-spermine conjugate: an efficient vector for gene delivery"; Macromolecular Symposia, vol. 195, No. 1 (2003), pp. 247-261 (XP003013580).
Ankinc, et al., Nat. Biotechnol., 2008, 56: 1-20.
Rejman, et al., J. Control., Rel., 2010, 147: 285-391.
International Search Report for Application No. PCT/EP2014/063756 dated Nov. 5, 2014.
Final Rejection issued in Application No. U.S. Appl. No. 14/901,467, issued Aug. 25, 2020.
Non-Final Rejection issued in Application No. U.S. Appl. No. 14/901,467, issued Dec. 17, 2019.
Non-Final Rejection issued in Application No. U.S. Appl. No. 14/901,467, issued Dec. 12, 2019.
Final Rejection issued in Application No. U.S. Appl. No. 14/901,467, issued Sep. 19, 2018.
Non-Final Rejection issued in Application No. U.S. Appl. No. 14/901,467, issued Feb. 22, 2018.
Hosseinkhani, et al., "Impregnation of Plasmid DNA into Three-Dimensional Scaffolds and Medium Perfusion Enhance in Vitro DNA Expression of Mesenchymal Stem Cells," *Tissue Engineering*, 11(9/10):1459-1475 (2005).
Wang, Xu-Li, et al. "Novel polymerizable surfactants with pH-sensitive amphiphilicity and cell membrane disruption for efficient siRNA delivery." *Bioconjugate chemistry* 18.6 (2007): 2169-2177.
Non-Final Rejection issued in Application No. U.S. Appl. No. 14/901,467, issued Aug. 25, 2021.
Jarzębińska, Anita, et al. "A single methylene group in oligoalkylamine-based cationic polymers and lipids promotes enhanced mRNA delivery." *Angewandte Chemie International Edition* 55.33 (2016): 9591-9595.
Uchida, Satoshi, et al., "In Vivo Messenger RNA Introduction into the Central Nervous System Using Polyplex Nanomicelle," *Plos One* 8 (Feb. 2013): 1-8.
Tranchant, et al., "Physicochemical Optimisation of Plasmid Delivery by Cationic Lipids," J. Gene Med 6:S24-S35 (2004).
Non-Final Office Action from U.S. Appl. No. 14/901,467, date mailed: Mar. 10, 2023.
Notice of Allowance in U.S. Appl. No. 14/901,467; dated Apr. 9, 2024.
Final Office Action for U.S. Appl. No. 14/901,467 dated Dec. 14, 2023.
Jarzebinska, A., "Lipid-based Delivery System for Chemically Modified mRNA," Dissertation for obtaining the doctoral degree of the Faculty of Chemistry and Pharmacy of the Ludwig-Maximillians-University Munich, pp. 1-107, Mar. 3, 2017.
Helder, Martinus N., et al. "Expression pattern of osteogenic protein-1 (bone morphogenetic protein-7) in human and mouse development." Journal of Histochemistry & Cytochemistry 43.10 (1995): 1035-1044.
Bulatov A. A., et al., "The experimental and clinical use of bone morphogenetic proteins," Russian Scientific Research Institute of Traumatology and Orthopedics named after R.R. Vreden of the Ministry of Health of the Russian Federation, 005, 2 pages.

* cited by examiner

A. Fibrin

B. FFL-cmRNA

C. BMP-2-cmRNA

Untransfected        50 pg mRNA/cell        100 pg mRNA/cell

Empty collagen sponge    hBMP2 cmRNA-loaded sponge

Empty collagen sponge     hBMP2 cmRNA-loaded sponge before vacuum-drying after vacuum-drying

Figure 26.

IgM,K-FITC

IgG1,K-FITC

CD45-FITC

CD90-FITC

CD29-FITC unstained

IgG1,K-PE

CD106-PE

CD31-PE unstained hBMP2 transfected MSCs          untransfected MSCs

Defect treated with empty sponge

Defect treated with hBMP2 cmRNA-loaded sponge

INDUCTION OF OSTEOGENESIS BY DELIVERING BMP ENCODING RNA

CROSS-REFERENCE OF RELATED APPLICATIONS

This application is a United States National Stage under 35 U.S.C. § 371 of International Application No. PCT/EP2015/076238, Nov. 10, 2015, which claims the benefit of European Application No. 14192539.6, filed Nov. 10, 2014. The content of each of the aforementioned patent applications is hereby incorporated by reference in their entirety. International Application No. PCT/EP2015/076238 was published under PCT Article 21(2) in English.

SEQUENCE LISTING

The instant application contains a Sequence Listing which has been submitted electronically in ASCII format and is hereby incorporated by reference in its entirety. Said ASCII copy, created on May 10, 2017, is named 110016-0022-301-SL and is 32,287 bytes in size.

The present invention relates to a pharmaceutical composition comprising a polyribonucleotide (RNA) with a sequence which encodes a bone morphogenetic protein (BMP) for use in (i) treating or preventing a bone disease, bone disorder or bone injury; and/or (ii) inducing or enhancing osteogenic differentiation, osteogenesis, ossification, bone regeneration and/or bone morphogenesis in a patient. The present invention also relates to the respective BMP encoding RNAs (BMP RNAs), in particular in its chemically modified form. The present invention also relates to complexes which comprise or are complexed with the BMP RNA, in particular to the respective transfection complexes like the lipofection, magnetofection and magnetolipofection complexes. The present invention further relates to a carrier and carrier body to which the RNA or complex has been loaded and to a pharmaceutical composition comprising said carrier or carrier body. The present invention further relates to a matrix or scaffold for sustained mRNA delivery and its application in bone regeneration in vivo, ex vivo and in vitro.

Bone tissue is a type of dense connective tissue largely composed of collagen and hydroxyapatite. Populated by three main cell types—osteoblasts, osteoclasts and osteocytes—bone tissue provides protection to other organs, supports the body, and enables movement (Balmayor, Stem Cell Therapy for Bone Disorders. In: Chase & Vemuri (eds.) Mesenchymal Stem Cell Therapy. Humana Press, New York 2012, 101-116). Bones also produce red and white blood cells within the marrow and store all minerals essential for life (Carmona, Bone Health and Osteoporosis: A Report of the Surgeon General 2004, U.S. Department of Health and Human Services, Office of the Surgeon General, Rockville, MD). When bone tissue is injured, an ossification process occurs attempting the restoration of tissue's normal function. The healing process generally involves coordinated responses of the bone marrow, bone cortex, periosteum and the surrounding soft tissues, including regulation of cellular proliferation, migration and differentiation (Dimitriou, Injury 36(12), 2005, 1392-1404; Einhorn, Clin Orthop Relat Res 355, 1998, 7-21). Many signaling molecules, such as fibroblast growth factors (FGF), bone morphogenetic proteins (BMPs), platelet-derived growth factor and vascular endothelial growth factor (VEGF) are involved in the regulation of new bone formation. Through the release of cytokines, hypoxia and vascular disruption, cells are recruited to the fracture site.

Fracture healing is a complex physiological process. For diverse reasons, this process can fail and, for example, resulting in delayed unions or non-union fractures. Treatment options are mainly designed to enhance the cellular processes that lead to fracture repair. At the same time, biomaterials are often used to provide mechanical support to the fracture site (Tanner, J R Soc Interface 5, 2010, 541-557; Tanner, Proc Inst Mech Eng H 224(12), 2010, 1359-1372) as well as a delivery platform for needed growth factors (Mourino, Expert Opin Drug Deliv 10(10), 2013, 1353-1365; Romagnoli, Clin Cases Miner Bone Metab 10(3), 2013, 155-161).

BMPs are probably the most important growth factors involved in regenerating bone (Bessa, J Tissue Eng Regen Med 2(2-3), 2008, 81-96; Bessa, J Tissue Eng Regen Med 2(1), 2008, 1-13; Urist, Clin Orthop Relat Res 53, 1967, 243-283). They regulate osteogenesis at two different levels: (1) the commitment of skeletal progenitor cells and (2) the maturation of osteoblasts in postnatal development (Yamaguchi, Endocr Rev 21(4), 2000, 393-411). Specifically, BMP-2 has been shown to be effective in inducing osteogenesis both, in vitro and in vivo (Keibl, Injury 42(8), 2011, 814-820; Katagiri, J Cell Biol 127(6 Pt 1), 1994, 1755-1766; Shekaran, Bone regeneration using an alpha 2 beta 1 integrin-specific hydrogel as a BMP-2 delivery vehicle. Biomaterials, 2014). However, treatment of bone defects with BMP proteins (in particular with recombinant BMP-2) is expensive and requires supraphysiological concentrations which run the risk to cause severe side effects like inflammation and the formation of structurally abnormal bone (Zara, Tissue Engineering: Part A 17 (9 & 10), 2011, 1389-1399).

Currently, several scientists explore the possibility of gene transfer to bone tissue with a therapeutic aim. Some advantages of gene delivery over protein delivery have been demonstrated. They include the flexibility to express the protein locally and focally, or in a disseminated fashion, as needed. In addition, proteins are produced intracellularly. Thus, this facilitates therapeutic pathways to take place. Unlike its recombinant equivalent, the protein delivered via gene transfer will be nascent and uncontaminated by a variable percentage of incorrectly folded and possibly antigenic molecules (Evans, Adv Drug Deliv Rev 64(12), 2012, 1331-1340). Furthermore, proteins can be expressed for extended periods of time and the level of transgene expression can be regulated. Thus, the doses of therapeutic proteins used during treatment are reduced (Evans, 2012, loc. cit.). In particular, gene transfer using plasmid DNA encoding BMP-2 was shown to have some potential for bone healing and regeneration (Lu, J Biomater Sci Polym Ed 23(1-4), 2012, 509-526; Chang, Neurosurgery 65, 2009, 75-81; Park, Gene Ther 10(13), 2003, 1089-1098).

However, despite some advantages, current viral vectors for gene delivery are associated with safety concerns including strong immunogenicity and insertional mutagenesis. Non-viral vectors are limited by low gene transfer efficiency (Evans, 2012, loc. cit.). The latter has been predominately attributed to the insufficient transport of plasmid DNA into the nucleus.

An alternative to DNA-based gene therapy is messenger RNA (mRNA) delivery. Recently, transcript therapy, using mRNA, has gained dramatic interest as a safer substitute for gene and recombinant protein therapy. mRNAs neither harbor the risk of immunogenicity, nor the potential mutagenicity, which are accompanied with recombinant protein and gene therapy, respectively. A further technical advantage is that mRNAs only need to reach the cytoplasm to become active, while DNA needs to reach the nucleus (Yamamoto, European Journal of Pharmaceutics and Biopharmaceutics 71, 2009, 484-489; Tavernier, Journal of Controlled Release 150, 2011, 238-247). Accordingly, mRNAs are emerging as pioneer therapeutics in a broad variety of medical indications (Yamamoto, European Journal of Pharmaceutics and Biopharmaceutics 71, 2009, 484-4891; Tavernier, Journal of Controlled Release 150, 2011, 238-247; Kormann, Nature Biotechnology 29, 2011, 154-157; Esteller, Nature Review Genetics 12, 2011, 861-874). In particular, mRNA has recently emerged as an alternative for non-viral gene therapy. Since mRNA exerts its function in the cytoplasm, limitations related to the transport across the nuclear membrane are overcome; they are not relevant with respect to mRNA-based transcript therapy.

Although mRNA clearly represents a potential tool for many therapeutics, clinical applications have so far been limited (for example to cancer vaccination) due to strong immunogenicity and limited stability of conventional mRNAs (Van Tendeloo, Curr Opin Mol Ther 9(5), 2007, 423-431).

Holtkamp demonstrated an increase in mRNA stability by the addition of a poly(A) tail of 120 nucleotides in length (Blood 108(13), 2006, 4009-4017). Further, Holtkamp has also reported a study on the optimization of UTRs to achieve stability and translational efficiency (Holtkamp loc. cit.). Moreover, chemical modifications of mRNA were reported that result in an increased stability and decreased activation of the innate immune system. In particular, the generation and therapeutic potential of chemically modified mRNA (cmRNA) that codes for therapeutic mouse erythropoietin (EPO) and surfactant protein B (SP-B) has been reported to induce hematopoiesis and to have potential in the treatment of lethal congenital lung disease, respectively (Kormann, Nat Biotechnol 29(2), 2011, 154-157). In addition, collagen sponges have been used as 3D matrices for loading DNA or cmRNA, and also seeding the cells on them) Chevallay, Medical and Biological Engineering and Computing 38, 2000, 211-218; Reckhenrich, Biomaterials 32, 2011, 1996-2003; Scherer, The Journal of Gene Medicine 4, 2002, 634-643; Elangovan, Journal of Controlled Release 218, 2015, 22-28; WO 01/00708). Recent studies have shown that, as compared to 'petri dish'-based 2D cell cultures, culturing cells within 3D scaffolds more closely resembles the in vivo situation with regard to cell shape, cell signaling and cellular behavior, which can influence gene expression in the cells (Mueller-Klieser, American Journal of Pysiology-Cell Physiology, 273, 1997, C1109-C1123). Collagen sponges are one of the 3D matrices that can modify migration, attachment, adhesion, and in certain cases, the differentiation of cells (Chevallay, Medical and Biological Engineering and Computing 38, 2000, 211-218). Furthermore, treatment of allergic asthma by cmRNA encoding the T all transcription factor FOXP3 has been proposed by Mays (J Clin Invest 123(3), 2013, 1216-1228). CmRNA as an improved therapeutic tool for diseases related to deficient or defective genes or proteins is also disclosed in WO 2011/012316. In general, transcript therapies using cmRNA are emerging as safer yet promising substitutes for gene and recombinant protein therapies. However, their applications have been limited due to transient translation and relative low stability of cmRNAs as compared to DNAs. Moreover, for example in cases where EPO cmRNA is employed, a repeated application/administration is assumed to be required for successful treatment (constant adaption of hematocrit required).

A more advanced approach in gene therapy is the use of genetically modified autologous tissue grafts to repair defective tissue. This therapeutic strategy pursues to stimulate the healing process by delivering genes through a minimally manipulated, autologous tissue that contains progenitor cells and possess the properties of space filling, inductive or conductive scaffold (Evans, Eur Cell Mater 18, 2009, 96-111; Evans, Tissue Eng 13(8), 2007, 1987-1993). For example, fat tissue is known to possess osteoprogenitor cells; it has the ability to serve as natural scaffolding material and it can be easily harvested (Evans, 2009, loc. cit.; Dragoo, Plast Reconstr Surg 115(6), 2005, 1665-1673). Evans (2009, loc. cit.) used fat and muscle tissue grafts transduced with adenovirus carrying human BMP-2 cDNA to repair bone and cartilage defects. However, also this approach suffers from the above described drawbacks.

For years, sustained gene or drug delivery systems have been catching an increasing interest, because they do not require the application of repetitive doses. As a result, patients can use their medications with more ease, and this can lead to better acceptance of therapeutic approaches (Bartus, Science 281, 1998, 1161). In case of RNA therapy such retard delivery systems would be particularly suitable when long-term protein expression is aimed at, for example in bone diseases. Nevertheless, efficient methods for sustained delivery of RNA are lacking so far.

Thus, the technical problem underlying the present invention is the provision of improved means and methods for medical intervention related to the bone.

The technical problem is solved by provision of the embodiments characterized in the claims.

Accordingly, the present invention relates to a pharmaceutical composition comprising a polyribonucleotide (RNA) with a sequence which encodes a bone morphogenetic protein (BMP) for use in (i) treating or preventing a bone disease, bone disorder or bone injury; and/or
(ii) inducing or enhancing osteogenic differentiation, osteogenesis, ossification, bone regeneration and/or bone morphogenesis
in a patient.

The present invention also relates to a method of
(i) treating or preventing a bone disease, bone disorder or bone injury; and/or
(ii) inducing or enhancing osteogenic differentiation, osteogenesis, ossification, bone regeneration and/or bone morphogenesis
(in a patient in need thereof), said method comprising the step of administering to a patient in need thereof a pharmaceutically effective amount of (a pharmaceutical composition comprising) an RNA with a sequence which encodes a bone BMP.

The present invention solves the above identified technical problem since, as documented herein below and in the appended examples, it was surprisingly found that RNA coding for (a) BMP(s), in particular a cmRNA coding for human BMP-2 (SEQ ID NO. 3 encoded by SEQ ID NO. 1; hBMP-2 cmRNA) or human BMP-7 (SEQ ID NO. 4 encoded by SEQ ID NO. 2; hBMP-7 cmRNA), induces/enhances osteogenesis. Hence, in the context of the present invention, the proof of principle was made that RNA encoding (a) BMP(s) can successfully be employed in transcript therapy for bone regeneration and in the treatment or prevention of bone-related diseases, disorders or injuries, respectively.

Furthermore, in the context of the present invention, evidence is provided that a single treatment with BMP-encoding RNA (BMP RNA) is sufficient for a sound/complete treatment (or prevention) of bone-related diseases, disorders or injuries. Hence, one advantage of the means and methods of the invention is that BMP RNA is required to be administered only once.

Another advantage of the means and methods of the invention is that an alternative to DNA-based gene therapy and conventional transcript therapy can be applied without the respective limitations of, for example, viral and non-viral vectors and without the drawbacks of safety concerns and/or limited stability/expressivity.

Another advantage of using the RNA in accordance with the invention is that (for example in contrast to the use of DNA vectors) the duration of the treatment is adjustable. For example in the case of the induction of stem cells, it is a desirable rule that the transcription factors are only transiently active, in order to reprogram somatic cells into stem cells. Through dosed administration of the relevant RNA encoding (a) BMP(s), the activity is controllable over time. In contrast to this, the previously known methods run the risk of integration of the genes administered, which may lead to complications, e.g. tumorigenesis, and, moreover, may render it impossible to control the duration.

The present invention is particularly based on the experiments described in the appended examples.

These examples inter alia show that cells (e.g. MSCs like BMSCs and AMSCs) transfected with BMP RNA (e.g. hBMP-2 or -7 cmRNA) secreted elevated levels of biologically active BMP (e.g. BMP-2 or BMP-7), in particular on a long-term basis (e.g. for over 7 days). These levels of secreted protein were effective in inducing osteogenic differentiation (in in vitro experiments). This was indicated by the expression of osteogenic markers, in particular by determining elevated alkaline phosphatase (ALP) levels which were revealed in transfected cells, and by enhanced expression of RunX2, ALP, Osterix, Osteocalcin, Osteopontin and Collagen Type I (detected by quantitative RT-PCR). Moreover, this was indicated (in vitro) by mineralization (deposited mineralized matrix). Mineralization was shown by positive Alizarin red staining which was achieved at 2 weeks after transfection (MSCs with the respective cmRNA). The osteogenic potential of BMP RNA (like hBMP-2 and -7 cmRNA) is also demonstrated for human fat/adipose tissue transfected with the respective BMP RNA (ex vivo). The human fat/adipose tissue also yielded an osteogenic response (in vitro), as indicated by expression of hBMP-2, RunX2, ALP and Collagen Type I.

It was also demonstrated in the context of the invention that transfection conditions can be optimized to obtain higher transfection efficiencies, even with minimized cytotoxicity. In this context, transfection of MSCs with cmRNA was first studied by using several transfection reagents and different reporter cmRNAs (fluorescent proteins). High transfection efficiencies were achieved resulting in sustained protein expression (up to 5 days). Expression peak was typically observed between 24 and 48 hours after transfection.

Furthermore, cytotoxicity screening was performed to test the biocompatibility of the complexes used to transfect MSCs. From the results of expression and cell viability, the best transfection protocols were selected to further transfect cells (MSCs) with BMP RNA (e.g. hBMP-2 or -7 cmRNA).

In particular, it was shown by using *Metridia* luciferase as a reporter system, that DreamFect Gold (DF-Gold) is a highly suitable non-viral lipid enhancer to deliver the (cm)RNAs into the cells. The DF-Gold/(cm)RNA complexes were highly efficient in (cm)RNA transfection but very mild to the cells. For transfection purposes, lipofection and magnetofection procedures were employed in the context of the invention and the appended examples. Thereby, robust enhancement of the transfection efficiency was obtained with a variety of (cm)RNAs, in particular in the two different primary cell types, AMSCs and BMSCs. In particular, it was shown that transfer of BMP RNA (e.g. hBMP-2 or -7 cmRNA) into cells (e.g. MSCs like BMSCs and AMSCs) by both, lipofection and magnetofection, supported in vitro osteogenesis.

The highest transfection efficiency was achieved with magnetofection, in particular when magnetofection was applied to MSCs (e.g. BMSCs or AMSCs).

Especially BMSCs are considered difficult to be transfected (Lakshmipathy, Stem cells 22(4), 2004, 531-543). However, it was shown in the context of this invention that even with BMSCs, an efficient transfection via magnetofection with eGFP cmRNA magnetic lipoplexes can be achieved resulting in 80% positive cells after 24 hours. Similarly, when hBMP-2 cmRNA was used, 6-fold increase in Magnetofection Advantage Index (MAI) was quantified in AMSCs. In particular, hBMP-2-transfected AMSCs were able to secrete considerably higher amounts of hBMP-2 as compared to the untransfected cells for over 7 days. In this case, a plateau in protein expression was observed between 24 and 72 hours. This effect may also be of benefit for the therapeutic action of hBMP-2 cmRNA (or another BMP RNA) in accordance with this invention. Indeed, as a result of the constant production of hBMP-2 (or another BMP) by the transfected cells, osteogenic gene expression and mineralization was also enhanced.

Moreover, AMSCs transfected via magnetofection exhibited higher expression of the transcription factor RunX2, osteopontin and alkaline phosphatase as well as higher mineral deposition. Without being bound by theory, the expression of RunX2 reflects the role of the transcription factor RunX2 in controlling the progression of osteogenic differentiation. AMSCs transfected with hBMP-2 cmRNA via magnetofection showed the highest and sustained expression of RunX2, which, in turn, correlates well with the more pronounced osteogenesis observed in those samples in vitro.

In principle, what has been said above with respect to BMP-2, was likewise also shown in the context of the invention with respect to BMP-7. In particular, hBMP-7-transfected AMSCs were able to secrete considerably higher amounts of hBMP-7 as compared to the untransfected cells for over 3 days. In this case, a maximum protein expression was observed 24 hours post-transfection. Two different hBMP-7 cmRNA doses were tested, namely 20 and 32 pg/cell. Cells transfected with 20 pg/cell resulted in significantly higher hBMP-7 secretion when compared to the 32 pg/cell dose. Transfected AMSCs were able to deposit mineralized matrix, indicating enhanced osteogenesis in those samples in vitro.

As mentioned, it was further demonstrated in the context of this invention that fat tissue biopsies transfected with hBMP-2 cmRNA (or another BMP RNA) expressed enhanced hBMP-2 levels (or level of another BMP), which in turn upregulated the expression of several osteogenic markers when cultured in vitro for up to 7 days. Based on these results, it can be concluded that hBMP-2 transfected fat implants (or fat implants transfected with other BMP) could act as an efficient source of hBMP-2 (or of another BMP) and the respective progenitor cells for autologous tissue repair. Hence, the in vitro results achieved in the context of this invention show that BMP RNA, in particular hBMP-2 and -7 cmRNA, represents a step forward in the application of autologous tissue graft technology for bone regeneration. It avoids the use of viral vectors and their associated drawbacks (safety concerns etc., see above).

The appended examples and the disclosure provided herein, further provide for a sound basis for studies addressing bone formation in clinically relevant animal models. Hence, such studies can readily be performed by the skilled person.

As a respective non-limiting example, hBMP-2 cmRNA was grafted onto bone implant materials and administered in vivo to a non-critical size bone defect in the femur of rats. Obtained Micro Computer Tomography (μCT) results support the therapeutic effect of hBMP-2 cmRNA in bone healing. In those animals treated with hBMP-2 cmRNA a stimulation of in vivo osteogenesis was observed. In contrast, in animals treated with unspecific cmRNA (e.g. cmRNA encoding firefly luciferase (FFL)) no osteogenesis was observed. This demonstrates that hBMP-2 cmRNA mediates the therapeutic expression of hBMP-2 in vivo at the site of the bone defect causing osteogenesis to occur.

It was further demonstrated in the context of the invention, that carrier/carrier bodies (for example collagen sponges or fibrin clots) can be part of an efficient transfection system when loaded with RNA, in particular BMP-encoding RNA, and when also cells to be transfected have been seeded on them. As such, the carrier/carrier bodies can function as 3D matrixes in bone regeneration. In addition, evidence has been provided in the context of the present invention that carrier/carrier bodies (e.g. collagen sponges or fibrin clots) can be used not only as a 3D scaffold for seeding the cells, but also as depots for sustained delivery of RNA (in particular BMP-coding RNA, e.g. cmRNA or even non-chemically modified BMP-encoding RNA).

In particular, and as demonstrated in the appended examples, firstly collagen sponges were pre-loaded with (m)RNA containing lipoplexes and vacuum-dried. Then the dried, loaded sponges were used as 3D matrices for cell seeding. Hence, the present invention also relates to a delivery system which combines and simplifies the cell seeding and (m)RNA transfection steps into one single step. Additionally, (m)RNA-loaded collagen sponges showed retard delivery properties. As such, they can overcome the rapid and transient production of proteins after a classical 2D mRNA. transfection. As an example for clinical application, bone regeneration was investigated in vitro and in vivo using hBMP2 (m)RNA-loaded collagen sponges. Moreover, to investigate the potential of vacuum-dried (m)RNA-loaded collagen sponges as ready-to-use bioproducts, their shelf life was estimated in a successful long-term stability assay. Hence, the invention further provides a sustained (m)RNA delivery depot. This opens new ways for a convenient yet safe substitute for gene therapy in clinical approaches.

Surprisingly, it was even possible in context of the invention to demonstrate that also unmodified (m)RNA may successfully be used for gene therapy purposes, in particular when being part of the sustained delivery system/depot as disclosed herein and when being administered by this system/depot.

Another advantage of this invention was high cell transfection efficacy (close to 100%) and low cell toxicity. As mentioned, considering stability issues, vacuum-dried RNAs, in particular when loaded on collagen sponges, were stable over a long time (e.g. for at least 6 months at RT). Further, in the context of the invention, bone regeneration in vitro (with MC3T3-E1 cells and MSCs), and in vivo (in rat femur defects), using hBMP2 RNAs, confirmed the ability of the system in a preclinical application.

All in all, the invention inter alia provides for RNA-loaded (vacuum-dried) carrier (collagen sponges) as stable and efficient RNA delivery systems for prolonged protein expression, thereby bringing transcript therapy a step closer to the clinical approaches. In particular, the present invention revealed the safety, efficiency, and stability of RNA-loaded vacuum-dried collagen sponges, as ready-to-use bioproducts. The respective virus free, and gene free technology, provides an RNA sustained delivery system, which is independent from RNA modifications, cell type and cell density. Investigating bone differentiation in vitro and in vivo with this technology, confirmed the ability of RNA-loaded vacuum-dried collagen sponges for clinical applications, when a prolonged protein delivery meets the aim of therapy. This study opens new ways for easier yet promising applications of messenger RNA, which surpass DNA-based gene therapy in safety aspects.

The present invention further relates to the following items:

1. A pharmaceutical composition comprising a polyribonucleotide (RNA) with a sequence which encodes a bone morphogenetic protein (BMP) for use in
   (i) treating or preventing a bone disease, bone disorder or bone injury; and/or
   (ii) inducing or enhancing osteogenic differentiation, osteogenesis, ossification, bone regeneration and/or bone morphogenesis in a patient.
2. The pharmaceutical composition of item 1, wherein said BMP is BMP-2 or BMP-7.
3. The pharmaceutical composition of item 1 or 2, wherein said RNA is encapsulated.
4. The pharmaceutical composition of any one of items 1 to 3, wherein said RNA is to be transfected by lipofection.
5. The pharmaceutical composition of any one of items 1 to 4, wherein said RNA is to be transfected by magnetofection.
6. The pharmaceutical composition of item 5, further comprising magnetic nanoparticles (MNPs).
7. The pharmaceutical composition of any one of items 4 to 6, further comprising a liposomal transfection reagent (LTR).
8. The pharmaceutical composition of item 7, wherein the w/w ratio of said LTR to said RNA is from 2 to 20 μg of said LTR per μg of said RNA.
9. The pharmaceutical composition of item 7 or 8, wherein the ratio of said MNPs to said LTR to said RNA is about 0.5 (iron weight):about 2 to 5 or 4 to 7 (weight):about 1 (weight), respectively.
10. The pharmaceutical composition of any one of items 1 to 9, wherein said RNA is to be delivered in vivo.
11. The pharmaceutical composition of item 10, wherein said RNA is to be administered directly into the bone or the bone tissue of said patient.
12. The pharmaceutical composition of any one of items 1 to 9, wherein said RNA is delivered ex vivo to cells which are to be introduced into said patient.
13. The pharmaceutical composition of item 12, wherein said RNA is delivered ex vivo to cells of said patient and wherein said cells to which said RNA has been delivered are to be reintroduced into said patient.

14. The pharmaceutical composition of item 12 or 13, wherein said cells are osteoprogenitor cells.
15. The pharmaceutical composition of any one of items 12 to 14, wherein said cells are mesenchymal stem cells (MSCs).
16. The pharmaceutical composition of item 15, wherein said MSCs are adipose-derived mesenchymal stem cells (AMSCs) or bone marrow-derived MSCs (BMSCs).
17. An RNA with a sequence which encodes BMP-2 or BMP-7, wherein 25% of the cytidines of said RNA are 5-methylcytidines (m5C) and 25% of the uridines of said RNA are 2-thiouridines (s2U).
18. The pharmaceutical composition of any one of items 1 to 16, wherein said RNA is the RNA of item 17.

In principle, the pharmaceutical composition of the invention is for use in treating or preventing any disease, disorder, defect or injury which is related to, is associated with, is physiologically linked to or affects the bone (also referred to herein simply as bone disease). In this context, the RNA according to the invention may be used for therapy or prevention so that in a cell or tissue into which the RNA is to be introduced, (a) BMP(s) can be formed which is/are naturally not expressed to the desired extent or at all. The RNA may be used in both cases, (i) when a BMP is not formed owing to a deficiency of a gene and also owing to a disease or (ii) in cases where the introduction of a BMP is advantageous for the body. The RNA can also be used for supplementing a BMP which is not expressed to an adequate extent.

In particular, the bone disease to be treated or prevented in accordance with the invention is related to, associated with or physiologically linked to the (function of) one or more BMP(s) like, for example, BMP-1, BMP-2, BMP-3, BMP-4, BMP-5, BMP-6, BMP-7, BMP-8a, BMP-8b, BMP-10 and/or BMP-15, preferably BMP-7, more preferably, BMP-2. More particularly, the bone disease to be treated in accordance with the invention is a bone disease (the symptoms of) which can be treated, prevented or ameliorated by a delivery, induction and/or increase of the (function of) one or more BMP(s).

The pharmaceutical composition of the invention is also for use in inducing or enhancing osteogenic differentiation (e.g. differentiation of MSCs into osteogenic cells), osteogenesis, ossification, bone regeneration, bone morphogenesis bone formation, bone growth, mineralization and/or calcification, in particular in a patient and, more particular, in the context of the treatment or prevention of a bone disease in the context of the invention.

Many kinds of bone diseases are known in the art and are, for example, described in Evans (2012, loc. cit.), in particular in Table 1 thereof. Examples of bone diseases to be treated or prevented in the context of the invention are osteogenesis imperfecta (a monogenic, dominant negative, genetic disease), (degenerative) osteoporosis, (osteoporotic) fractures, non-unions, bone defects, segmental defects, bone cysts, spine fusion, avascular necrosis, bone tumors (e.g. osteosarcoma, ewing's sarcoma), osteolysis (e.g. cancer induced osteolysis, aseptic loosening).

One particular field in which BMP RNA may be used in accordance with the invention is the field of bone-related regenerative medicine. In the context of disease processes or aging, degenerative bone diseases arise which can be treated, moderated, prevented or even cured by introduction of (a) BMP(s), in particular if the BMP(s) is (are) produced too little or not at all owing to the disease or aging processes. By introduction of the relevant BMP RNA encoding (a) BMP(s), the degenerative process can be halted or regeneration can even be initiated. Hence, in one aspect, the bone disease to be treated or prevented in accordance with the invention is a degenerative bone disease. Examples of degenerative bone diseases are degenerative osteoporosis, Paget's disease, spondylosis (also known as progressive degenerative arthritis), osteomalacia and Rickets, among others.

In one aspect, the pharmaceutical composition of the invention is for use in bone healing. For example, (osteoporotic) fractures, non-unions, segmental defects, bone cysts, spine fusion, avascular necrosis are to be healed in this context.

In particular, non-unions, segmental bone defects and fractures, more particular osteoporotic fractures, are envisaged to be treated, prevented and/or healed in accordance with the invention.

The RNA to be employed according to the invention may also have an influence on the course of a bone disease. Examples are bone diseases which are not directly attributable to a gene defect but wherein the disease process can be positively influenced by means of BMP RNA expression. Examples are BMPs for bone healing as factors for "tissue engineering".

The BMP encoded by the RNA in accordance with the invention may be BMP-1, BMP-2, BMP-3, BMP-4, BMP-5, BMP-6, BMP-7, BMP-8a, BMP-8b, BMP-10 and/or BMP-15, preferably BMP-7, more preferably, BMP-2. Preferred BMP's to be employed in accordance with the invention are human BMPs (hBMPs). BMPs are well known in the art and are, for example described in (Bessa, J Tissue Eng Regen Med 2(2-3) loc. cit; Bessa, J Tissue Eng Regen Med 2(1) loc. cit; Urist, loc. cit.). The nucleotide and amino acid sequences of the (h)BMPs are available via databases known in the art (e.g. NCBI under http://www.ncbi.nlm.nih.gov/). Examples of respective database entries are listed in Table 5, infra.

The particular nucleotide sequence of hBMP-2 is depicted in SEQ ID NO. 1. The particular nucleotide sequence of hBMP-7 is depicted in SEQ ID NO. 2. The particular amino acid sequence of hBMP-2 is depicted in SEQ ID NO. 3. The particular amino acid sequence of hBMP-7 is depicted in SEQ ID NO. 4.

It is envisaged in the context of the invention that the term "BMP" (or "BMP RNA") also encompasses functional fragments and variants of the respective BMP (or of the respective BMP RNA).

Beside the BMP RNA itself, also variants of the BMP RNA may be employed in accordance with the invention. A variant of a BMP RNA may structurally differ from the BMP RNA itself but still be functionally active in the same manner as the BMP RNA itself. In particular, a variant of a BMP RNA is intended to encode a protein capable to function as the respective BMP itself, i.e. capable to exhibit bone morphogenetic activity. More particular, a variant of a BMP RNA is intended to encode a protein capable to regulate osteogenesis. In this context, osteogenesis may be regulated at two different levels: (i) the commitment of skeletal progenitor cells; and/or (ii) the maturation of osteoblasts in postnatal development. As such, a variant of a BMP RNA is intended to encode a protein capable to induce or enhance osteogenic differentiation, osteogenesis, ossification, bone regeneration and/or bone morphogenesis. The skilled person is readily in the position to determine whether a given variant of a BMP RNA functions as the respective BMP RNA itself, for example, encodes a protein capable to exhibit bone morphogenetic activity. For this purpose, the skilled person may rely on respective means and methods of the prior art (e.g. as disclosed in Yamaguchi loc. cit.) and provided in the appended examples. For example, the skilled person may determine whether a given variant of a BMP RNA induces osteogenesis in vitro, ex vivo and/or in vivo (e.g. as determined in appended example 5 or 7, respectively).

In principle, the more similar a variant of a BMP RNA is to the respective BMP RNA itself, the more preferred the variant is.

A particular BMP RNA or variant of a BMP RNA in accordance with the invention may be an RNA selected from the group consisting of:
(a) an RNA encoding an amino acid sequence of BMP-1, BMP-2 (particularly preferred), BMP-3, BMP-4, BMP-5, BMP-6, BMP-7 (preferred), BMP-8a, BMP-8b, BMP-10 or BMP-15, e.g. encoding an amino acid sequence as depicted in SEQ ID NO. 3 or SEQ ID NO. 4;
(b) an RNA encoding an amino acid sequence of BMP-1, BMP-2 (particularly preferred), BMP-3, BMP-4, BMP-5, BMP-6, BMP-7 (preferred), BMP-8a, BMP-8b, BMP-10 or BMP-15 having one or more amino acid residues substituted, inserted and/or deleted, e.g. encoding an amino acid sequence as depicted in SEQ ID NO. 3 or SEQ ID NO. 4 having one or more amino acid residues substituted, inserted and/or deleted (wherein said RNA encodes a protein capable to exhibit bone morphogenetic activity);
(c) an RNA (encoded by a nucleotide sequence) that hybridizes to the complementary strand of a nucleotide sequence encoding an amino acid sequence of BMP-1, BMP-2 (particularly preferred), BMP-3, BMP-4, BMP-5, BMP-6, BMP-7 (preferred), BMP-8a, BMP-8b, BMP-10 or BMP-15, e.g. encoding an amino acid sequence as depicted in SEQ ID NO. 3 or SEQ ID NO. 4 (wherein said RNA encodes a protein capable to exhibit bone morphogenetic activity); and
(d) an RNA encoding an amino acid sequence which is at least 50%, at least 60%, at least 70%, at least 75%, at least 80%, at least 85%, at least 90%, at least 95%, at least 96%, at least 97%, at least 98% or at least 99% identical to the (full length) amino acid sequence of BMP-1, BMP-2 (particularly preferred), BMP-3, BMP-4, BMP-5, BMP-6, BMP-7 (preferred), BMP-8a, BMP-8b, BMP-10 or BMP-15, e.g. to the (full length) amino acid sequence as depicted in SEQ ID NO. 3 or SEQ ID NO. 4 (wherein said RNA encodes a protein capable to exhibit bone morphogenetic activity).

In the context of the invention, "having one or more amino acid residues substituted, inserted and/or deleted" particularly means having at most 500, at most 400, at most 300, at most 200, at most 100, at most 50, at most 30, at most 20, at most 10, at most 9, at most 8, at most 7, at most 6, at most 5, at most 4, at most 3, at most 2 or 1 amino acid residues substituted, inserted and/or deleted. In one specific aspect, this term means one or more amino acid exchanges, preferably conservative amino acid exchanges, e.g. at most 500, at most 400, at most 300, at most 200, at most 100, at most 50, at most 30, at most 20, at most 10, at most 9, at most 8, at most 7, at most 6, at most 5, at most 4, at most 3, at most 2 or 1 (conservative) amino acid exchange(s).

In the context of the invention, "hybridizing" means that hybridization can occur between one nucleic acid molecule and another (complementary) nucleic acid molecule. Hybridization of two nucleic acid molecules usually occurs under conventional hybridization conditions. In the context of the invention, stringent hybridization conditions are preferred. Hybridization conditions are, for instance, described in Sambrook and Russell (2001), Molecular Cloning: A Laboratory Manual, CSH Press, Cold Spring Harbor, NY, USA. In a particular embodiment, "hybridizing" means that hybridization occurs under the following (stringent) hybridization conditions:

| | |
|---|---|
| Hybridization buffer: | 2 × SSC, preferably 1 × SSC; 10 × Denhardt solution (Fikoll 400 + PEG + BSA; ratio 1:1:1); 0.1% SDS; 5 mM EDTA; 50 mM Na$_2$HPO$_4$; 250 µg/ml of herring sperm DNA; 50 µg/ml of tRNA; or 0.25M of sodium phosphate buffer, pH 7.2; 1 mM EDTA 7% SDS |
| Hybridization temperature T | 60° C., preferably 65° C. |
| Washing buffer: | 2 × SSC, preferably 1 × SSC, more preferably 0.1 × SSC; 0.1% SDS |
| Washing temperature T | 60° C., preferably 65° C. |

As mentioned, also an RNA encoding a functional fragment of a BMP may be employed in accordance with the invention. "Functional" in this context means that the fragment is functionally active in the same manner as the respective full length BMP RNA. In particular, a functionally active fragment of a BMP is a fragment of a BMP which is still capable to exhibit bone morphogenetic activity. What has been said herein above with respect to the functional activity of the variant of the BMP RNA, also applies to the functional fragment of a BMP, mutatis mutandis.

A particular (functional) fragment of a BMP may be an amino acid stretch of at least 50, at least 100, at least 150, at least 200, at least 300, at least 500 or at least 700 (consecutive) amino acid residues of the respective BMP.

A BMP RNA encoding a functional fragment of a protein encoded by any of the herein described variants of BMP RNA may also be employed in the context of the invention. Also such BMP RNA is particularly intended to encode a protein capable to function as the respective BMP, i.e. capable to exhibit bone morphogenetic activity. What has been said herein above with respect to the functional activity of the variant of the BMP RNA and the BMP fragment, also applies to such BMP RNA, mutatis mutandis.

In principle, the meaning of the term "BMP RNA" as used herein encompasses all, (i) the herein described RNA encoding a BMP itself and a full length BMP, respectively, (ii) the herein described variant RNA encoding a BMP variant, and (iii) the herein described RNA encoding (a variant of) a functional fragment of a BMP.

Exemplified nucleotide sequences of BMP RNAs/BMP RNA constructs to be employed in accordance with the invention are despicted in SEQ ID NOs. 29 or 30 (both hBMP-2 (cm)RNAs) and SEQ ID NOs. 29 (hBMP-7 (cm) RNA).

In the context of the invention, RNA should be understood to mean any polyribonucleotide molecule which, if it comes into the cell, is suitable for the expression of a protein or functional fragment thereof or is translatable to a protein or functional fragment thereof. The term "protein" here encompasses any kind of amino acid sequence, i.e. chains of two or more amino acid residues which are each linked via peptide bonds and also includes peptides and fusion proteins.

In a particularly preferred aspect, the RNA to be employed in accordance with the invention, e.g. to be comprised in the pharmaceutical composition of the invention, is a messenger RNA (mRNA). This means that, according to this aspect, any of the herein defined RNA may be in the form of an mRNA.

The RNA to be employed may be a double-stranded RNA (for example due to inter- or intramolecular hybridization) or, preferably, a single-stranded RNA (which, however, may comprise at least (a) double-stranded part(s) due to intramolecular hybridization; for example (a) hairpin structure(s)).

In one aspect, the RNA to be employed in accordance with the invention is a non-naturally occurring RNA, in particular a non-naturally occurring mRNA.

The RNA to be employed in accordance with the invention may be a chemically modified RNA (cmRNA). This is, in principle, preferred. CmRNAs are known in the art and are, for example, described in Kormann (loc. cit.), Mays (loc. cit.) and WO 2011/012316. In particular, the cmRNA to be employed may be a cmRNA as described in WO 2011/012316.

It is preferred that the RNA and, in particular, the cmRNA to be employed in accordance with the invention has increased stability and/or decreased immunogenicity. In particular, it is envisaged that the RNA and, in particular, the cmRNA abrogates RNA interaction with Toll-like receptors and/or with retinoid-inducible gene I (RIG-I). In principle, this applies to any (cm)RNA as defined herein.

Immunogenicity and stability can be determined in a manner known per se.

For the determination of the immunogenicity of an RNA, various methods well known to those skilled in the art can be used. A very suitable method is the determination of inflammatory markers in cells as a reaction to the administration of RNA. Cytokines which are associated with inflammation, such as for example TNF-α, IFN-α, IFN-β, IL-8, IL-6, IL-12 or other cytokines known to those skilled in the art are normally measured. The expression of DC activation markers can also be used for the estimation of immunogenicity. A further indication of an immunological reaction is the detection of binding to the Toll-like receptors TLR-3, TLR-7 and TLR-8 and to helicase RIG-1.

The immunogenicity is as a rule determined in relation to a control. In a common method, the RNA to be employed according to the invention is administered to cells and the secretion of inflammatory markers in a defined time interval as a reaction to the administration of the RNA is measured. As the standard used for comparison, RNA which is known to cause little or no immune response may be used, in which case the immune response to the RNA to be employed according to the invention should then lie in the same range and not be elevated. With the RNA to be employed according to the invention it is, for example, envisaged to lower the immune response by at least 30%, as a rule at least 50% or even 75% or even to prevent it completely.

The immunogenicity can be determined by measurement of the aforesaid factors, in particular by measurement of the TNF-α and IL-8 levels and the binding capacity to TLR-3, TLR-7, TLR-8 and helicase RIG-1. In order thereby to establish whether an (m)RNA has the desired low immunogenicity, the quantity of one or more of the aforesaid factors after administration of the polyribonucleotide concerned can be measured. Thus for example a quantity of the (m)RNA to be tested can be administered to mice via the caudal vein or i.p. and then one or more of the aforesaid factors can be measured in the blood after a predefined period, e.g. after 7 or 14 days. The quantity of factor is then related to the quantity of factor which is present in the blood of untreated animals. For the determination of the immunogenicity it has been found very valuable to determine the binding capacity to TLR-3, TLR-7, TLR-8 and/or helicase RIG-1. The TNF-α levels and IL-8 levels also provide very good indications. With the (m)RNA to be employed according to the invention, it is, for example possible to lower the binding capacity to TLR-3, TLR-7, TLR-8 and RIG-1 by at least 50% compared to unmodified RNA. As a rule it is possible to lower the binding to said factors by at least 75% or even by 80%. In preferred embodiments, the binding capacity to TLR-3, TLR-7, TLR-8 and RIG-1 lies in the same range for the (m)RNA to be employed according to the invention and for animals to which no mRNA was administered. In other words, in one particular aspect, the (m)RNA to be employed according to the invention is envisaged to cause practically no inflammatory or immunological reactions.

In particular, the RNA to be employed according to the invention is envisaged to have such low immunogenicity that the general condition of the patient is not affected. A slight increase in the aforesaid factors can thus be tolerated as long as the general condition does not worsen as a result.

Further properties of the (m)RNA to be employed according to the invention are its efficiency and stability. For this, transcription efficiency, transfection efficiency, translation efficiency and duration of protein expression are important and can be determined by methods known per se.

The transcription efficiency indicates how efficiently RNA can be produced from DNA. Here problems can arise with the use of a high content of modified nucleotides. The RNA modified according to the invention can be produced with high transcription efficiency.

A particular an RNA to be employed in accordance with the invention is an RNA which has (chemically) modified cytidine nucleotides and/or (chemically) modified uridine nucleotides. Such RNAs are described in, for example, WO 2011/012316.

Examples of suitable (chemical) modifications are set out in Table 4. A preferred modified cytidine is 5-methylcytidine (m5C). A preferred modified uridine is 2-thiouridine (s2U).

In particular, the cmRNA to be employed in accordance with the invention may be an RNA which has 5 to 50% of modified cytidine nucleotides and/or 5 to 50% of modified uridine nucleotides, and 50 to 95% of unmodified cytidine nucleotides and/or 50 to 95% of unmodified uridine nucleotides. The adenosine and guanosine nucleotides may be unmodified or partially modified, but they are preferably present in unmodified form. Preferably, 7.5 to 35% of the cytidine and/or uridine nucleotides are modified and, more preferably, the content of the modified cytidine nucleotides lies in a range from 15% to 25% and/or the content of the modified uridine nucleotides in a range from 15% to 25%.

One non-limiting example of a cmRNA to be employed in accordance with the invention is an RNA, wherein about 25% of the cytidines of said RNA are modified cytidines (e.g. 5-methylcytidines (m5C)) and/or about 25% of the uridines of said RNA are modified uridines (e.g. 2-thiouridines (s2U)) (m5C$_{(0.25)}$s2U$_{(0.25)}$ RNA). The respective adenosine and guanosine nucleotides are preferably present in unmodified form.

In another aspect, however, the RNA to be employed in accordance with the invention may also not be a cmRNA, i.e. the RNA may be a non-chemically modified RNA. As to this aspect, the non-chemically modified RNA may be a non-naturally or, preferably, naturally occurring RNA. It is particularly envisaged that the non-chemically modified RNA to be employed in the context of the invention comprises only non-modified, i.e. naturally occurring, nucleoside residues, namely naturally occurring adenosines, guanosines, cytidines and uridines. Other naturally occurring nucleosides may, in principle, also be comprised (e.g. inosines, thymidines, etc.). In particular, the RNA may not be a cmRNA as described above and, for example, may not be a cmRNA as described in WO 2011/012316. Even the non-chemically modified RNA to be employed in accordance with the invention may, however, have a reduced immunogenicity and, for example may abrogate (m)RNA interaction with Toll-like receptors and with retinoid-inducible gene I (RIG-I). Especially, when loaded onto a matrix or scaffold, i.e. carrier, in accordance with the invention and as described herein elsewhere, non-chemically modified RNA can advantageously be used. As such, also non-chemically modified RNA shows, for example, a prolonged lifetime. This renders the respective non-chemically modified RNA-loaded carrier a desirable depot for sustained/retarded RNA delivery. Another advantage of the non-chemically modified RNA is that a step of chemically modifying the RNA to be used is not required.

Hence, it is also envisaged in the context of the present invention that the pharmaceutical composition for use, the matrix or scaffold, i.e. carrier, and the pharmaceutical composition disclosed herein is formulated for sustained and/or retarded delivery of the RNA, in particular, of the non-chemically modified RNA to be employed in accordance with the invention. More particular, the pharmaceutical composition or matrix/scaffold may be formulated as a system, e.g. depot, for sustained and/or retarded delivery of the RNA. As described in more detail herein below, it is preferred also with respect to this aspect that the RNA is in form of a complex in accordance with the invention, that the matrix/scaffold is a collagen sponge which may be vacuum and/or freeze-fried and which has been loaded with the RNA.

In principle, the (m)RNA to be employed according to the invention may be used directly as such. However, there is also the possibility of (further) modifying the mRNA, for example in order to introduce (further) beneficial properties. Firstly, the mRNA may be modified by attaching other coding or non-coding sequences to the coding strand. Secondly, it may also be modified by binding further molecules to functional groups provided in the modified nucleotides.

In this context, the RNA to be employed according to the invention may have further functional regions and/or 3' or 5' noncoding regions. The 3' and/or 5' noncoding regions may be the regions naturally flanking the encoded protein (BMP) or else artificial sequences which contribute to the stabilization of the RNA. Those skilled in the art can discover the sequences suitable for this in each case by routine experiments.

In a preferred embodiment, the RNA contains an m7GpppG cap, an internal ribosome entry site (IRES) and/or a polyA tail at the 3' end, in particular in order to improve translation. The RNA can have further regions promoting translation.

What is essential is that the function of the BMP, or of the functional fragment thereof, treating, moderating or preventing a bone disease for which the (m)RNA is to be used can be provided.

In one embodiment, the (m)RNA to be employed may be combined with targeting ligands which bind to surface receptors specific for the target cells, so that a receptor-mediated transfection of the target cell is possible. For this purpose, firstly vehicles which are suitable for the introduction of (m)RNA into cells, or else, the (m)RNA itself may be modified with a ligand. Examples of suitable vehicles for the introduction of (m)RNA into cells are cationic agents. These include cationic lipids, cationic polymers or also nanoparticles, nanocapsules, magnetic nanoparticles and nanoemulsions. Suitable vehicles are known to those skilled in the art and described in the specialist literature. Suitable ligands are also well known to those skilled in the art and described in the literature and available. As ligands for example transferrin, lactoferrin, clenbuterol, sugar, uronic acids, antibodies, aptamers, etc. can be used. Examples of such vehicles and ligands are also described herein elsewhere.

As mentioned, the (m)RNA itself may be modified with a ligand. For this purpose, (m)RNAs with modified nucleosides that bear a primary amino group or an azido group in the 2' position of the ribose are preferred. Examples can be found in Table 4. Such modifications are particularly preferred since they contribute to the biological activity. Via these modifications, the ligand can easily be incorporated by amide formation or "click" chemistry, e.g. by bioconjugate techniques.

In a specific embodiment, an RNA sequence which can bind to proteins, e.g. receptors, (aptamer) is introduced at the 5' end of the (m)RNA. This procedure has the advantage that the ligand can already be introduced directly into the matrix at the DNA level and cloned and introduced into the (m)RNA by, e.g. in vitro translation (IVT). Hence subsequent modification of the (m)RNA with the ligand is no longer necessary.

In a further embodiment, the (m)RNA is modified by additional modification with inert polymers, e.g. polyethylene glycol (PEG). Methods for this are well known to those skilled in the art, and processes such as are known for ligands can be used. Thus for example a binding site for polyethylene glycol, to which the PEG is bound after transcription, can be provided in a small part of the modified nucleotides used for the (m)RNA. The polyethylene glycol serves for the extracellular stabilization of the (m)RNA, i.e. it protects the polyribonucleotide molecule until it has arrived in the cell. On entry into the cell, the PEG is cleaved off. Hence the bond between PEG and RNA is preferably designed such that the cleavage on entry into the cell is facilitated. For this, for example a functional group can be provided which is pH-dependently cleaved off. Other molecules stabilizing the RNA can also be provided via appropriate active sites on the modified nucleotides. In this way, the (m)RNA can be protected by steric stabilization against enzymatic degradation and an interaction with components of biofluids prevented. The (m)RNA thus modified can be designated as "stealth" (m)RNA.

A preferred method for the protection and stabilization of RNA is described in EP 11 98 489, to the content whereof reference is expressly made here. RNA to be employed according to the invention may be protected by the methods described in EP 11 98 489. It has been found that firstly the RNA can also advantageously be stabilized and protected by this method and secondly that the activity of RNA thus treated is not or not significantly restricted. Hence in a preferred embodiment of the present invention, the RNA is treated in accordance with EP 11 98 489.

In one embodiment, the RNA (mRNA, cmRNA etc.) to be employed in accordance with the invention may be encapsulated, i.e. comprised in a capsule. For example, the capsule may be a nanocapsule. Suitable capsules are known in the art and are also described herein elsewhere.

In one embodiment, the pharmaceutical composition of the invention further comprises one or more agent(s) or one or more reagent(s) for delivering and/or introducing the RNA into a target cell or a target tissue. In particular, it is envisaged that this/these agent(s) or reagent(s) support(s) the delivering and/or introducing the RNA into the cell or tissue. This/these agent(s) or reagent(s) may be administered together with the RNA. The RNA to be delivered/introduced may also be coupled with (e.g. covalently bound to or complexed with) or uncoupled with (for example only admixed with) this/these agent(s(or reagent(s). Respective agents or reagents are known in the art (e.g. Tavernier, J Control Release 150(3) (2011), 238-47) and are, for example, selected from the group consisting of lipids and liposomes, micelles, polymers and dendrimers, among others. Particular examples of respective agents or reagents are DOTAP (1,2-dioleyl-3-trimethylammonium propane), DODAP (1,2-dioleyl-3-dimethylammonium propane), DOTMA (1,2-di-O-octadecenyl-3-trimethylammonium propane), XTC (2,2-Dilinoleyl-4-dimethylaminoethyl-[1,3]-dioxolane) and MC3 (((6Z,9Z,28Z,31Z)-heptatriaconta-6,9,28,31-tetraen-19-yl 4-(dimethylamino)butanoate), ALNY-100 ((3 aR,5s,6aS)—N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-NI,N16-diundecyl-4,7,10,13-tetraazahexadecane-I, 16-diamide), C12-200, DLin-KC2-DMA, DODAP, 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxy ethyl ammonium bromide or "DMRIE", 3-dimethylamino-2-(cholest-5-en-3-beta-oxybutan-4-oxy)-I-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[I,3]-dioxolane or "DLin-K-DMA", 2,2-dilinoleyl-4-dimethylaminoethyl-[1,3]-dioxolane or "DLin-K-XTC2-DMA", or mixtures thereof (Heyes, J Controlled Release 107 (2005), 276-287; Morrissey, Nat. Biotechnol. 23(8) (2005), 1003-1007; WO2005/121348). Further examples are DC-Chol (N,N-dimethyl-N-ethylcarboxamidocholesterol), I,4-bis(3-N-oleylaminopropyl)piperazine (Gao, Biochem. Biophys. Res. Comm. 179 (1991), 280; Wolf, et al BioTechniques 23 (1997), 139; U.S. Pat. No. 5,744,335). Further examples are LIPOFECTIN (DOTMA:DOPE) (Invitrogen, Carlsbad, Calif), LIPOFECTAMINE (DOSPA:DOPE) (Invitrogen), LIPOFECTAMINE2000. (Invitrogen), FUGENE, TRANSFECTAM (DOGS), and EFFECTENE. Further examples are modified and unmodified polyacrylates, polyalkycyanoacrylates, polylactide, polylactide-polyglycolide copolymers, polycaprolactones, dextran, albumin, gelatin, alginate, collagen, chitosan, cyclodextrins, polylysin, polyarginine, oligo/polyamines and polyethylenimine.

The agents or reagents may be oligomers, polymers or lipidoids. They may comprise oligo(alkylene amine) moieties like, for example, the characteristic oligo(alkylene amine) moieties as described in PCT/EP2014/063756. In particular, the agents or reagents may be the oligomers, polymers or lipidoids as described in PCT/EP2014/063756.

One main characteristic of these particular agents or reagents is that they contain a following common structural entity of formula (I):

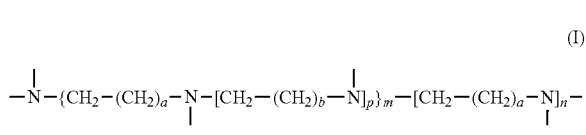

Such agents or reagents may be (a component comprising) an oligo(alkylene amine) selected from:

a) an oligomer or polymer comprising a plurality of groups of formula (II) as a side chain and/or as a terminal group:

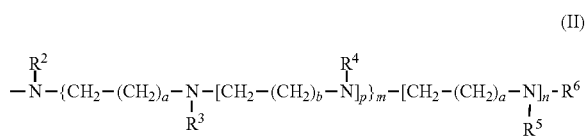

wherein the variables a, b, p, m, n and $R^2$ to $R^6$ are defined as follows, independently for each group of formula (II) in a plurality of such groups:

a is 1 and b is an integer of 2 to 4; or a is an integer of 2 to 4 and b is 1, p is 1 or 2, m is 1 or 2; n is 0 or 1 and m+n is $\geq 2$; and $R^2$ to $R^5$ are, independently of each other, selected from hydrogen; a group $-CH_2-CH(OH)-R^7$, $-CH(R^7)-CH_2-OH$, $-CH_2-CH_2-(C=O)-O-R^7$, $-CH_2-CH_2-(C=O)-NH-R^7$ or $-CH_2-R^7$ wherein $R^7$ is selected from C3-C18 alkyl or C3-C18 alkenyl having one C=C double bond; a protecting group for an amino group; and a poly(ethylene glycol) chain;

$R^6$ is selected from hydrogen; a group $-CH_2-CH(OH)-R^7$, $-CH(R^7)-CH_2-OH$, $-CH_2-CH_2-(C=O)-O-R^7$, $-CH_2-CH_2-(C=O)-NH-R^7$ or $-CH_2-R^7$ wherein $R^7$ is selected from C3-C18 alkyl or C3-C18 alkenyl having one C=C double bond; a protecting group for an amino group; $-C(NH)-NH_2$; a poly(ethylene glycol) chain; and a receptor ligand, and wherein one or more of the nitrogen atoms indicated in formula (II) may be protonated to provide a cationic group of formula (II);

b) an oligomer or polymer comprising a plurality of groups of formula (III) as repeating units:

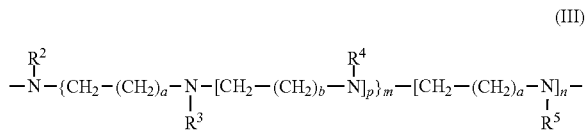

wherein the variables a, b, p, m, n and $R^2$ to $R^5$ are defined as follows, independently for each group of formula (III) in a plurality of such groups:

a is 1 and b is an integer of 2 to 4; or a is an integer of 2 to 4 and b is 1, p is 1 or 2, m is 1 or 2; n is 0 or 1 and m+n is $\geq 2$; and $R^2$ to $R^5$ are, independently of each other, selected from hydrogen; a group —$CH_2$—$CH(OH)$—$R^7$, —$CH(R^7)$—$CH_2$—$OH$, —$CH_2$—$CH_2$—$(C=O)$—$O$—$R^7$ or —$CH_2$—$CH_2$—$(C=O)$—$NH$—$R^7$ or —$CH_2$—$R^7$ wherein $R^7$ is selected from C3-C18 alkyl or C3-C18 alkenyl having one C=C double bond; a protecting group for an amino group; —$C(NH)$—$NH_2$; and a poly(ethylene glycol) chain;

and wherein one or more of the nitrogen atoms indicated in formula (III) may be protonated to provide a cationic group of formula (III); and c) a lipidoid having the structure of formula (IV):

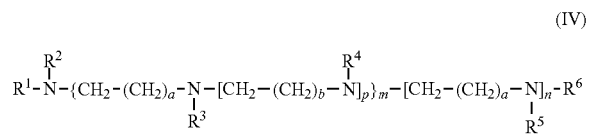

(IV)

wherein the variables a, b, p, m, n and $R^1$ to $R^6$ are defined as follows:

a is 1 and b is an integer of 2 to 4; or a is an integer of 2 to 4 and b is 1, p is 1 or 2, m is 1 or 2; n is 0 or 1 and m+n is ≥2; and $R^1$ to $R^6$ are independently of each other selected from hydrogen; a group —$CH_2$—$CH(OH)$—$R^7$, —$CH(R^7)$—$CH_2$—$OH$, —$CH_2$—$CH_2$—$(C=O)$—$O$—$R^7$, —$CH_2$—$CH_2$—$(C=O)$—$NH$—$R^7$ or —$CH_2$—$R^7$ wherein $R^7$ is selected from C3-C18 alkyl or C3-C18 alkenyl having one C=C double bond; a protecting group for an amino group; —$C(NH)$—$NH_2$; a poly(ethylene glycol) chain; and a receptor ligand; provided that at least two residues among $R^1$ to $R^6$ are a group —$CH_2$—$CH(OH)$—$R^7$, —$CH(R^7)$—$CH_2$—$OH$, —$CH_2$—$CH_2$—$(C=O)$—$O$—$R^7$, —$CH_2$—$CH_2$—$(C=O)$—$NH$—$R^7$ or —$CH_2$—$R^7$ wherein $R^7$ is selected from C3-C18 alkyl or C3-C18 alkenyl having one C=C double bond;

and wherein one or more of the nitrogen atoms indicated in formula (IV) may be protonated to provide a cationic lipidoid of formula (IV).

In a more specific aspect, such agents or reagents may be (a component comprising) an oligo(alkylene amine) selected from a) and b), wherein a) is an oligomer or polymer comprising a plurality of groups of formula (IIa) as a side chain and/or as a terminal group:

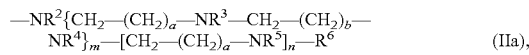

(IIa), wherein a, b, m, n, and $R^2$ to $R^6$ are defined as described above, and wherein one or more of the nitrogen atoms indicated in formula (IIa) may be protonated to provide a cationic oligomer or polymer structure; and b) is an oligomer or polymer comprising a plurality of groups of formula (IIIa) as repeating units:

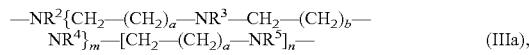

(IIIa), wherein a, b, m, n, and $R^2$ to $R^5$ are defined as described above, and wherein one or more of the nitrogen atoms indicated in formula (IIIa) may be protonated to provide a cationic oligomer or polymer structure.

In a another more specific aspect, such agents or reagents may be (a component comprising) an oligo(alkylene amine) selected from a lipidoid having the structure of formula (IVa):

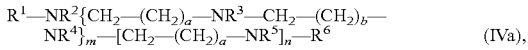

(IVa), wherein a, b, m, n, and $R^1$ to $R^6$ are defined as described above, and wherein one or more of the nitrogen atoms indicated in formula (IVa) may be protonated to provide a cationic lipidoid.

As to such agents or reagents, in formula (II), (IIa), (III), (IIIa), (IV) or (IVa) n may be 1; or m may be 1 and n may be 1.

Further, as to such agents or reagents, in formula (II), (IIa), (III), (IIIa), (IV) or (IVa) a may be 1 and b may be 2; or a may be 2 and b may be 1.

In one particular aspect, the oligomer, polymer or lipidoid may be a cationic (e.g. protonated) oligomer, polymer or lipidoid.

One non-limiting example of such an oligomer, polymer or lipidoid to be employed in the context of the invention is a cationic lipid which was prepared by mixing 100 mg N,N'-Bis(2-aminoethyl)-1,3-propanediamine (0.623 mmol) with 575.07 mg 1,2-Epoxydodecane (3.12 mmol, (N−1) eq. where N is 2× amount of primary amine plus 1× amount secondary amine per oligo(alkylene amine)) and mixed for 96 h at 80° C. under constant shaking. Such an oligomer, polymer or lipidoid is also referred to as lipidoid "C12-(2-3-2)".

An agent or reagent, in particular a polymer, to be employed in accordance with the invention may be a copolymer, in particular a statistical copolymer. Such a copolymer may be a copolymer which contains a statistical/random arrangement of alkylene amine repeating units of alternating length (e.g. in contrast to a less preferred polymer which contains analogous arrangements of alkylene amine repeating units of non-alternating length). The copolymer may be a cationic (e.g. protonated) copolymer. Copolymers to be employed in accordance with the invention are known in the art and are, for example, described in EP 14 19 9439.2, WO 01/00708, EP-A1 1 198 489 and CA-A1 2,377,207.

In particular, the copolymer may be a statistical copolymer comprising a plurality of repeating units (a) independently selected from repeating units of the following formulae (a1) and (a2):

(a1)

(a2)

and a plurality of repeating units (b) independently selected from repeating units of the following formulae (b1) to (b4):

(b1)

(b2)

(b3)

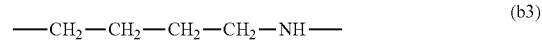

(b4)

wherein the molar ratio of the sum of the repeating units (a) to the sum of the repeating units (b) lies within the range of 0.7/1.0 to 1.0/0.7, and wherein one or more of the nitrogen atoms of the repeating units (a) and/or (b) contained in the copolymer may be protonated to provide a cationic copolymer.

The copolymer may be a statistical copolymer, wherein any repeating units (a) and any repeating units (b) are statistically distributed in the copolymer macromolecule. It is typically obtained from the copolymerization of a mixture of monomers yielding, during the polymerization reaction, the repeating units (a) with monomers yielding, during the polymerization reaction, the repeating units (b). Preferably, the copolymer is a random copolymer wherein any repeating units (a) and any repeating units (b) are randomly distributed in the polymer macromolecule.

The copolymer in accordance with the invention can be a linear, branched or dendritic copolymer. As will be understood by the skilled reader, a repeating unit of the formula (a1), (b1) or (b3) with two valencies (i.e. open bonds to neighboring units) leads to a propagation of the copolymer structure in a linear manner. Thus, a linear copolymer of the invention comprises repeating units of formula (a1) and one or more types of the repeating units of formulae (b1) and (b3), but no repeating units of formula (a2), (b2) or (b4). As will be further understood, the presence of a repeating unit of formula (a2), (b2) or (b4) with three valencies provides a branching point in the copolymer structure. Thus, a branched copolymer comprises one or more types of the repeating units of formulae (a2), (b2) and (b4), and may further comprise one or more types of the repeating units of formulae (a1), (b1) and (b3).

The copolymer in accordance with the invention comprises a plurality of repeating units (a) independently selected from repeating units of formulae (a1) and (a2) defined above, and a plurality of repeating units (b) independently selected from repeating units of formulae (b1) to (b4) defined above. Preferred are copolymers comprising a plurality of repeating units (a) independently selected from repeating units of formulae (a1) and (a2) defined above, and a plurality of repeating units (b) independently selected from repeating units of formulae (b1) and (b2) defined above.

It is also preferred that the copolymer in accordance with the invention is a branched copolymer comprising one or more types of repeating units selected from repeating units (a2), (b2) and (b4), and which optionally further comprises one or more types of the repeating units of formulae (a1), (b1) and (b3), and in particular a copolymer which comprises repeating units of the formula (a2) and one or more type of the repeating units of formulae (b2) and (b4), and which optionally further comprises one or more types of the repeating units of formulae (a1), (b1) and (b3). In line with the above, a more preferred copolymer is thus a branched copolymer which comprises repeating units of the formula (a2) and repeating units of formula (b2), and which optionally further comprises one or more types of the repeating units of formulae (a1) and (b1).

In the copolymers in accordance with the invention, the total number of the repeating units (a) and repeating units (b) is typically 20 or more, preferably 50 or more and more preferably 100 or more. Typically, the total number of the repeating units (a) and repeating units (b) is 10,000 or less, preferably 5,000 or less, more preferably 1,000 or less.

Furthermore, it is preferred for the copolymers in accordance with the invention that the repeating units (a) and (b) account for 80 mol % or more, more preferably 90 mol % or more of all repeating units in the copolymer. Further preferred are copolymers wherein repeating units (a) selected from (a1) and (a2) and repeating units (b) selected from (b1) and (b2) account for 80 mol % or more, more preferably 90 mol % or more of all repeating units in the copolymer. It is most preferred that all of the repeating units in the copolymer are repeating units (a) or (b), in particular that all of the repeating units in the copolymer are repeating units (a) selected from (a1) and (a2) or repeating units (b) selected from (b1) and (b2).

The weight average molecular weight of the copolymer in accordance with the present invention, as measured e.g. via size exclusion chromatography relative to linear poly(ethylene oxide) standards, generally ranges from 1,000 to 500,000 Da, preferably from 2,500 to 250,000 Da and more preferably 5,000-50,000 less.

The terminal groups of the copolymer in accordance with the invention typically comprise one or more types of groups (c) independently selected from groups of the formulae (c1) to (c3) below, preferably from groups of the formulae (c1) and (c2) below:

  (c1)

  (c2)

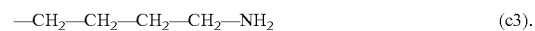  (c3).

Preferably, the terminal groups in the copolymer consist of one or more types of groups (c) independently selected from groups of the formulae (c1) to (c3) below, preferably from groups of the formulae (c1) and (c2). As will be understood by the skilled person, the number of terminal groups depends on the structure of the copolymer in accordance with the invention. While a linear copolymer has only two terminals, larger numbers of terminal groups are contained in a branched, in particular in a dendritic copolymer. As will be further understood, also one or more of the nitrogen atoms of the terminal groups (c) contained in the copolymer may be protonated to provide a cationic copolymer.

In the copolymer in accordance with the invention, the molar ratio of the sum of the repeating units (a) to the sum of the repeating units (b) lies within the range of 0.7/1.0 to 1.0/0.7, and preferably within the range of 0.8/1.0 to 1.0/0.8. This molar ratio can be determined, e.g., via NMR. It will thus be understood that the ratio is usually determined for a plurality of macromolecules of the copolymer in accordance with the invention, and typically indicates the overall ratio of the sum of repeating units (a) to the sum of repeating units (b) in the plurality of macromolecules.

As indicated above, one or more of the nitrogen atoms of the copolymer in accordance with the invention may be protonated to result in a copolymer in a cationic form, typically an oligocationic or polycationic form. It will be understood that the primary, secondary, or tertiary amino groups in the repeating units (a) or (b) or in the terminal groups (c) can act as proton acceptors, especially in water and aqueous solutions, including physiological fluids. Thus, the copolymers of the present invention typically have an overall positive charge in an aqueous solution at a pH of below 7.5. An aqueous solution, as referred to herein, is a solution wherein the solvent comprises 50% (vol./vol.) or more, preferably 80 or 90% or more, and most preferably 100% of water. Also, if the compositions in accordance with the invention are in contact with a physiological fluid having a pH of below 7.5, including e.g. blood and lung fluid, they typically contain repeating units (a) and (b) wherein the nitrogen atoms are protonated. The $pK_a$ values of the copolymers used in the compositions in accordance with the invention can be determined by acid-base titration using an automated $pK_a$ titrator. The net charge at a given pH value can then be calculated e.g. from the Henderson-Hasselbach equation. Any charge may be shared across several of the basic centres and cannot necessarily be attributed to a single point. Typically, in solutions at physiological pH, the copolymers used in the compositions in accordance with the invention comprise repeating units with amino groups in protonated state and repeating units with amino groups in unprotonated state.

However, as will be understood by the skilled reader, the copolymers in accordance with the invention as well as the compositions in accordance with the invention may also be provided as a dry salt form which contains the copolymer in a cationic form.

As will be further understood, counterions (anions) for the positive charges of protonated amino groups in compositions according to the invention comprising the copolymer and nucleic acid, in particular RNA, preferably single-stranded RNA such as mRNA, are typically provided by anionic moieties contained in the nucleic acid. If the positively charged groups are present in excess compared to the anionic moieties in the nucleic acid, positive charges may be balanced by other anions, in particular those typically encountered in physiological fluids, such as $Cl^-$ or $HCO_3^-$.

In line with the above, a preferred copolymer in accordance with the invention is a random copolymer, wherein
80 mol % or more of all repeating units, more preferably all repeating units, are formed by
a plurality of repeating units (a) independently selected from repeating units of the following formulae (a1) and (a2):

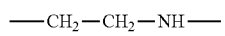  (a1)

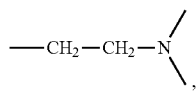  (a2)

and
a plurality of repeating units (b) independently selected from repeating units of the following formulae (b1) and (b2):

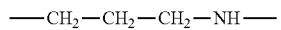  (b1)

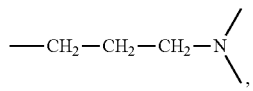  (b2)

wherein the molar ratio of the sum of the repeating units (a) to the sum of the repeating units (b) lies within the range of 0.7/1.0 to 1.0/0.7, more preferably within the range of 0.8/1.0 to 1.0/0.8;
wherein the terminal groups of the copolymer are formed by
groups (c) independently selected from groups of the formulae (c1) and (c2):

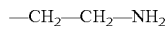  (c1)

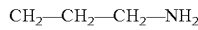  (c2); and wherein one or more of the nitrogen atoms of the repeating units (a) and/or (b) and/or of the terminal groups (c) contained in the copolymer may be protonated to provide a cationic copolymer. It is further preferred that the copolymer is a branched copolymer, comprising units (a2) and (b2), optionally together with units (a1) and/or (b1).

The copolymers in accordance with the invention can be conveniently prepared with procedures analogous to those known for the preparation of polyalkyleneimines, such as branched or linear polyethyleneimine (PEI). It will be understood that the monomers used for the production of the copolymers will have to be adjusted accordingly. In the context of the present invention, it has been found that the monomers can be conveniently reacted in a quantitative manner, such that the ratio of the units (a) and (b) in the copolymer can be adjusted by adjusting the monomer ratio accordingly in the monomer mixture subjected to polymerization. While polyethyleneimine can be prepared e.g. via ring-opening polymerization of aziridine, the copolymers in accordance with the invention can be prepared via ring opening polymerization of a monomer mixture comprising or consisting of aziridine, azetidine and, where applicable pyrrolidine, or, in preferred embodiments, of aziridine and azetidine. It will be understood that the expression "where applicable" refers to the presence or absence of repeating units (b3) and (b4) or terminal groups (c3) which would be formed by the pyrrolidine. The ring opening polymerization of the non-substituted cyclic amines usually leads to branched copolymers. Linear copolymers in accordance with the invention can be prepared, e.g., via polymerization of suitable N-substituted aziridines, N-substituted azetidines and N-substituted pyrrolidines, or N-substituted aziridines and N-substituted azetidines, which may be followed e.g. by a hydrolytic cleavage of N-substituents attached to the resulting polyalkyleneimine chain, e.g. in analogy to the procedure published in Katrien F. Weyts, Eric J. Goethals, New synthesis of linear polyethyleneimine, Polymer Bulletin, January 1988, Volume 19, Issue 1, pp 13-19.

For the preparation of a dendrimer (or dendritic copolymer), synthetic strategies can be analogously applied which are known for the production of polyethyleneimine or polypropyleneamine dendrimers. Polypropylenimine dendrimers can be synthesized from acrylonitrile building blocks using a repetitive sequence of a Michael addition to a primary amine, followed by a heterogeneously catalyzed hydrogenation (Newkome and Shreiner Poly(amidoamine), polypropylenimine, and related dendrimers and dendrons possessing different 1-42 branching motifs: An overview of the divergent procedures. Polymer 49 (2008) 1-173; De Brabander-Van Den Berg et al. Large-scale production of polypropylenimine dendrimers, Macromolecular Symposia (1994) 77 (1) 51-62). Polyethylenimine dendrimers can be produced using a repetitive sequence of a Michael addition of a vinyl bromide building block to a primary amine followed by a conversion of alkylbromide to amine using a Gabriel amine synthesis method (Yemul & Imae, Synthesis and characterization of poly(ethyleneimine) dendrimers, Colloid Polym Sci (2008) 286:747-752). Hence the person skilled in the art will be able to produce not only dendrimers with strictly alternating layers of e.g. propylenimine and ethylenimine can be produced. Similarly dendrimer generations with layers comprising or consisting of random compositions of repeating units of formula (a2), (b2) and (b4) and preferably repeating units (a2) and (b2) can be generated.

The ring opening polymerization of aziridine and azetidine, or of aziridine, azetidine and pyrrolidine, can be carried out in solution, e.g. in water. The total monomer concentration is not particularly limited, typical concentrations range from 10% wt/wt to 80% wt/wt, preferably 30% wt/wt to 60% wt/wt. Typically, the polymerization is initiated by protons, such that it is preferred to add a Brønsted acid, in particular a mineral acid such as sulphuric acid to the reaction system. Small amounts of acid are generally sufficient, such as 0.001 to 0.01 equivalents, based on the total concentration of monomers. The reaction proceeds at convenient rates e.g. in the temperature range of 50 to 150° C., in particular 90 to 140° C. In these ranges, higher molecular weight copolymers are usually at higher temperatures, and lower molecular weight copolymers at lower temperatures.

In principle, a lipidoid is a preferred agent or reagent to be employed in accordance with the invention, in particular as compared to an oligomer and, more particular particular, to a polymer.

Further examples of the one or more agent(s) or one or more reagent(s) for delivering and/or introducing the RNA into a target cell or a target tissue are the liposomal transfection reagents (LTR'S) and magnetic particles (MPs) as described herein elsewhere.

One particular mode for delivering and/or introducing the RNA into target cells or target tissue is transfection. Hence, in one aspect, the RNA to be employed is envisaged to be transfected (into (target) cells or tissue), to be delivered/administered via transfection and/or to be prepared for transfection. Means and methods for transfecting RNA are well known in the art and are, for example, described in Tavernier (loc. cit.), Yamamoto (Eur J Pharm Biopharm. 71(3) (2009), 484-9) and Kormann (Nat Biotechnol. 29(2) (2011), 154-7).

Particular modes of transfection are lipofection, magnetofection or magnetolipofection. In the context of the invention good results have been achieved with these kind of transfections. The results were particularly good with magnetofection and extraordinary good with magnetolipofection.

Hence, in one aspect, the RNA to be employed may be prepared for lipofection, prepared to be transfected by lipofection, delivered/introduced via lipofection and/or administered via lipofection.

In accordance with this aspect, the pharmaceutical composition of the invention may (further) comprise at least one lipid or liposomal transfection reagent or enhancer (LTR; liposomal transfection reagent). The RNA to be employed may be comprised in, complexed with and/or delivered by the LTR. In particular, the RNA to be employed may be comprised in and/or delivered by (respective) lipofection complexes comprising the RNA and the LTR. The pharmaceutical composition of the invention may (further) comprise the lipofection complexes.

LTRs are known in the art and are, for example, distributed by OzBiosciences, Marseille, France. LTRs to be employed according to the invention may be selected from the group consisting of the above-described agents or reagents for delivering and/or introducing the RNA into a target cell or a target tissue. For example, such LTRs may be lipids or lipidoids, preferably cationic lipids or cationic lipidoids, like the lipidoids as disclosed in PCT/EP2014/063756 (e.g. C12-(2-3-2), the lipids as disclosed in EP2285772 (e.g. Dogtor) and the lipopolyamines as disclosed in EP1003711 (e. g. DreamFect™ and DreamFect Gold™). A particular LTR may be selected from the group consisting of (i) C12-(2-3-2);
(ii) DreamFect™, preferably DreamFect Gold™ (DF™/DF-Gold™; OzBiosciences, Marseille, France);
(iii) Dogtor (OzBiosciences, Marseille, France); and
(iv) Lipofectamine like, for example, Lipofectamine 2000 (Invitrogene, CA, USA).

In principle, Dogtor is a preferred, DreamFect™ is a more preferred and DF-Gold™ and C12-(2-3-2) are even more preferred LTR(s).

LTRs like Dogtor are, for example, described in EP2285772. LTRs like DF™ or DF-Gold™ are, for example, described in EP1003711. In principle, the oligomers, polymers or lipidoids as disclosed in PCT/EP2014/063756, the particular cationic lipids as disclosed in EP2285772 and the particular lipopolyamines as disclosed in EP1003711 are preferred LTRs in accordance with the invention. LTRs like C12-(2-3-2) and DF-Gold™ are most preferred.

Non-limiting examples of lipofection complexes are DF-Gold™/RNA lipoplexes and C12-(2-3-2)/RNA lipoplexes.

The herein described agents and reagents for delivering and/or introducing the RNA into a target cell or a target tissue and the herein described LTRs may be combined with one or more (e.g. two, three or four) further lipid(s) (like, for example, cholesterol, DOPE and/or PEG-lipids (e.g. DMPE-PEG)). These further lipids may support the desired function of the agents/reagents and LTRs (support and/or increase the delivering and/or introducing of RNA into the cell or tissue and improve transfection efficiency, respectively) and function as respective "helper lipids". Particular examples of such "helper lipids" are cholesterol, DPPC, DOPE and/or PEG-lipids (e.g. DMPE-PEG, DMG-PEG (e.g. DMG-PEG2k). The further lipids (e.g. "helper lipids") may also be part(s) of the herein disclosed complexes/particles. The skilled person is readily in the position to prepare complexes/particles in accordance with the invention. Examples of further lipids (e.g. "helper lipids") are also known in the art. The skilled person is readily in the position to choose suitable further lipids (e.g. "helper lipids") and ratios of the agents/reagents/LTRs and the further lipids (e.g. "helper lipids"). Such ratios may be molar ratios of 1-4:1-5, 3-4:4-6, about 4:about 5, about 4:about 5.3 of agents/reagents/LTRs: further lipid(s) (the more narrow ranges are preferred). For example, the agents/reagents/LTRs may be combined with three further lipids, like cholesterol, DOPE and DMPE-PEG, at a molar ratio of 8:5.3:4.4:0.9, respectively, or, more particular, 8:5.29:4.41:0.88, respectively.

In another aspect, the RNA to be employed may be prepared for magnetofection, prepared to be transfected by magnetofection, delivered/introduced via magnetofection and/or administered via magnetofection. The principles of magnetofection are known in the art and are, for example, described in WO 02/00870.

In accordance with this aspect, the pharmaceutical composition of the invention may (further) comprise at least one kind of magnetic particles (MPs), in particular at least one kind of magnetic nanoparticles (MNPs). The RNA to be employed may be comprised in, complexed with and/or delivered by the MP. In particular, the RNA to be employed may be comprised in and/or delivered by (respective) magnetofection complexes comprising the RNA and the MP. The pharmaceutical composition of the invention may (further) comprise the magnetofection complexes.

The MPs (or MNPs) to be employed may be core-shell MPs, iron oxide silica MPs, and/or (branched)PEI-decorated MPs. Particular MPs (or MNPs) may be MPs (or MNPs) with a SiOx/Phosphonate-PEI coating, further referred to as SO-Mag6-115 MPs (or MNPs). MPs (or MNPs) may be produced according to the appended examples and, for example, according to Mykhaylyk (Liposomal magnetofection. In: Weissig V (ed.) Liposomes, Methods in Molecular Biology, vol. 605. Humana Press-Springer, New York 2010, 487-525; Pharm Res 29(5), 2012, 1344-1365).

One non-limiting example of a magnetofection complex is a SO-Mag6-115 MPs (or MNPs)/RNA magnetofection complex. Further MP (or MNPs), and respective magnetofection complexes are described in WO 02/00870.

In a more specific aspect, the magnetofection complex may comprise a third component and may, hence, be in the form of magnetic triplexes. The third component may be an LTR (for example as defined herein above). The magnetic triplexes may then be named magnetolipofection complexes and may, for example, magnetolipofection complexes as defined herein below.

In yet another, more specific aspect, the RNA to be employed may be prepared for magnetolipofection, prepared to be transfected by magnetolipofection, delivered/introduced via magnetolipofection and/or administered via magnetolipofection.

In principle, magnetolipofection combines lipofection and magnetofection and, in particular, the advantages of both transfection approaches. Hence, in principle what has been said herein above with respect to lipofection and magnetofection also applies to magnetolipofection, mutatis mutandis.

According to the aspect of magnetolipofection, the pharmaceutical composition of the invention may (further) comprise at least one kind of a magnetolipofection complex (also named magnetic lipoplex). The RNA to be employed may be comprised in, complexed with and/or delivered by such a complex. The magnetolipofection complex may be a magnetic triplex and may, for example, comprise the RNA, at least one kind of an MP (as defined herein above) and at least one kind of an LTR (as defined herein above).

One non-limiting example of a magnetolipofection complex is a SO-Mag6-115 MPs (or MNPs)/DF-Gold/RNA magnetolipofection complex.

In principle, suitable ratios between the components (e.g. RNA, LTRs, MPs) of the transfection complexes to be employed in accordance with the invention can readily be determined by the skilled person. Respective guidance is provided in, for example, Kormann (loc. cit.), Mays (loc. cit.), WO 02/00870 and in the appended examples.

However, as mentioned, it was found out in the context of the invention that particular ratios are extraordinary useful, e.g. result in highly effective and/or efficient transfection.

Such particular ratios are w/w ratios of the LTR to the RNA ranging from approximately 1 to 40 µg, 5 to 35 µg, 10 to 30 µg, 15 to 25 µg, 17 to 23 µg, 18 to 22 µg, 19 to 21 µg, 1 to 20 µg, 2 to 20 µg, 3 to 20 µg, 1 to 15 µg, 2 to 15 µg, 3 to 15 µg, 1 to 10 µg, 2 to 10 µg, 3 to 10 µg, 4 to 10 µg, 5 to 10 µg, 4 to 12 µg, 5 to 11 µg, 6 to 10 µg or 7 to 9 µg of said LTR per µg of said RNA. Likewise, in particular if the LTRs are prepared as an LTR solution (e.g. as in the appended examples), such ratios are v/w ratios of the LTR solution to the RNA ranging from 0.5 to 15 µl, 0.5 to 10 µl, 0.5 to 8 µl, 1 to 15 µl, 1 to 10 µl, 1 to 8 µl, 1 to 6 µl, 1.5 to 5.5 µl, 2 to 5 µl, 3 to 4 µl, 1 to 3 µl, 4 to 6 µl, 1.5 to 2.5 µl, 4.5 to 5.5 µl, 1.7 to 2.3 µl or 4.7 to 5.3 µl of said LTR solution per µg of said RNA. In principle, the narrower ranges are preferred. In this context, a preferred LTR is DreamFect™ or, more preferred, DF-Gold™ or C12-(2-3-2). A preferred RNA is BMP-7 RNA or, more preferred, BMP-2 RNA.

Further particular ratios of LTR to the RNA are N/P ratios of about 4 to 12, preferably about 6 to 10, preferably about 9 to 11 and more preferably about 8, wherein N/P stands for the molar-ratio of the amino group of the LTR to the phosphate group of the RNA.

In particular, if cells like adipose-derived mesenchymal stem cells (AMSCs) are to be transfected, such particular ratios are w/w ratios of the LTR to the RNA ranging from approximately 5 to 35 µg, 10 to 30 µg, 15 to 25 µg, 17 to 23 µg, 18 to 22 µg or 19 to 21 µg of said LTR per µg of said RNA. Likewise, in particular if the LTRs are prepared as an LTR solution (e.g. as in the appended examples), such particular ratios are v/w ratios of the LTR solution to the RNA ranging from 4 to 6 µl, 4.5 to 5.5 µl or 4.7 to 5.3 µl of said LTR solution per µg of said RNA. In principle, the narrower ranges are preferred. Most preferred ratios (resulting in highly effective and efficient transfection of AMSCs) are w/w ratios of the LTR to the RNA of about 20 µg of said LTR per µg of said RNA and/or v/w ratios of the LTR solution to the RNA of about 5 µl of said LTR solution per µg of said RNA. What has been said above with respect to the preferred LTR and/or RNA also applies here, mutatis mutandis.

In particular, if cells like bone marrow-derived MSCs (BMSCs) are to be transfected, such particular ratios are w/w ratios of the LTR to the RNA ranging from approximately 4 to 12 µg, 5 to 11 µg, 6 to 10 µg or 7 to 9 µg of said LTR per µg of said RNA. Likewise, in particular if the LTRs are prepared as an LTR solution (e.g. as in the appended examples), such particular ratios are v/w ratios of the LTR solution to the RNA ranging from 1 to 3 µl, 1.5 to 2.5 µl or 1.7 to 2.3 µl of said LTR solution per µg of said RNA. In principle, the narrower ranges are preferred. Most preferred ratios (resulting in highly effective and efficient transfection of BMSCs) are w/w ratios of the LTR to the RNA of about 8 µg of said LTR per µg of said RNA and/or v/w ratios of the LTR solution to the RNA of about 2 µl of said LTR solution per µg of said RNA. What has been said above with respect to the preferred LTR and/or RNA also applies here, mutatis mutandis.

Further such particular ratios are iron w/w ratios of the MPs to the RNA ranging from 0.05 to 5 µg, 0.05 to 3 µg, 0.05 to 1 µg, 0.07 to 5 µg, 0.1 to 5 µg, 0.1 to 1 µg, 0.2 to 0.8 µg, 0.3 to 0.7 µg or 0.4 to 0.6 µg (iron weight) of said MPs per µg of said RNA. In principle, the narrower ranges are preferred. Most preferred ratios are iron w/w ratios of the MPs to the RNA of about 0.5 µg of said MPs per µg of said RNA. In this context, preferred MPs are SO-Mag6-115 MPs (or, more preferred, MNPs). A preferred RNA is BMP-7 or, more preferred, BMP-2 RNA.

Further such particular ratios are iron w/w ratios of the MPs to the LTR ranging from approximately 0.05 to 5 µg, 0.05 to 3 µg, 0.05 to 1 µg, 0.07 to 5 µg, 0.1 to 5 µg, 0.1 to 1 µg, 0.2 to 0.8 µg, 0.3 to 0.7 µg or 0.4 to 0.6 µg (iron weight) of said MPs per about 12 to 20 µg (preferably per about 16 µg) of said LTR. Likewise, in particular if the LTRs are prepared as LTR solutions (e.g. as in the appended examples), such ratios are iron w/v ratios of the MPs to the LTR solution ranging from 0.05 to 5 µg, 0.05 to 3 µg, 0.05 to 1 µg, 0.07 to 5 µg, 0.1 to 5 µg, 0.1 to 1 µg, 0.2 to 0.8 µg, 0.3 to 0.7 µg or 0.4 to 0.6 µg (iron weight) of said MPs per 4 µl of said LTR solution. In principle, the narrower ranges are preferred. Most preferred ratios are iron w/w ratios of the MPs to the LTR of about 0.5 µg of said MPs per about 12 to 20 µg (preferably per about 16 µg) of said LTR and/or iron w/v ratios of the MPs to the LTR solution of about 0.5 µg of said MPs per 4 µl of said LTR solution. In this context, preferred MPs are SO-Mag6-115 MPs (or, more preferred, MNPs). A preferred LTR is DreamFect™ or, more preferred, DF-Gold™ C12-(2-3-2).

Further, such particular ratios are iron w/w/w ratios of the MPs to the LTR to the RNA ranging from 0.05 to 5 μg, 0.05 to 3 μg, 0.05 to 1 μg, 0.07 to 5 μg, 0.1 to 5 μg, 0.1 to 1 μg, 0.2 to 0.8 μg, 0.3 to 0.7 μg or 0.4 to 0.6 μg (iron weight) of said MPs: 1 to 40 μg, 5 to 35 μg, 10 to 30 μg, 15 to 25 μg, 17 to 23 μg, 18 to 22 μg, 19 to 21 μg, 1 to 20 μg, 2 to 20 μg, 3 to 20 μg, 1 to 15 μg, 2 to 15 μg, 3 to 15 μg, 1 to 10 μg, 2 to 10 μg, 3 to 10 μg, 4 to 10 μg, 5 to 10 μg, 4 to 12 μg, 5 to 11 μg, 6 to 10 μg or 7 to 9 μg of said LTR: 0.1 to 10 μg, 0.1 to 7 μg, 0.1 to 4 μg, 0.4 to 10 μg, 0.7 to 10 μg, 0.7 to 4 μg, 0.8 to 3 μg, 0.9 to 2 μg, 0.5 to 1.5 μg or 0.7 to 1.3 μg of said RNA. Likewise, in particular if the LTRs are prepared as LTR solutions (e.g. as in the appended examples), such ratios are iron w/v/w ratios of the MPs to the LTR solution to the RNA ranging from 0.05 to 5 μg, 0.05 to 3 μg, 0.05 to 1 μg, 0.07 to 5 μg, 0.1 to 5 μg, 0.1 to 1 μg, 0.2 to 0.8 μg, 0.3 to 0.7 μg or 0.4 to 0.6 μg (iron weight) of said MPs: 0.4 to 40 μl, 0.4 to 20 μl, 0.4 to 10 μl, 0.8 to 40 μl, 2 to 40 μl, 2 to 10 μl, 2 to 8 μl, 2 to 6 μl, or 3 to 5 μl of said LTR solution: 0.1 to 10 μg, 0.1 to 7 μg, 0.1 to 4 μg, 0.4 to 10 μg, 0.7 to 10 μg, 0.7 to 4 μg, 0.8 to 3 μg, 0.9 to 2 μg, 0.5 to 1.5 μg or 0.7 to 1.3 μg of said RNA. In principle, the narrower ranges are preferred. Most preferred ratios are iron w/w/w ratios of the MPs to the LTR to the RNA of about 0.5 μg of said MPs:about 12 to 20 μg (preferably per about 16 μg) of said LTR:about 1 μg of said RNA and/or iron w/v/w ratios of the MPs to the LTR solution to the RNA of about 0.5 μg of said MPs:about 4 μl of said LTR solution: about 1 μg of said RNA. What has been said above with respect to the preferred LTR, RNA and/or MPs also applies here, mutatis mutandis.

The concentration of an LTR solution to be employed in accordance with the invention may range from about 0.1 to 10, 0.5 to 8, 1 to 7, 2 to 6, 3 to 5 or 1 to 2 μg LTR per μl (the narrower ranges are preferred). Non-limiting examples of particular concentrations are about 0.5, 1, 1.5, 2, 3, 4, 5, 6, 7 or 8 μg LTR per μl. 2 or 4 μg LTR per μl is preferred.

Formation of the complex to be employed in the context of the present invention may take place at an RNA concentration of, for example, about 50 μg/ml to about 350 μg/ml, preferably about 100 μg/ml to about 300 μg/ml, more preferably about 150 μg/ml to about 250 μg/ml and most preferably at about 200 μg/ml.

In order to obtain stable and adequate expression of the proteins encoded by the RNA, it is important that sufficient RNA reaches the desired cells. This, and hence the efficiency of transfection, may be determined in that, after administration of labeled RNA, the content of RNA which has reached the cells is determined by measurement of a labeling. Flow cytometry can be used for the determination of the labeling. When labeling is effected with a fluorescent molecule, the transfection efficiency can be calculated, for example as the percentage of the cell population wherein the fluorescence intensity is higher compared to control cells which were only treated with PBS. The RNA to be employed according to the invention can be produced effectively and the transfection efficiency is high.

The translation efficiency designates the efficiency by which the RNA is translated into the protein. The higher the translation efficiency, the lower can be the dose of RNA which has to be used for the treatment. The translation efficiency can be determined by comparing the proportion of translation for RNA to be employed with the translation ratio for a control RNA. In principle, the translation efficiency with the RNA to be employed may be somewhat lower. This may be, however, more than compensated by the far higher stability which is manifested in the duration of the protein expression.

In principle, the dosage regimen of the active compounds/pharmaceutical composition of the invention can be determined by the attending physician, for example based on clinical factors. As known in the medical arts, dosages for any one patient depend on many factors, including the patient's size, weight, body surface area, age, the particular compound to be administered, sex, time and route of administration, general health, and on other drugs which may be administered concurrently. However, the skilled person/the attending physician is readily in a position to (a) deduce (therapeutically) effective concentration(s) and/or dosages, e. g. in vivo or ex vivo. Corresponding samples may be taken from, for example, the bone (e.g. by a suitable probe) and the active compounds (BMPs and/or suitable markers) may be detected and their corresponding concentrations may be determined in said samples, for example by HPLC.

The determination of the active compound concentrations may be obtained in human patients, healthy (human) individuals as well as in animals, like laboratory animals, non-human transgenic animals (e.g. transgenic mice, rats, pigs, and the like). It is envisaged that the determination of active compound concentrations in, e. g. the bone, may, for example, be deduced in (healthy) volunteers and corresponding administration schemes for (human) patients may be established. For example, the dosage dependencies (e.g. dosage administered versus concentration-/dosage detected in various regions of the bone) may be determined by standard methods known in the art. Further methods comprise, but are not limited to, the detection of labelled peptides in vivo (e.g. by corresponding labelling techniques, like radioactive labelling, fluorescent labelling, etc.) or physiological/biochemical assays. Accordingly, the dosage of active compounds to be administered in order to obtain a desired concentration of the active compounds in a certain part of the bone may be deduced. These and other methods to deduce such concentrations are also known in the art.

In particular, suitable doses of the RNA to be transfected in accordance with the invention (e.g. μg RNA per cell) can readily be determined by the skilled person. Respective guidance is provided in, for example, Kormann (loc. cit.), Mays (loc. cit.), WO 02/00870 and in the appended examples.

The dose used in each case may depend on the function the BMP RNA has to fulfill. As stated above, also the duration of action of the RNA can be deliberately adjusted. The dose and/or duration of the treatment may also depend on the particular indication. If, for example, the RNA is used for the chronic therapy of a bone disease due to a deficient BMP gene, the duration of action will be as long as possible, while with other indications it can be deliberately adjusted to a suitable time window. The respective doses may be set accordingly.

However, as mentioned, it was found in the context of the invention that particular doses are extraordinary useful, in particular as they result in highly effective and/or efficient transfection.

Such particular doses of the RNA to be transfected range from 0.5 to 100 pg, 0.5 to 70 pg, 0.5 to 40 pg, 5 to 100 pg, 10 to 100 pg, 1 to 50 pg, 5 to 40 pg, 10 to 30 or 15 to 25 pg RNA per cell (to be transfected). In principle, the narrower ranges are preferred. Most preferred doses are doses of about 20 pg RNA per cell (to be transfected). The above (ranges of) doses are particularly useful if the RNA is to be delivered (to cells or tissue) ex vivo or in vitro.

In one aspect, the pharmaceutical composition of the present invention comprises a matrix or scaffold; also referred to herein elsewhere and in the art as "carrier". It is particularly envisaged in accordance with this aspect that the RNA to be used has been added to the carrier or has been loaded into/onto the carrier. More particular, it is envisaged that the pharmaceutical composition of the present invention comprises a combination of a carrier and a complex as described herein which contains the RNA to be employed and which likewise may be added to the carrier or has been loaded into/onto it. In other words, it is envisaged that the RNA is loaded into/onto or have been added to the carrier in form of this complex. What is described with respect to the complex and RNA herein elsewhere also applies here, mutatis mutandis.

In the context of the invention, a carrier is a body or a substance which can be contacted in vivo, ex vivo or in vitro with cells or tissue to be transformed/transfected. It is envisaged that the carrier carries the RNA to be used in accordance with the invention and, optionally, is seeded with the cells to be transformed/transfected. It is particularly envisaged that, as such, the RNA is comprised in a complex as described herein. Carriers to be used in accordance with the invention are known in the art and are, for example, described in WO 01/00708 and [10-12]. Besides the RNA, also compounds like, e.g., small molecules and/or cytokines may be loaded into/onto the carrier. This may, for example, enhance the immigration of the cells to be seeded (into the carrier) and/or improve transfection efficacy.

The carrier may be a material connected in a coherent way, i.e. a solid substance, particularly preferably a plastic or deformable solid substance such as e.g. a gel, a sponge, a foil, a powder, a granulate or a fascia. The carrier can consist of biologically non-resorbable or, preferably, biologically resorbable material.

The carrier may also be a carrier produced by the cross-linkage of the (co)polymers according to the invention, preferably in the presence of the RNA. Thus, there is, for example, the possibility of introduction of known gene vectors (naked) RNA, lipoplexes, polyplexes and the like), chemically unmodified or chemically modified, in cross-linked polymers according to the invention. For this purpose, the cross-linkage takes place, e.g. in situ, in the presence of the gene vector, oligonucleotide etc. by addition of an agent triggering the cross-linkage in an aqueous or organic solvent. The nature of the cross-linking agent depends on the structure of the copolymer. Therefore, e.g. the polymer backbone (as, for example, shown in FIG. 2 of WO 01/00708) can be cross-linked by addition of dithiols such as e.g. cyteinyl-cysteine or non-aminoacid-like dithiols. Cross-linkage of (co)polymers containing carboxylic acid can take place by adding any diamines during the activation of carboxylic acid (e.g. reaction of the carboxylic acid to an activated ester in situ) (Nathan et al., Macromolecules 25 (1992), 4476-4484). A polymer backbone with primary or secondary amines can take place e.g. by adding an activated dicarboxylic acid. After the cross-linkage, the preparation can be dried until a film is formed.

An example of a biologically non-resorbable material is silicon (e.g for catheters). It is, however, also possible to use different biologically non-resorbable materials which can be introduced into the body as implants and/or have already been used, e.g. in plastic surgery. Examples thereof are PTFE (e.g. for vessel replacements), polyurethane (e.g. for catheters), metal materials (e.g. medicinal steels, titan alloy for endoprostheses; metal meshes to be used as vessel support (stents)).

Preferably, the carrier is a biologically resorbable material. Examples thereof are fibrin glues or fibrin clots (for example produced from thrombin or fibrinogen), chitin, oxycellulose, gelatine, polyethylene glycol carbonates, aliphatic polyesters such as e.g. polylactic acids, polyglycol acids and the amino acid compounds derived therefrom, such as polyamides and polyurethanes or polyethers and the corresponding mixed polymerisates. Moreover, any other biologically degradable polymer can be used as carrier, in particular so-called self-curing adhesives on the basis of hydrogels. In particular, any materials are suitable as biologically resorbable materials which can be degraded enzymatically in the body and/or by hydrolytic processes. Examples thereof are also bio-resorbable chemically defined calcium sulphate, tricalcium phosphate, hydroxy apatite, polyanhydrides, carriers made out of purified proteins or of partially purified extracellular matrix. The carrier collagen is particularly preferred, particularly preferably a collagen matrix produced from cartilage and skin collagens, for example as distributed by Sigma or Collagen Corporation. Examples of the production of a collagen matrix are described e.g. in the U.S. Pat. Nos. 4,394,370 and 4,975,527. The carrier may be fibrin and, in particular, a fibrin clot.

The carrier is very much preferred to be from collagen and particularly preferred to be a collagen sponge. Collagen sponges are known in the art (e.g. WO 01/00708 and Lee, Biomaterials 32, 2011, 744-752; Meinel, Biomaterials 27, 2006, 4993-5002; Kempen, Biomaterials 30, 2009, 2816-2825) and can, for example, be purchased as "KOLLAGEN Resorb™" from Resorba (Nurenburg, Germany).

In general, negatively charged polysaccharides such as glucosaminoglycans bind to collagen via ionic interactions. The binding can take place to positively charged amino acids in the collagen fibrils (lysine, hydroxylysine and arginine) or even to negatively charged amino acids, mediated by divalent cations such as calcium. Furthermore, the ionic binding properties of collagen can purposefully be influenced by pre-treatment with acid or alkaline solution and subsequent freeze-drying. By means of these techniques known in collagen chemistry, it is possible to soak collagen materials with suspensions of the RNA (for example in the herein described complexes) according to the invention to produce an ionic binding between collagen as carrier material and the RNA and RNA complexes, respectively, to be employed in accordance with the invention.

In collagen, positively charged amino acids are not concentrated in short cationic sections. Such structural features of the carrier, however, are beneficial for the efficient binding of RNA. In order to achieve a tighter binding to the carrier material, it can further be derivatised with cationic substances binding RNA such as peptides (Plank et al., Human Gene Therapy 10 (1999), 319-333) or polyethyleneimine (PEI). For this purpose, the collagen sponge is modified e.g. with the bifunctional coupling reagent succinimidyl-pyridyl-dithiopropionate (SPDP). Polyethylene imine is derivatised with iminothiolane, which leads to the introduction of thiol groups. The cationic peptide to be coupled carries a cysteine at the C-terminus. The thiol groups react with the SPDP-derivatised collagen sponge by forming disulphide bridges. The sponge derivatives obtained in that manner should bind the RNA tightly, and the release of the RNA is expected to take place with a desired long delay in time.

For the production of a matrix/scaffold, i.e. carrier, loaded with the RNA to be used in accordance with the invention, for example, the dry (collagen) material can be incubated with RNA/(polymer) complexes, for example in a lyoprotectant solution about 5%, preferably about 2%, glucose. The loaded carrier, e.g. sponge, may then be freeze-dried and/or vacuum dried.

In general, an RNA-loaded carrier according to the invention can be produced by contacting a corresponding carrier with the RNA, in particular as comprised in a herein described complex, so that the carrier absorbs the RNA, or the respective complex, or binds it in such a way that it can be released again, preferably in a retarded manner. Corresponding methods are known to the person skilled in the art (Bonadio et al. (1999), Nat. Med. 5(7): 753-759; Shea, L. D. et al. (1999), Nat. Biotechnol. 17 (6): 551-554). For example, the production of a combination of a collagen sponge or fibrin clot as a carrier and an RNA/LTR complex is described herein.

In principle, the RNA to be employed in accordance with the invention may be delivered/administered by any suitable route or mode of delivery/administration.

The RNA to be employed according to the invention may be administered in a manner known per se to patients who need the protein or protein fragment encoded by RNA, e.g. because they have a disease due to a deficient gene. For this, the RNA may formulated as a pharmaceutical preparation with common pharmaceutically acceptable additives. The form of the preparation depends on the location and the nature of administration. Since, in one aspect, the RNA to be employed according to the invention is characterized by particularly high stability, it may be formulated in many ways, depending on where and in what form it is to be used. For example, the RNA may be freeze-dried, processed in this form, e.g. crushed or milled, and stored, and may then be reconstituted when required and retains its biological activity.

In one aspect, the pharmaceutical composition of the invention (or the RNA comprised therein) is to be delivered/administered via gene therapy or is prepared for gene therapy. In particular the gene therapy is envisaged to be transcript therapy, more particular, transcript replacement therapy.

The RNA, for example when being loaded (e.g. in form of a complex) onto a carrier, may be delivered/administered in vivo or ex vivo. Suitable routes or modes of delivery/administration are known in the art and are, for example, described in Mitragotri (Nat Rev Drug Discov 13(9) (2014), 55-72), Tavernier G (loc. cit.) and Yin (Nat Rev Genet 15(8) (2014), 541-55). For example, the RNA, for example when being loaded (e.g. in form of a complex) onto a carrier can be transferred into cells, preferably into cells of higher eukaryotes, preferably of vertebrates, particularly of mammals in vitro, in vivo and ex vivo. It has been demonstrated in accordance with this invention that the provided means and methods are particularly useful in the context of in vivo and ex vivo delivery/administration approaches.

In one aspect, the RNA may be delivered/administered in vivo. According to this aspect, the RNA (or pharmaceutical composition comprising it) may be prepared for in vivo delivery/administration and/or is to be delivered/administered in vivo.

In connection with the in vivo application, it is, for example, possible, to introduce the RNA, for example when being loaded (e.g. in form of a complex) onto a carrier, directly as an implant, e.g. in form of a sponge or clot or as a coating, e.g. on a joint replacement, or as an endoprosthesis (e.g. for the improvement of tissue integration). Furthermore, processing of the coated materials is possible in form of powders which are purposefully introduced into and fixed in the organism by means of common tissue glue systems (e.g. fibrin glue) and become effective in the form of a depot (transfection).

In particular, it is envisaged that the RNA be delivered/administered into or in close proximity to a tissue of a patient, in particular a tissue in which induction of bone growth, bone regeneration, bone formation, osteogenesis ossification and the like is desired. Such tissue may, for example, be bone tissue itself. Hence, the RNA may be delivered/and administered directly into the bone or the bone tissue of the patient. For example, the RNA may be directly applied into or in close proximity to the bone defect. The tissue may be also other tissue like, for example, muscle tissue. In such a case an ectopic bone formation may, for example, be induced by the RNA. For these purposes, but also other purposes of in vivo delivery/administration, the RNA, for example, in form of a complex as described herein, may be added to or loaded into a matrix or scaffold, i.e. a carrier as described herein above, (e.g. collagen/collagen sponges, fibrin/fibrin clots, titanium films, heparin-chitosan matrix, hydroxiapatite). It is particularly envisaged that this takes place prior to implantation. However, the RNA may also be delivered/administered without a matrix or scaffold. In principle, the (direct) application of the RNA to treat (prevent or heal) the bone disease (e.g. bone defect or fractures) may follow the same procedures as described for the (direct) administration of recombinant proteins like, for example, recombinant hBMP-2 and recombinant hBMP-7 (see, for example Katanec, Coll Antropol 38(1) (2014), 325-30; Cicciù, Open Dent J 6 (2012), 51-5; Docherty Skogh, Plast Reconstr Surg 123(6) (2009), 192e-3e; Baltzer, Orthop Rev (Pavia) 4(1) (2012), e4; Heliotis M, Int J Oral Maxillofac Surg 35(3) (2006), 265-9; van den Bergh J P, J Clin Periodontol 27(9) (2000), 627-36). The RNA may also be added to bone cements or bone filling materials. In this context a paste-like product may be produced. This may be further applied to the bone defect. In principle, the RNA may also be directly injected into the bone, for example without a matrix or scaffold. However, direct injection with a matrix or scaffold is, in principle, also possible.

In another aspect, the RNA may be delivered/administered ex vivo. According to this aspect, the RNA (or pharmaceutical composition comprising it) may be prepared for ex vivo delivery/administration and/or is to be delivered/administered ex vivo. For example, the RNA may be delivered/administered ex vivo into cells (e.g. bone cells) which are to be introduced into the patient, i.e. which may, in the transfected (genetically modified) form, be introduced into the patient. In one specific embodiment, the RNA is delivered/administered ex vivo into cells (e.g. bone cells) of the patient and said cells to which said RNA has been delivered/administered are to be reintroduced into said, i.e. the same, patient, i.e. which may, in the transfected (genetically modified) form, be reintroduced into said patient. Thus, one preferred embodiment, the cells are derived from exactly that patient which is to be treated.

The cells to be (re)introduced into the patient may be any cells suitable for this purpose. The cells may, for example, be osteoprogenitor cells. They may be mesenchymal stem cells (MSCs), for example muscle-derived mesenchymal stem (MMSCs) or, preferably, adipose-derived mesenchymal stem cells (AMSCs) or bone marrow-derived MSCs (BMSCs).

In a more specific embodiment of the ex vivo delivery/administration, the RNA (or pharmaceutical composition comprising it) is prepared for delivery/administration via an autologous tissue graft and/or is to be delivered/administered via an autologous tissue graft. It is particularly envisaged that the autologous tissue graft, in particular cells comprised therein, is transfected, and hence genetically modified, in accordance with the means and methods described herein, i.e. expresses one or more of the herein described BMPs as a result of the ex vivo delivery/administration of the RNA (or pharmaceutical composition comprising it) in accordance with the invention. More particular, it is envisaged that the autologous tissue graft, in particular cells comprised therein, is or is to be transfected in accordance with the invention, i.e. by one or more of the herein described BMP RNAs and the respective transfection means and methods. What has been said with respect to these means and methods herein elsewhere also applies here, mutatis mutandis.

The autologous tissue graft to be employed in accordance with the invention may comprise progenitor cells. It is particularly envisaged that osteoprogenitor cells are comprised. The autologous tissue graft may comprise muscle cells or fat cells (like AMSCs). The autologous tissue graft may comprise bone cells like, for example, osteoblasts, osteoclasts and/or osteocytes. In a specific aspect, the autologous tissue graft is or comprises a bone-tissue pulp. The bone tissue pulp may comprise any of the herein defined (bone) cells and, in particular, any of the herein defined (bone) cells which are to be or have been transfected in accordance with the invention, i.e. which are to be or have been genetically modified in accordance with the invention to express a BMP.

In principle, suitable means and methods for ex vivo delivery/transfection of the BMP RNA are known in the art and are also evident from the appended examples. However, in the context of one specific embodiment of the invention, it is envisaged that the BMP RNA is to be delivered/transfected in Opti-MEM medium (Gibco™, Invitrogen, CA, USA). As mentioned, extraordinary good delivery/transfection efficiency has been achieved with this kind of delivery/transfection medium.

Also for the purpose of ex vivo delivery/administration, the RNA, for example, in form of a complex, may be added to or loaded into/onto a matrix or scaffold, i.e. a carrier as described herein above (e.g. collagen/collagen sponges, fibrin/fibrin clots, titanium films, heparin-chitosan matrix, hydroxiapatite).

In this context, it is particularly envisaged that the carrier/carrier body is, in a first step, pre-loaded with the RNA or, preferably, RNA complex, optionally dried (for example vacuum and/or freeze dried) and, as a second step, seeded with the cells into which the RNA is to be delivered/administered (e.g. transfected).

For drying purposes, a lyoprotectant (for example sucrose) may be added to the RNA/RNA complex at a suitable concentration (e.g. a concentration of about 1% to about 6%, preferably about 2% to about 5% or, in particular, about 5%, about 3% or, most preferred, about 2%).

The transfection efficacy and/or cell viability on the RNA-loaded carrier may be monitored (for example as described in the appended examples). Carriers with weak performance in this respect may be sorted out.

The RNA-loaded carrier, in particular, if it exhibits good performance, may be administered to the patient. In principle, cells which have been transfected with the RNA in the context of the herein disclosed ex vivo purposes may then be delivered/administered, preferably together with the matrix/scaffold into/onto which they have been loaded, in the same manner as described herein above which respect to the in vivo purposes. For example, it may be administered into or in close proximity to a tissue of a patient in particular a tissue in which induction of bone growth, bone regeneration, bone formation, osteogenesis, ossification and the like is desired. Again, this tissue may be bone tissue itself, but also other tissue like muscle tissue. In one particular aspect, it may be directly placed/implanted into or at a site next to the bone defect.

The above described RNA-loaded carriers, and means and methods for their delivery/administration and production, are particularly useful in autologous tissue grafting, in particular in the autologous tissue grafting described herein. What has been said in this respect herein elsewhere applies here, mutatis mutandis. In particular, the carrier may be seeded with the respective progenitor cells, like, for example, osteoprogenitor cells or bone cells, like, for example, osteoblasts, osteoclasts and/or osteocytes, MSCs like MMSCs or AMSCs etc.

The RNA-loaded carrier as described herein are particularly useful in sustained and/or retarded RNA delivery, for example, as depots for RNA delivery, in particular sustained and/or retarded RNA delivery, and as (sustained/retarded) RNA delivery systems, respectively. In principle, this applies for in vivo, in vitro and ex vivo delivery/administration, but, in particular, to the herein described in vivo delivery/administration purposes.

The meaning of sustained/retarded delivery is known in the art and is respectively applied in the context of the invention. For example, sustained/retarded RNA delivery may be an RNA delivery, in particular the delivery of a pharmaceutically active amount of an RNA, over a period of at least one day, two days, three days, four days, five days, six days, one week, two weeks, three weeks, one month, two months, three months, four months, five months or six months. In principle, the longer periods are preferred.

The skilled person is readily able to produce RNA-loaded carrier/carrier bodies suitable in terms of the invention. For this purpose, the skilled person may rely on respective means and methods known in the art (Chevally, Medical and Biological Engineering and Computing 38, 2000, 211-218) and described herein and in the appended examples. For example, the skilled person could apply the above-described method steps. For example the step of cell seeding (and probably steps related thereto) may be omitted when the RNA-loaded carrier is to be produced for the in vivo delivery/administration purposes described herein. The present invention also relates to respective means and methods for producing the RNA-loaded carrier.

For example, the amount of RNA or RNA-loaded on a carrier/carrier body in accordance with the invention may be in the range of about 0.1 μg to about 10 μg, preferably about 0.5 μg to about 8 μg, preferably about 1 μg to about 6 μg, preferably about 1.5 μg to about 5 μg and most preferably about 2 to about 3.5 μg per carrier/carrier body. The amount of cells seeded into/onto a carrier/carrier body may, for example, be about 5,000 to about 50,000, preferably about 7,500 to about 40,000, preferably about 10,000 to about 30,000 per carrier/carrier body. Particular examples are about 10,000, about 20,000 and about 30,000 per carrier body.

As a non limiting example, the above values particularly apply to a carrier body as exemplified in the context of the present invention (i.e.: 5 to 7 mm in diameter and a thickness of about 1 to 2 mm and a volume of roughly about 50 $mm^3$). A carrier body to be employed in accordance with the invention may, for example, be a disc of about 1 mm to several centimeters in diameter (e.g. of about 5 cm diameter)

and a thickness of about 2 mm to 2 cm depending on the form and the diameter of e.g. the bone fraction to be cured. This roughly estimates to a volume of several $mm^3$ to $cm^3$. In principle, the shape of the carrier body (e.g. disc) may for example be adapted to the shape of the bone fraction or may otherwise be in a suitable shape. For example, it may be irregular instead of circular.

In general, the carrier body (e.g. (collagen) sponge) may be adapted to its particular use. For example, its shape may be adapted to the bone fraction, bone lesion, bone cavity (for example caused by the bone fraction, by the bone injury, by a (dental) cyst etc.), bone injury etc. which is to be treated. In one aspect, it is envisaged that the shape of the carrier body fits into the bone fraction/bone cavity. In other words, the carrier body may have the same shape as the bone fraction/bone cavity. In particular, it is envisaged that the carrier body, once being implanted into/next to the injured site of the bone (e.g. bone fraction/bone lesion) resembles, together with the residual part(s) of the bone, the original shape of the bone.

A typical carrier body may be squeezable (e.g. a (collagen) sponge). Hence, the initial shape of the carrier body may be somewhat expanded as compared to the bone fraction, bone cavity etc. to be treated but may be squeezed into the bone fraction, bone cavity etc. so as to resemble the original shape of the bone after implantation.

Also as to these aspects, the carrier body may, for example, be a collagen sponge or fibrin clot (e.g. as described herein). The values of, for example the amount of RNA and/or cells to be loaded into/onto a certain carrier body, can readily be adapted thereto by the skilled person/the attending physician.

In a further embodiment, the RNA is provided in a delayed release polymer, for example as a carrier for the coating of implants. For this purpose, the RNA may be used as such or as an RNA, for example protected with a coating polymer and/or polymer complex.

Moreover, implants are a further option for administering the RNA. On the surface of a respective implant, there may be coating of a delayed release polymer which contains the RNA which encodes (a) BMP(s), e.g. as (a) beneficial factor(s) for the ingrowth of the implant. According to the invention, both, coatings which contain (m)RNA which encodes only one factor (BMP) and also coatings which contain (m)RNAs which encode several factors (BMPs), are envisaged. The various factors (BMPs) may also be provided in a form such that they are released at staggered intervals.

The expression "RNA which encodes one or more factors (BMPs)" should be understood to mean both, an RNA sequence which encodes more than one protein, in singular form or as a fusion protein, and also a mixture of different RNA sequences which encode different (BMP) proteins, where each RNA sequence encodes one protein.

The (m)RNA to be employed according to the invention may advantageously be used in order to promote the ingrowth of implanted prostheses. If it is available on the surface of prostheses to be inserted such as tooth implants, hip endoprostheses, knee endoprostheses or vertebral fusion bodies, the (m)RNA to be employed according to the invention may release (a) BMP(s) which can promote the ingrowth and other functions which are necessary for the newly inserted prostheses. Thus for example the administration of biologically active substances such as growth factors such as BMP-2 or BMP-7 in the context of implantation of prostheses or thereafter may be applied in accordance with the invention. In this embodiment, the RNA to be employed according to the invention which encodes (a) BMP(s) may be applied onto the implant in a coating releasing the RNA (in a measured manner) and then released gradually therefrom (in a measured manner), for example so that the cells in the vicinity of the implant can continuously or intermittently produce and if necessary release the desired factors. Systemic administration of the (m)RNA is also possible. There might be cases where the (m)RNA translation in cells which are not affected by the gene defect is undesirable, e.g. because undesired side effects arise. In order to have the (m)RNA translated selectively only in the cells which need the encoded protein, e.g. in cells in which a gene defect exists, the corresponding vector may either be supplemented by sequences which enable addressing of the tissue affected, e.g. via ligands. In a further embodiment, sequences to which endogenous micro-RNAs bind, which are not expressed in the target cell, may be added to the vector which contains the (m)RNA, so that the (m)RNA are degraded in all cells which contain the relevant endogenous micro-RNAs, while they are retained in the target cells. Thus side effects can be minimized.

When the RNA is administered systemically, it is usually formulated as an injectable liquid with normal additives such as agents adjusting the tonicity and stabilizers, preferably as a unit dosage form. As stabilizers, those normally known, such as for example lipids, polymers and nanosystems or liposomes, are used. In a preferred embodiment, a composition suitable for parenteral administration is provided. Common carriers, as a rule biocompatible i.e. pharmaceutically acceptable, synthetic, natural or mixed natural-synthetic polymers, the release properties whereof can be specifically adjusted, are well known and thus need no more detailed explanation here. Polylactide or polylactide/glycolide polymers are for example used. In this way it is, for example, possible selectively to release the desired factors continuously, intermittently, over a longer or shorter time and at the desired site.

The RNA to be employed according to the invention may particularly provide for high stability, which results in long-continuing protein expression. For example when the RNA is intended for the treatment or prevention of bone diseases due to gene defects, the longer it remains in the cell the more valuable it may be. The more rapidly the RNA is degraded, the more rapidly the protein expression ends and, in certain cases the more often the RNA must be administered. Conversely, with a stable RNA which remains in the cell for a long time the frequency of dosing may be greatly reduced. It has been found that RNA to be employed according to the invention (particularly the cmRNA) is stably expressed for up to 4 weeks. Hence, a very long-acting RNA may be used where this is necessary. An RNA expression which can last up to 4 weeks, is thus ideally suited for the treatment of chronic bone diseases. Respective RNA has only to be given rarely (e.g. every 4 weeks) or even only once.

In this context, evidence is provided herein that a single treatment with BMP RNA is sufficient for a sound, and even for a complete, treatment (or prevention) of bone-related diseases, disorders or injuries. Hence, in a specific embodiment, the pharmaceutical composition of the invention is prepared for a single administration/treatment and/or is to be administered only once/as a single treatment. A subsequent second administration/treatment (or even further subsequent administrations/treatments) is not required according to this specific embodiment.

For other embodiments, e.g. when RNA is only intended for temporary expression, the duration of the protein expression may be adjusted by influencing the stability. A further valuable property of the RNA to be employed is that the duration of action can be adjusted selectively via the stability so that the duration of the protein expression can be tailored so that it takes place in a desired time window (see above).

The stability of the mRNA to be employed according to the invention can be determined by methods known per se. Particularly suitable are methods for the determination of the viability of cells which contain the RNA in comparison to cells which do not contain the RNA. The production of the encoded protein (BMP) over time can also be monitored. Here, stability of an RNA is understood to mean that, when it has been introduced into the cell, the RNA which can express the desired protein or is translatable into the protein, or a functional fragment thereof, remains capable of expression over a prolonged period, is not immediately degraded and is not inactivated.

A method for testing the stability and the survival time of RNA in a cell thus consists in determining how long a protein encoded by the RNA is detectable in the cell or performs its function. Methods for this are described in the examples. Thus, for example, an (m)RNA with a sequence encoding a reporter molecule can be introduced into the cell, optionally together with an RNA encoding a desired protein, and after predefined time periods, the presence of a reporter molecule, and optionally the encoded protein, are then determined. Suitable reporter molecules are well known in the state of the art and those commonly used can also be used here. In a preferred embodiment, RFP, red fluorescing protein, is used as the reporter molecule.

The pharmaceutical composition of the invention is to be administered to a patient, preferably to a human patient/a human. However, the herein described bone diseases (and related conditions) may also be treated or prevented in a non-human animal subject/patient like, for example, a pet (e.g. dog, cat, rabbit, rat and mouse), a cattle (e.g. cow, pig, sheep), a horse or pony or a bird (e.g. chicken, turkey, parrot).

Any of the pharmaceutical compositions of the invention may be provided together with an instruction manual or instruction leaflet. The instruction manual/leaflet may comprise guidance for the skilled person/attending physician how to treat or prevent a disease or disorder as described herein (bone disease) in accordance with the invention. In particular, the instruction manual/leaflet may comprise guidance as to the herein described mode of delivery/administration and delivery/administration regimen, respectively (for example route of delivery/administration, dosage regimen, time of delivery/administration, frequency of delivery/administration). In particular, the instruction manual/leaflet may comprise the instruction that the pharmaceutical composition is prepared for a single administration/treatment and/or is to be administered only once/as single treatment. The instruction manual/leaflet may further comprise the instruction that a subsequent second administration/treatment (or even further subsequent administrations/treatments) is not required. In principle, what has been said herein elsewhere with respect to the mode of delivery/administration and delivery/administration regimen, respectively, for example with respect to the ex vivo or in vivo delivery/administration, the ratios of the MPs, LTR and/or RNA and the doses may be comprised as respective instructions in the instruction manual/leaflet.

The present invention further relates to the BMP (cm) RNAs as described and defined herein. What has been said herein elsewhere with respect to BMPs and RNA also applies here, mutatis mutandis.

One non-limiting but preferred example of the (cm)BMP RNAs of the invention is an RNA with a sequence which encodes a BMP (for example BMP-2 or BMP-7), or a functional fragment of the BMP, wherein 5 to 50%, 7.5 to 30%, 15 to 25 or, preferably, about 25% of the cytidines of said RNA are chemically modified cytidines (e.g. 5-methylcytidines; m5C) and/or 5 to 50%, 7.5 to 30%, 15 to 25 or, preferably, about 25% of the uridines of said RNA are chemically modified uridines (e.g. 2-thiouridines; s2U).

In one aspect, the present invention relates to a pharmaceutical composition, in particular a pharmaceutical composition as described herein, comprising the BMP-encoding RNA, in particular the above-described BMP encoding RNA, preferably in form of a complex as described herein and, more preferably, in form of an RNA-loaded carrier as described herein.

The present invention also relates to the complexes as described and defined herein, i.e. the complexes which comprise or are complexed with the (cm)RNA as described herein. In particular, the invention relates to the transfection complexes as described and defined herein (e.g. the lipofection, magnetofection and magnetolipofection complexes). In principle, what has been said herein elsewhere with respect to BMPs, RNA, LTRs, MPs and the other essentials of the complexes also applies here, mutatis mutandis.

One non-limiting but preferred example of the complexes of the invention is a complex which comprises/is complexed with a sequence which encodes a BMP (for example BMP-2 or BMP-7), or a functional fragment of the BMP, wherein 5 to 50%, 7.5 to 30%, 15 to 25 or, preferably, about 25% of the cytidines of said RNA are chemically modified cytidines (e.g. 5-methylcytidines m5C) and/or 5 to 50%, 7.5 to 30%, 15 to 25 or, preferably, about 25% of the uridines of said RNA are chemically modified uridines (e.g. 2-thiouridines; s2U). More specifically, such a complex may comprise one or more LTR (e.g. Lipofectamine 2000, Dogtor, DreamFect™ or, preferably, DF-Gold™ or C12-(2-3-2)) and/or MPs (e.g. core-shell MPs, iron oxide silica MPs and/or (branched)PEI-decorated MPs, like MPs with a SiOx/Phosphonate-PEI coating (e.g. SO-Mag6-115 MPs)) as described and defined herein. Even more specifically the MPs, LTR and/or RNA may be comprised in such a complex (or in the other complexes of the invention) at the respective ratios as described herein-above. In particular, these ratios may be w/w ratios of the LTR to the RNA of about 8 µg or about 20 µg of said LTR per µg of said RNA, v/w ratios of the LTR solution to the RNA of about 2 µl or about 5 µl of said LTR solution per µg of said RNA, iron w/w ratios of the MPs to the RNA of about 0.5 µg of said MPs per µg of said RNA, iron w/w ratios of the MPs to the LTR of about 0.5 µg of said MPs per about 12 to 20 µg (preferably per about 16 µg) of said LTR, iron w/v ratios of the MPs to the LTR solution of about 0.5 µg of said MPs per 4 µl of said LTR solution, iron w/w/w ratios as described herein elsewhere, for example at iron w/v/w ratios of about 0.5 µg of said MPs:about 12 to 20 µg (preferably per about 16 µg) of said LTR:about 1 µg of said RNA, and/or iron w/v/w ratios as described herein elsewhere, for example at iron w/v/w ratios of about 0.5 µg of said MPs:about 4 µl of said LTR solution:about 1 µg of said RNA. Such a complex (or the other complexes of the invention) may also comprise one or more further lipid(s) (e.g. "helper lipid(s)"). What has been said herein above with respect to the further lipid(s) (e.g. "helper lipid(s)") also applies here, mutatis mutandis.

Also the above described RNA or complexes are intended to be used in accordance with the means and methods of the invention. In this context, the RNA or complexes is/are intended to be comprised in the pharmaceutical composition of the invention. The invention also relates to a pharmaceutical composition comprising a BMP (cm)RNA or a complex as described and defined herein.

The BMP RNA and the respective complexes can readily be prepared according to art-known means and methods and according to the means and methods described herein and in the appended examples. For example, the BMP RNA can be prepared by in vitro transcription systems and may, hence, be in vitro transcribed BMP RNA (IVT BMP RNA). In this context, a method wherein the BMP RNA to be employed according to the invention is produced by in vitro transcription from a mixture of ATP, CTP, GTP and UTP is, for example, suitable. The materials necessary for performing the in vitro transcription are known to those skilled in the art and available commercially, in particular buffers, enzymes and nucleotide mixtures. The nature of the DNA used for the production of the RNA to be employed according to the invention is also not critical. As a rule, it may be cloned DNA.

In another aspect, the present invention relates to the herein described matrix or scaffold/carrier/carrier body, i.e. to the matrix/scaffold/carrier/carrier body loaded with the RNA to be employed in accordance with the present invention, for example in form of a complex described herein and, optionally, further seeded with the cells as described herein.

In another aspect, the present invention also relates to a pharmaceutical composition which comprises the herein defined RNA-loaded matrix/scaffold/carrier/carrier body. The present invention also relates to the herein described RNA-loaded carrier as ready-to-use bioproduct, in particular, for use in bone regeneration and/or the herein described bone diseases.

The present invention further relates to the use of the matrix/scaffold/carrier/carrier body, pharmaceutical composition or bioproduct formulated for sustained and/or retarded delivery and as a sustained delivery system/depot, respectively.

The present invention is further described by reference to the following non-limiting figures and examples.

The patent or application file contains at least one drawing executed in color. Copies of this patent or patent application publication with color drawings will be provided by the Office upon request and payment of the necessary fee.

The Figures show:

FIG. 1. Determination of integrity and size of the modified mRNAs using native agarose gel electrophoresis. cmRNAs and RiboRuler RNA ladder high range were mixed with RiboRuler formamide containing loading dye and incubated for 10 minutes at 70° C. Subsequently samples were chilled on ice and applied to the agarose gel. Detection was done by ethidiumbromide staining and visualization on Intas Gel Imaging System.

Figure 2:
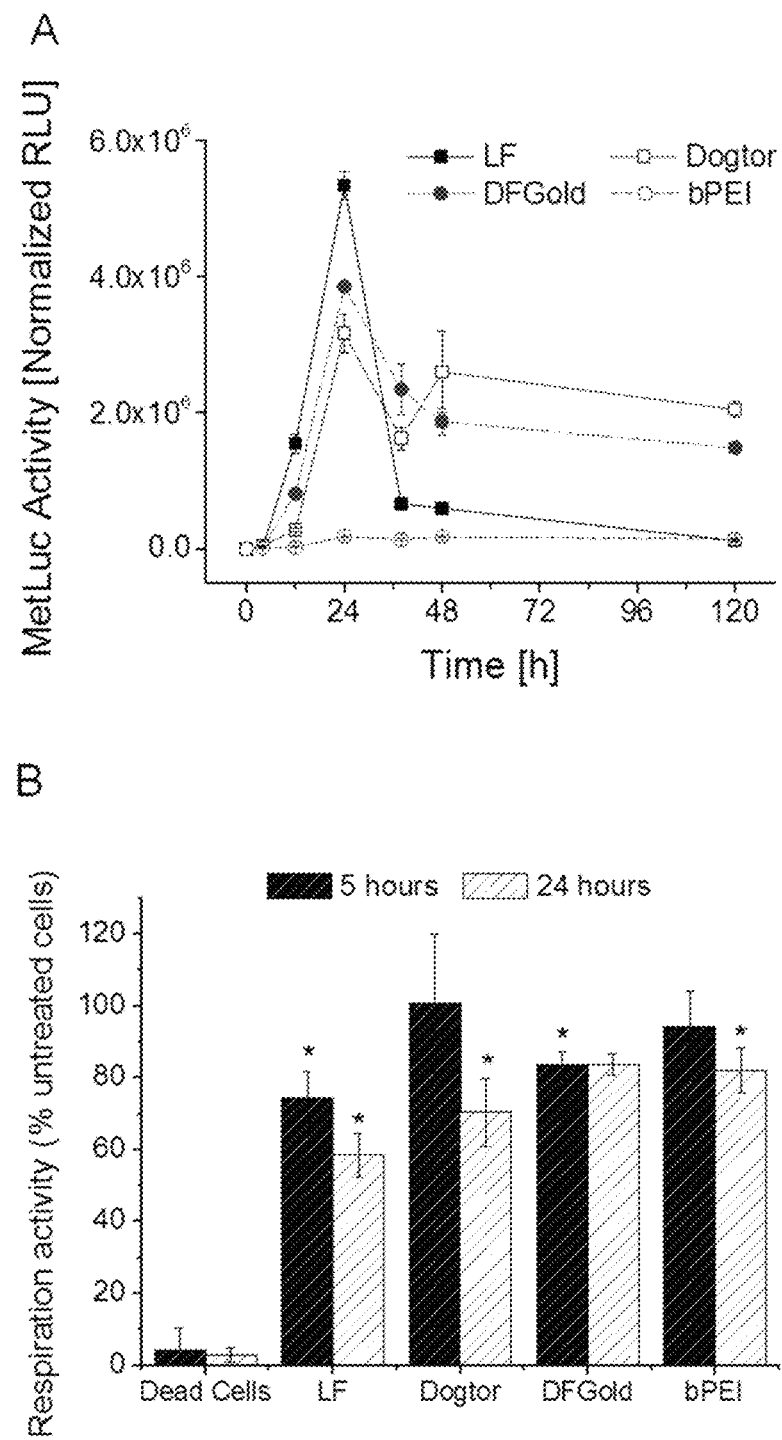
Figure 2:
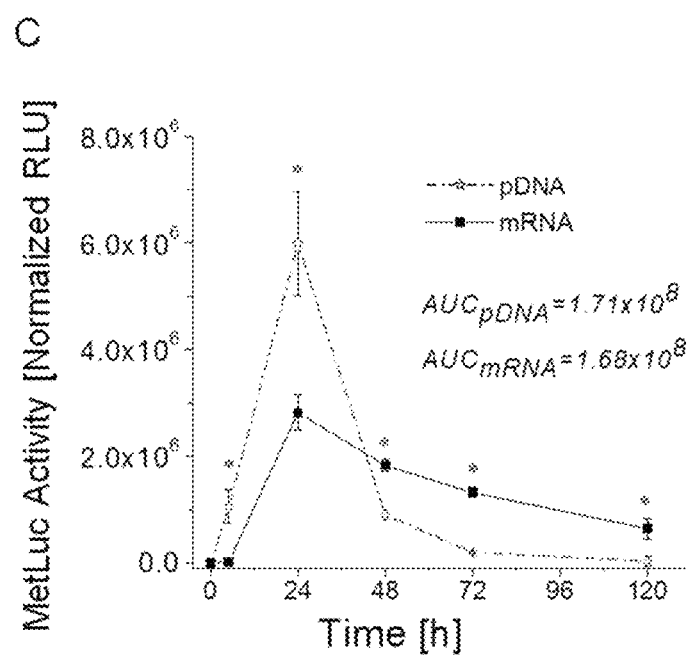

FIG. 2. (A) Kinetics of the Metridia luciferase expression in AMSCs transfected with MetLuc cmRNA complexes formed using Lipofectamine2000 (LF), Dogtor, DF-Gold or bPEI as enhancers at a cmRNA dose of 20 pg/cell and (B) viability of the cells 5 and 24 h after transfection. Significant difference between untransfected control (100% cell viability) and transfected cells are indicated by (*). (C) Comparison of the time profile for reporter expression in AMSCs after transfection with DF-Gold lipoplexes of the pDNA or cmRNA both encoding MetLuc. Areas under the "pDNA" and "cmRNA" curves, $AUC_{pDNA}$ and $AUC_{cmRDNA}$, were calculated by integrating the data between zero and 120 h time points. Significant difference between pDNA and cmRNA data are indicated by (*).

Figure 3:
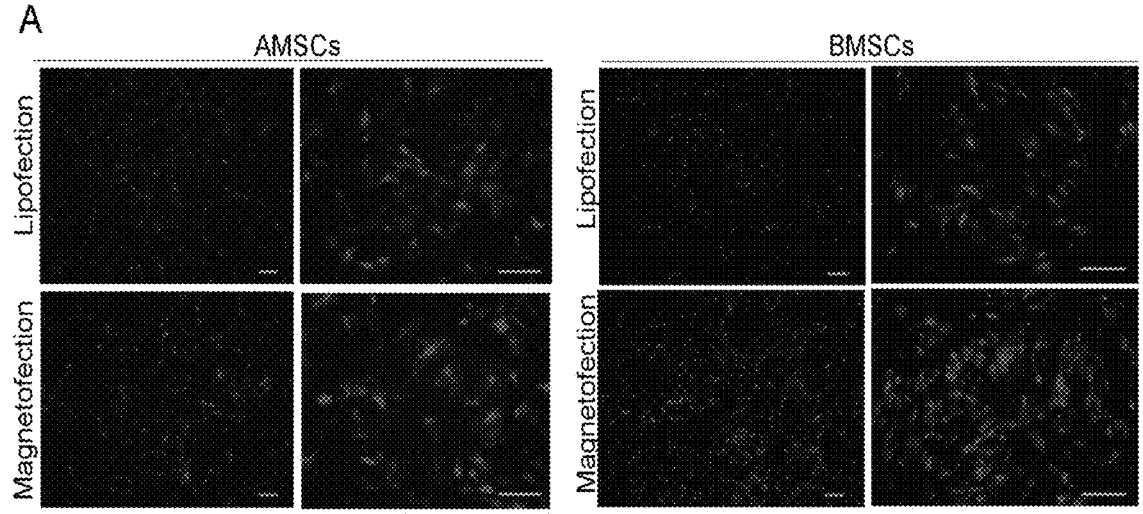
Figure 3:
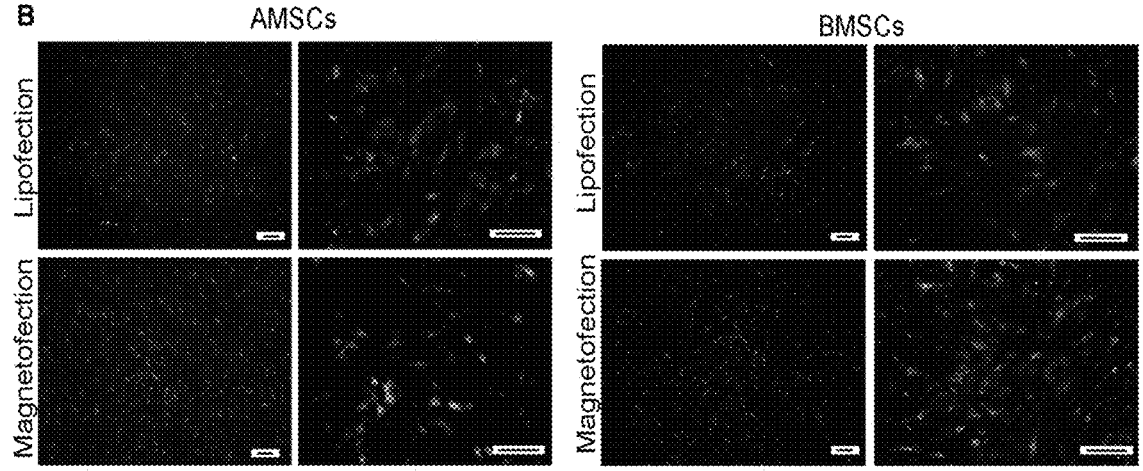
Figure 3:
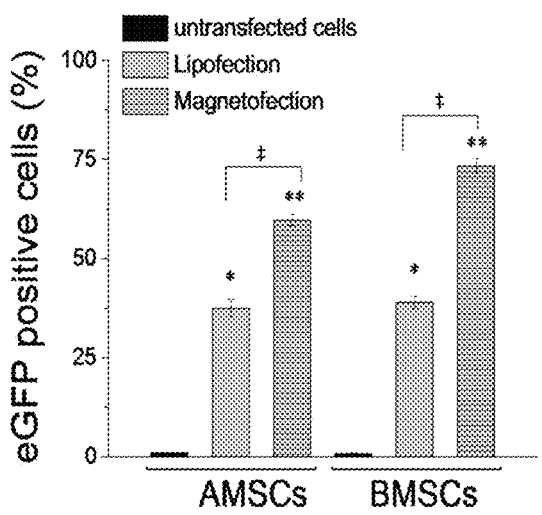
Figure 3:
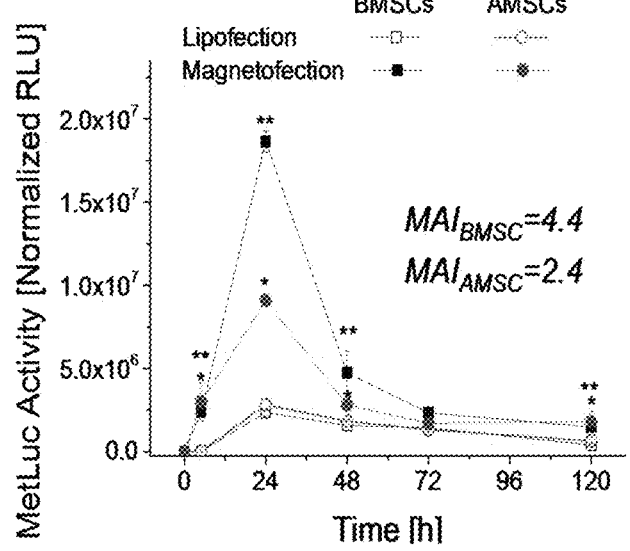

FIG. 3. Expression of the Tomato, eGFP and MetLuc reporters in AMSCs and BMSCs after transfection with DF-Gold/cmRNA lipoplexes and DF-Gold/SO-Mag6-115/cmRNA magnetic triplexes. The applied cmRNA dose was 20 pg/cell. Fluorescence microscopy images of the cells taken 24 hours after transfection with the complexes of: (A) tomato N1 cmRNA and (B) eGFP cmRNA. The scale bars represent 250 µm. (C) FACS results on percent of the cells expressing eGFP 24 hours after transfection with the complexes of eGFP cmRNA. Significant differences between untransfected and lipofected (*) or magnetofected cells (') as well as between lipofection and magnetofection (‡) are indicated in the figure. (D) Time course of the Metridia luciferase expression is shown for both cell types transfected with the complexes of MetLuc cmRNA. Significant difference between magnetofection and lipofection are indicated by (*) and (**) for the AMSCs and BMSCs, respectively. To calculate the MAI, the area under the "Magnetofection" curve $AUC_{MF}$ was normalized to the area under the "Lipofection" curve $AUC_{LF}$ for both BMSCs and AMSCs.

Figure 4:
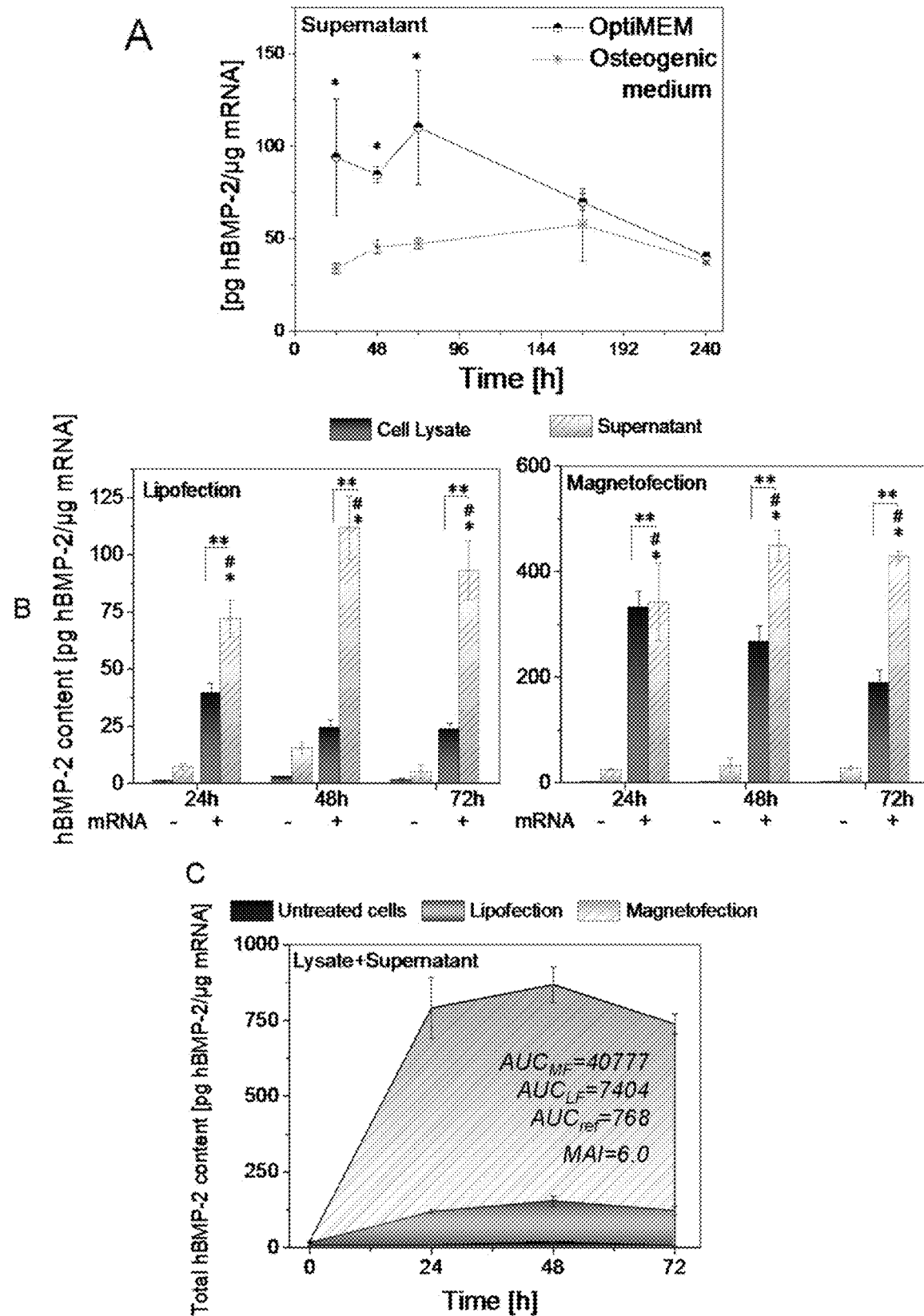

FIG. 4. hBMP-2 produced in AMSCs at different time points after transfection with DF-Gold/cmRNA lipoplexes and DF-Gold/SO-Mag6-115/cmRNA magnetic triplexes. The produced hBMP-2 was normalized to the applied hBMP-2 cmRNA dose (20 pg/cell). (A) Effect of the culture media (osteogenic medium vs. Opti-MEM) used upon transfection on the content of the secreted hBMP-2 measured in supernatant; (*) indicate significant differences between compared groups. (B) Content of endogenous hBMP-2 (cmRNA (−)) and hBMP-2 produced by transfected cells (cmRNA (+)) measured in supernatant (secreted hBMP-2) and in cell lysate (intracellular hBMP-2) at day 1, 2 and 3 after transfection. (*) Indicate significant difference on secreted hBMP-2 between untreated and transfected cells. (**) Indicate significant difference between secreted and intracellular hBMP-2 for transfected cells at a given observation time. (#) Indicate significant difference on secreted hBMP-2 between lipofection and magnetofection. (C) Time course of the total (secreted+intracellular) hBMP-2 content in the transfected cells. To calculate the MAI=6.0, the area under the "Magnetofection" curve $AUC_{MF}$ was normalized to the area under the "Lipofection" curve $AUC_{LF}$ after substraction of the area $AUC_{ref}$ under the "Untreated cells" curve showing the level of the endogenous hBMP-2.

Figure 5:
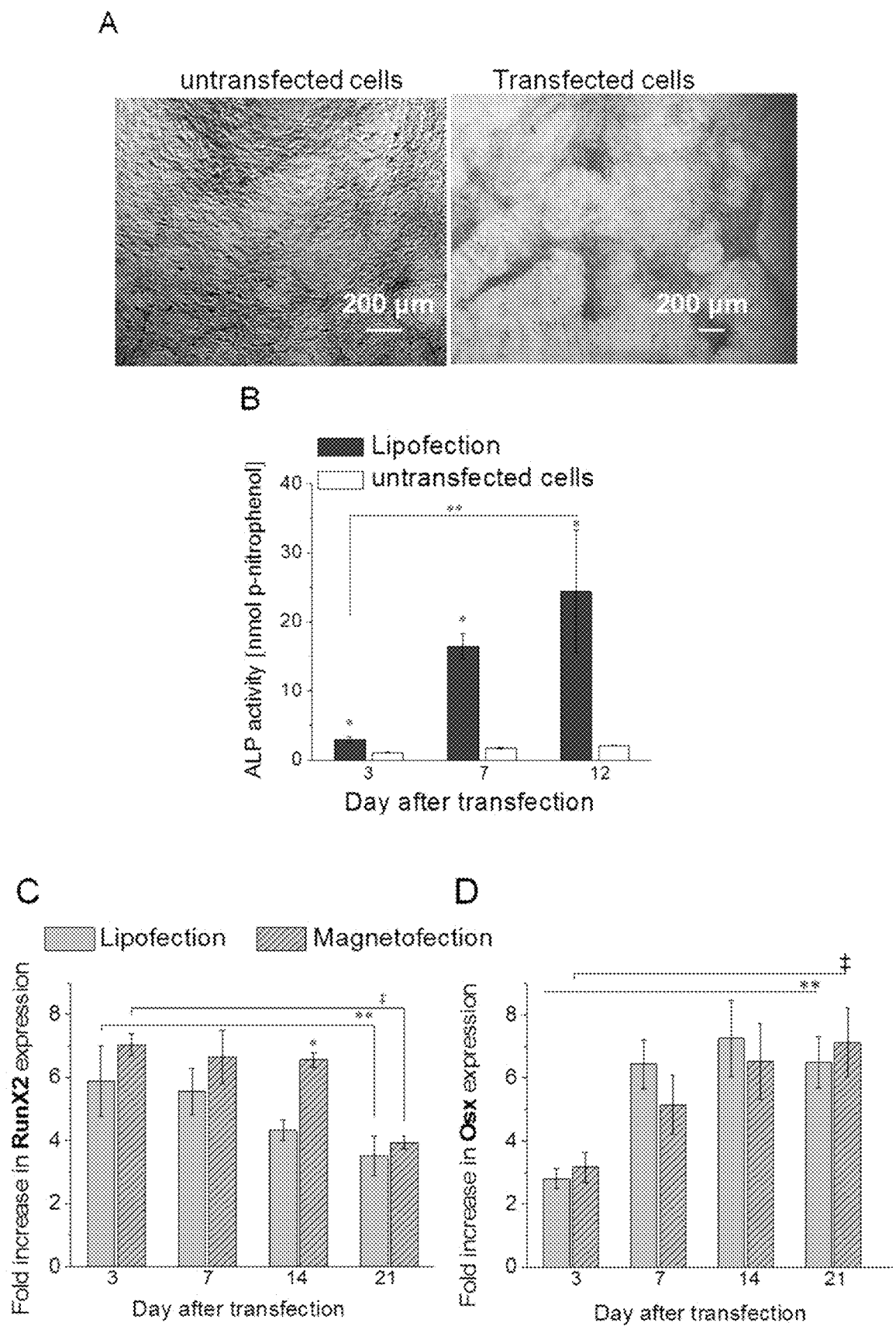
Figure 5:
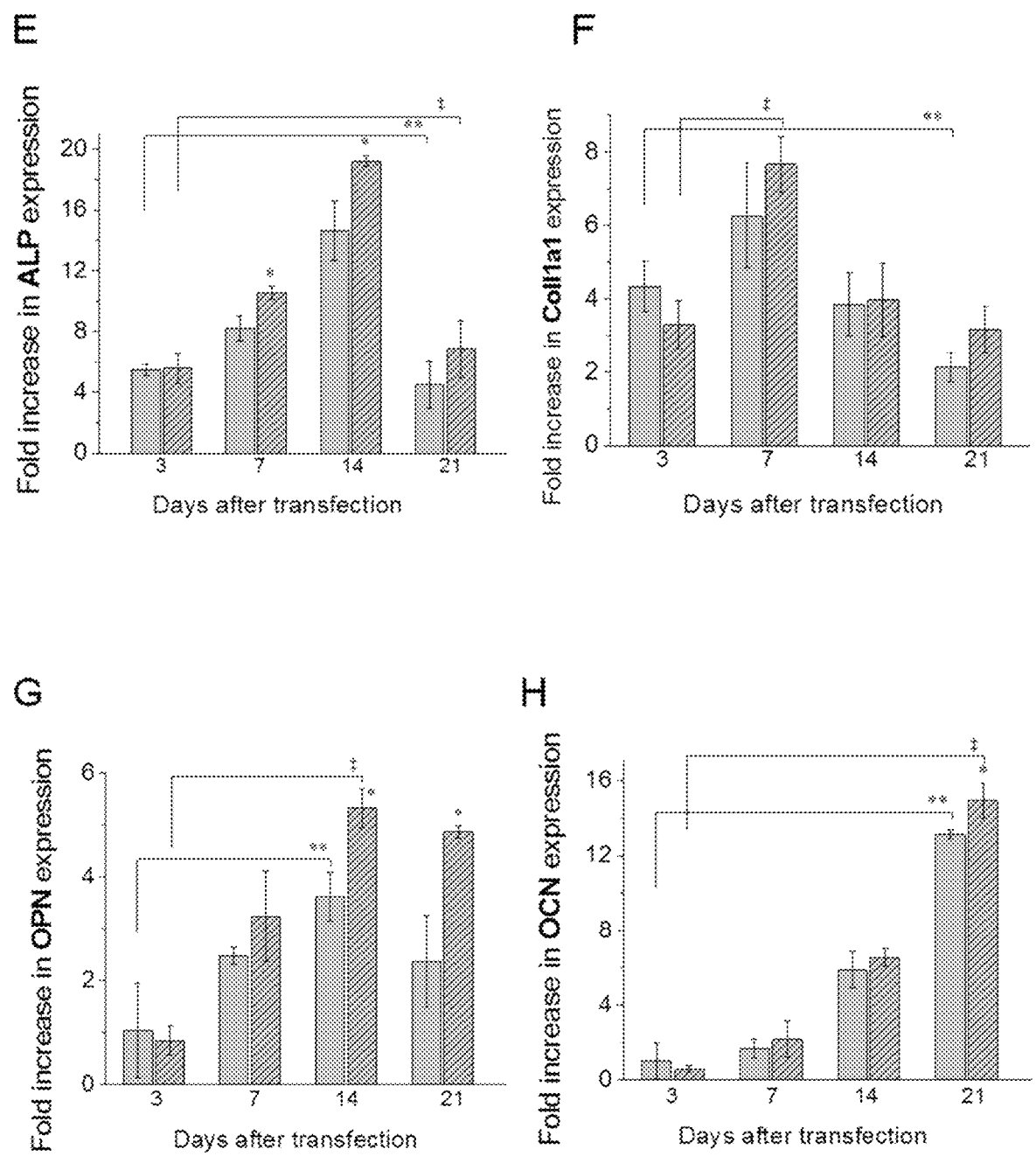

FIG. 5. Alkaline phosphatase (ALP) activity of the cells transfected with DF-Gold/cmRNA lipoplexes. (A) ALP staining 12 days after transfection. (B) ALP activity 3, and 12 days post-transfection. (*) Indicate significant difference between untransfected and transfected cells and (**) between 3 and 12 days post-transfection. Increase in expression of bone-related genes after lipofection and magnetofection of AMSCs with complexes of hBMP-2 cmRNA at an applied cmRNA dose of 20 pg/cell. Fold increase in expression of (C) RunX2, (D) Osx, (E) ALP, (F) Coll I, (G) OPN and (H) OCN at 3, 7, 14 and 21 days after transfection. Gray bars represent lipofection with DF-Gold/cmRNA complexes while dashed bars symbolize magnetofection with SO-Mag6-115/DF-Gold/cmRNA triplexes. (*) Indicate significant difference between lipofection and magnetofection group for the same observation time. (**) Indicate significant difference when comparing different time post-transfection for the lipofection and (‡) for the magnetofection group.

Figure 6:
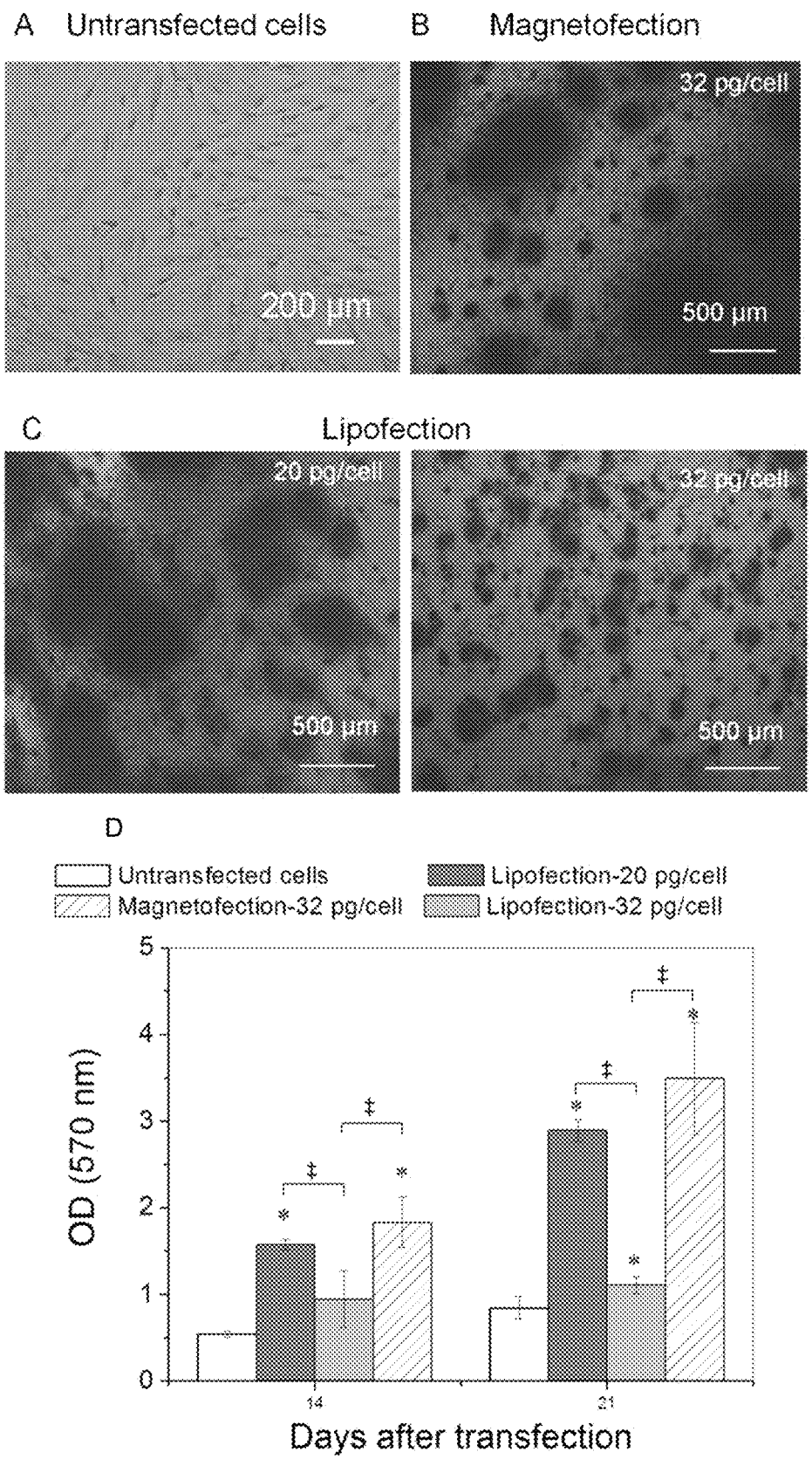

FIG. 6. Mineralization of AMSCs after lipofection and magnetofection. Alizarin red staining 21 days after transfection: (A) untrasfected cells, (B) cells after magnetofection and (C) cells after lipofection. (D) Quantification of alizarin red staining 14 and 21 days after transfection. Significant differences between untransfected and transfected cells are indicated by (*) and a comparison among different transfected cells by (‡).

Figure 7:
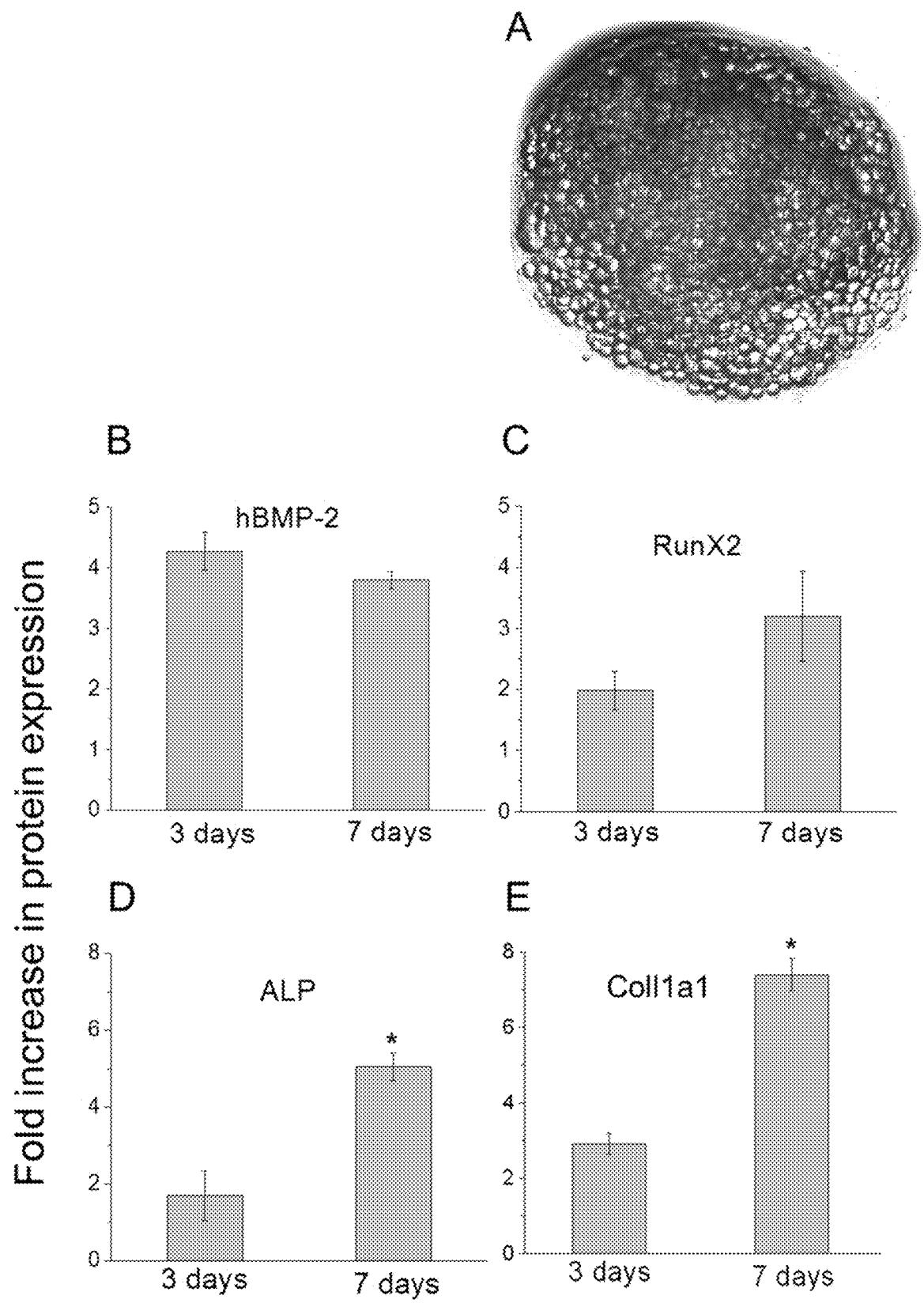

FIG. 7. Transfection of 3 mm fat discs with DF-Gold/cmRNAs lipoplexes at enhancer-to-cmRNA v/w ratio of 4 and a dose of 5 µg hBMP-2- or tomato N1-cmRNAs/disc. (A) Fluorescence microscopy image of fat disc taken 24 hours after transfection with the complexes of tomato N1 cmRNA. The scale bars represent 500 µm. Induction of bone related gene expression after fat discs lipofection with DF-Gold/hBMP-2 cmRNA complexes. Fold increase in expression of (B) hBMP-2, (C) RunX2, (D) ALP and (E) Coll I. Total RNA was extracted and RT-PCR was performed 3 and 7 days after transfection. Expression is reported as fold induction compared to untransfected controls. All values were normalized to beta-tubulin. (*) Indicate significant difference between 3 and 7 days post-transfection for ALP and Coll I expression.

Figure 8:
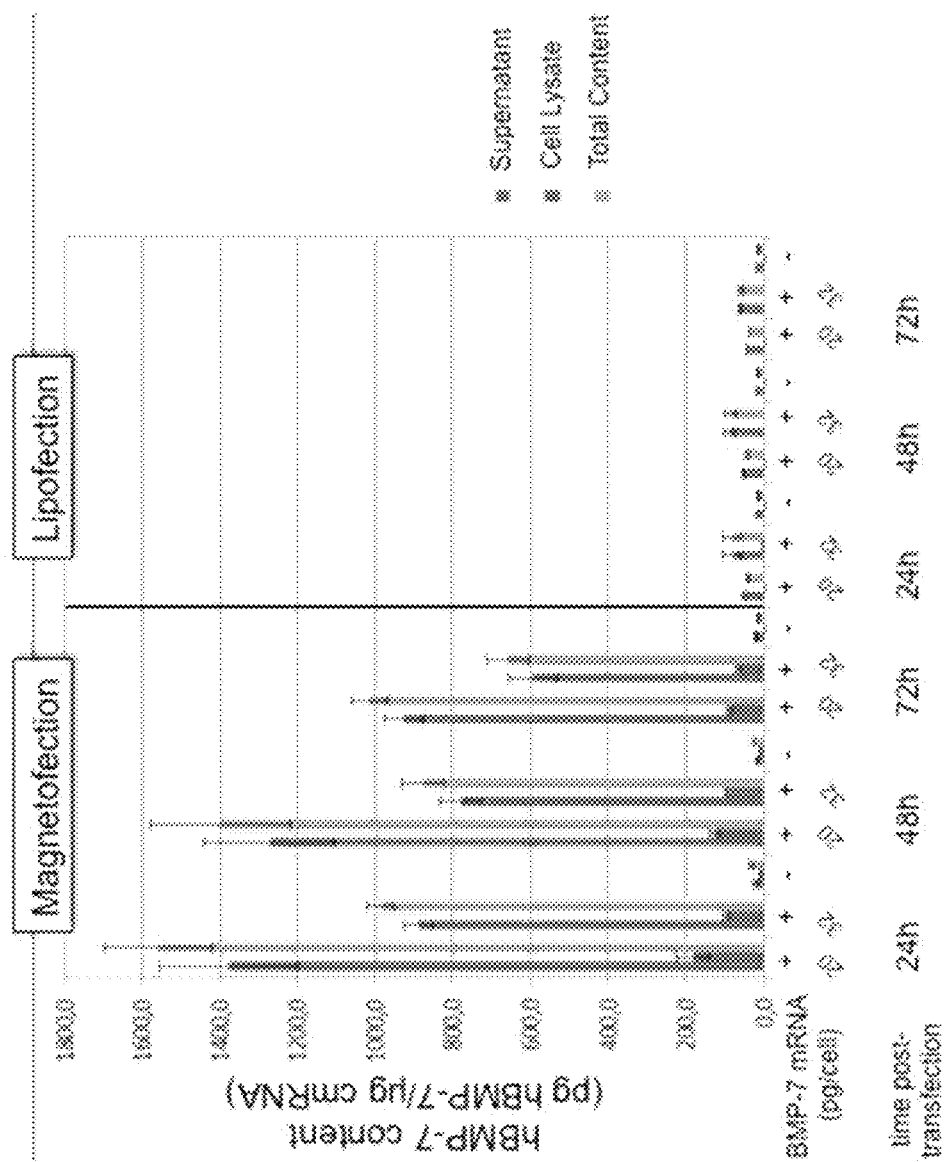

FIG. 8. hBMP-7 produced in AMSCs at different time points after transfection with DF-Gold/cmRNA lipoplexes and DF-Gold/SO-Mag6-115/cmRNA magnetic triplexes. The produced hBMP-7 was normalized to the applied hBMP-7 cmRNA dose (20 and 32 pg/cell).

Figure 9:
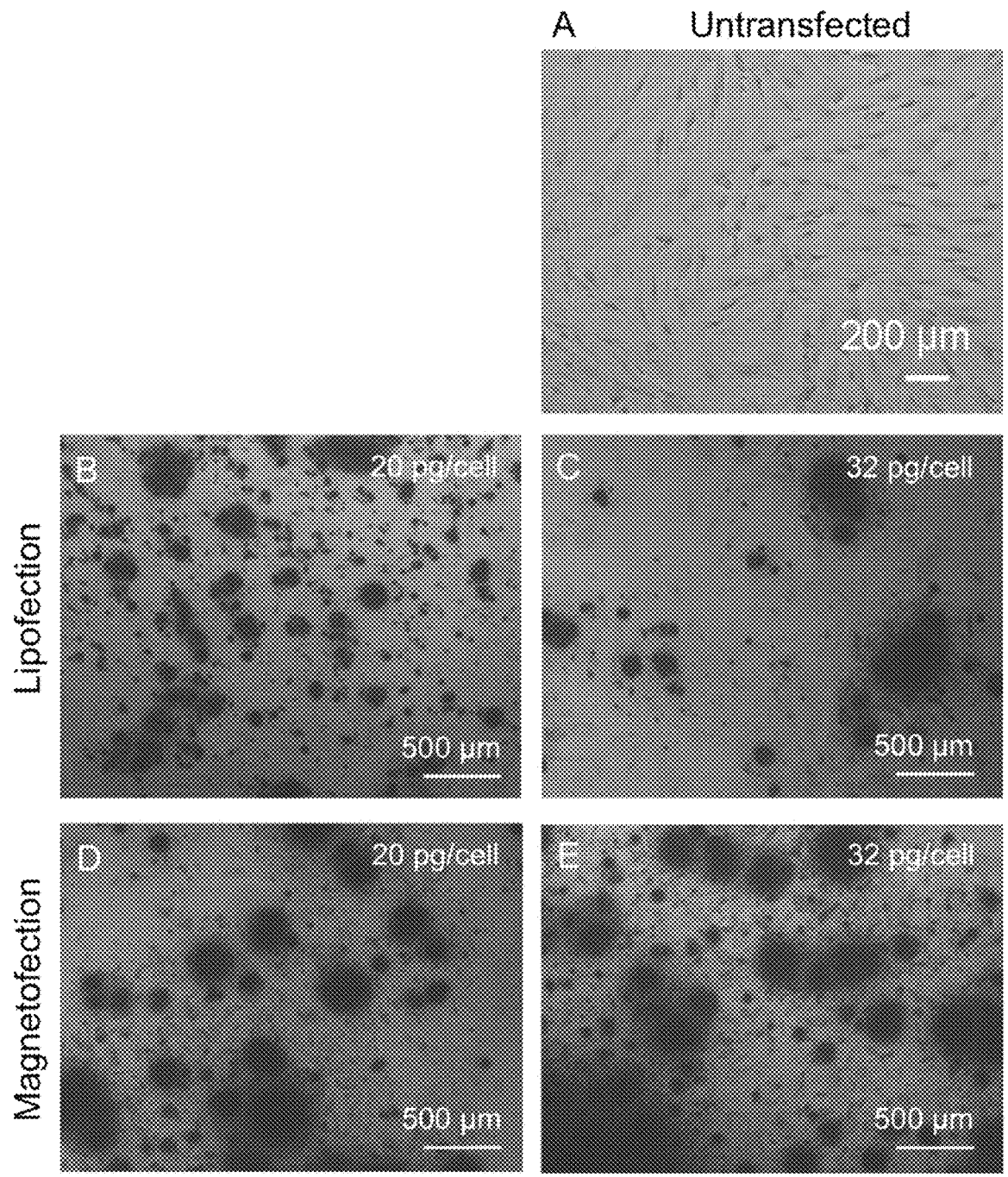

FIG. 9. Mineralization of AMSCs after lipofection with DF-Gold/hBMP-7 cmRNAs lipoplexes and magnetofection with SO-Mag6-115/DF-Gold/hBMP-7 cmRNA triplexes. The doses of cmRNA used were 20 and 32 pg/cell. Alizarin red staining 21 days after transfection: (A) untransfected cells, (B-C) cells after lipofection and (C-D) cells after magnetofection.

Figure 10:
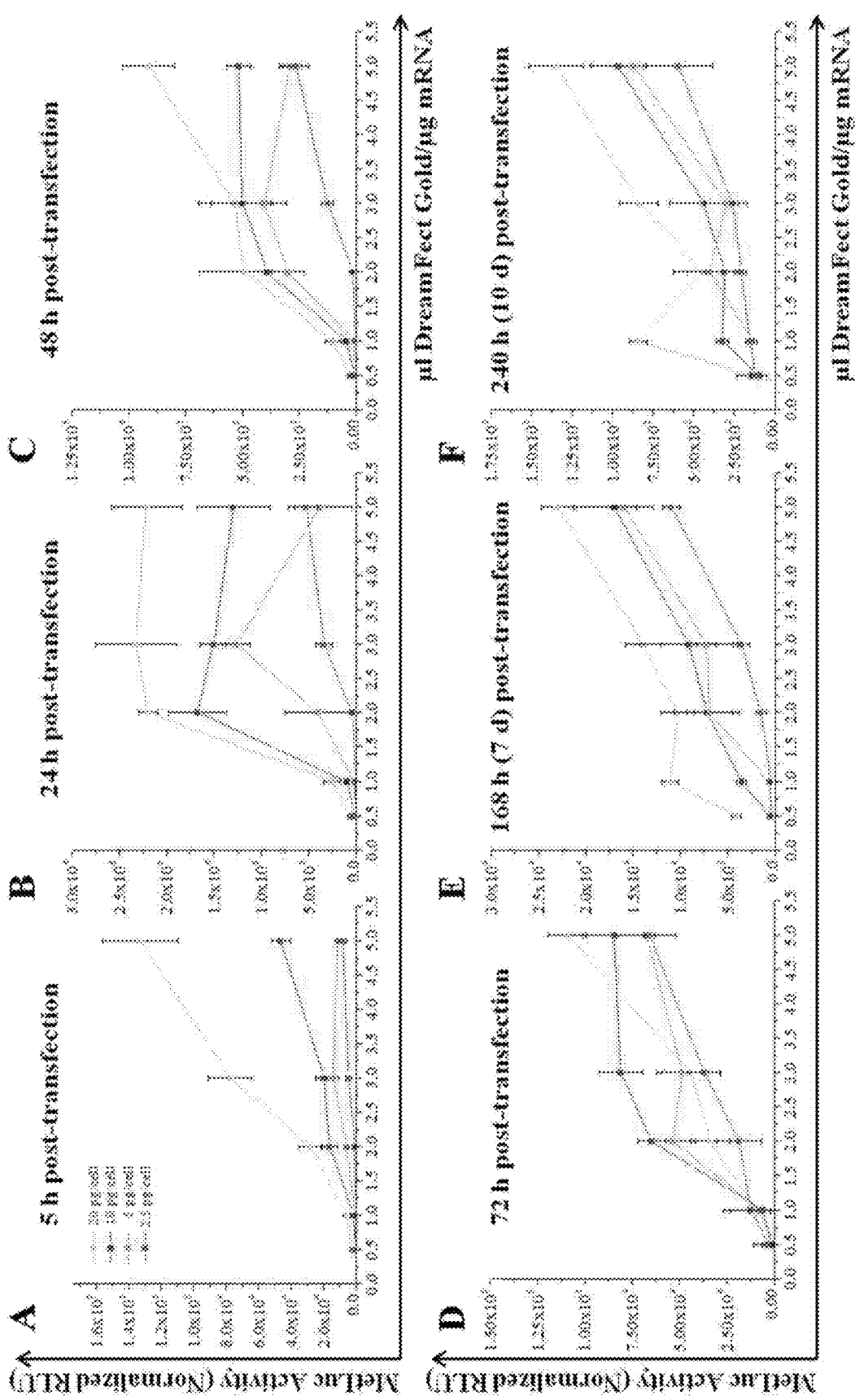

FIG. 10. MetLuc expression at different time points after transfection of AMSCs with DF-Gold/MetLuc mRNA lipoplexes. The DF-Gold-to-mRNA v/w ratio tested was in the range of 0.5 to 5 µl DF-Gold to µg mRNA at applied mRNA doses of 2.5, 5, 10 and 20 pg/cell.

Figure 11:
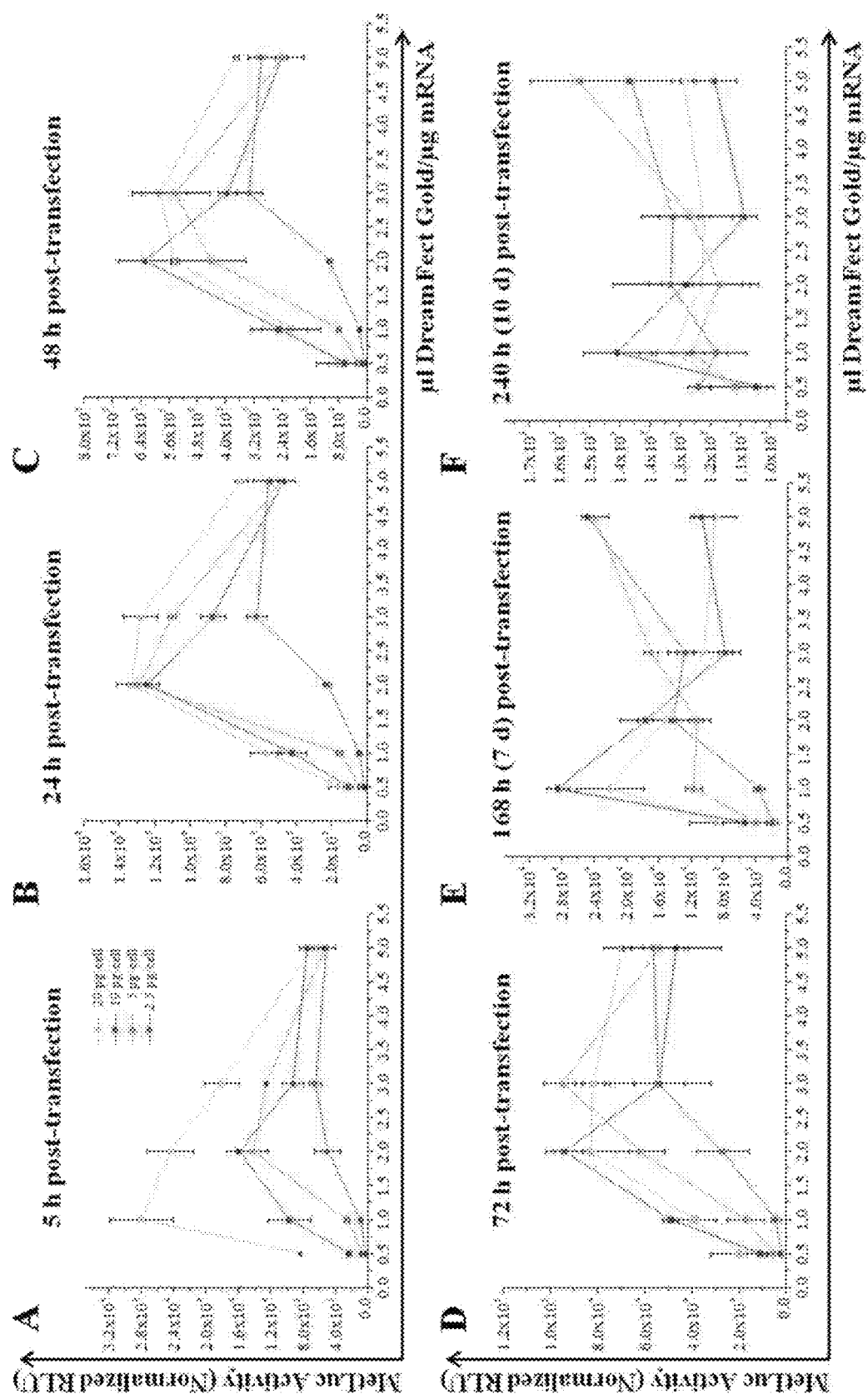

FIG. 11. MetLuc expression at different time points after transfection of BMSCs with DF-Gold/MetLuc mRNA lipoplexes. The DF-Gold-to-mRNA v/w ratios tested were in the range of 0.5 to 5 µl DF-Gold to µg mRNA at applied mRNA doses of 2.5, 5, 10 and 20 pg/cell.

Figure 12:
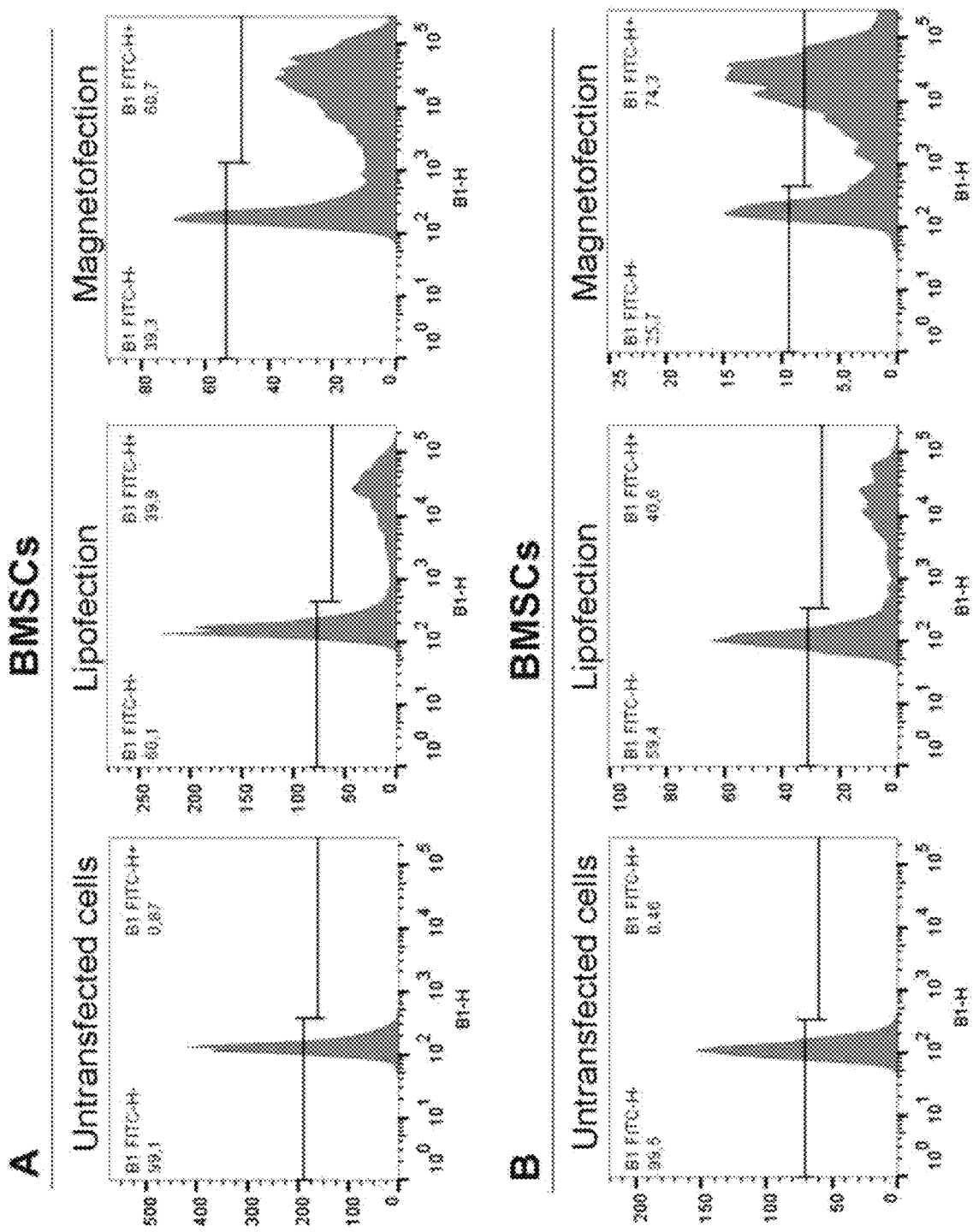

FIG. 12. Flow cytometry histograms for (A) AMSCs and (B) BMSCs 24 hours after transfection with DF-Gold/eGFP mRNA lipoplexes at DF-Gold-to-mRNA v/w ratio of 4 (Lipofection) and DF-Gold/SO-Mag6-115/eGFP mRNA magnetic triplexes at Fe-to-mRNA w/w ratio of 0.5 (Magnetofection).

Figure 13:
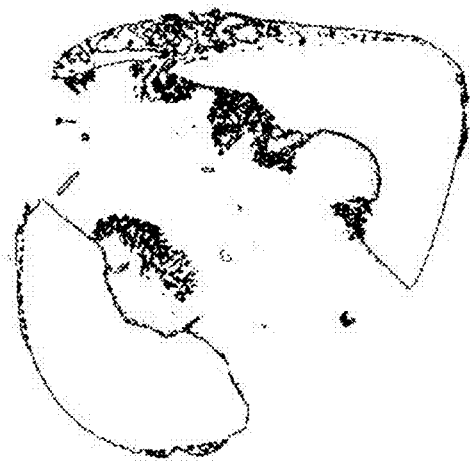
Figure 13:
Figure 13:
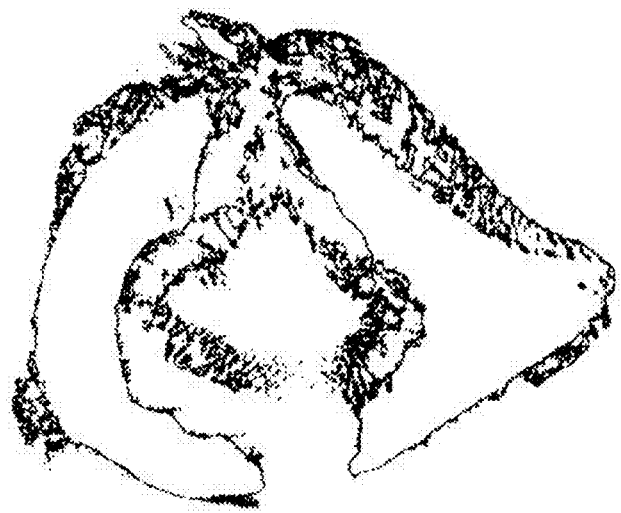
Figure 13:
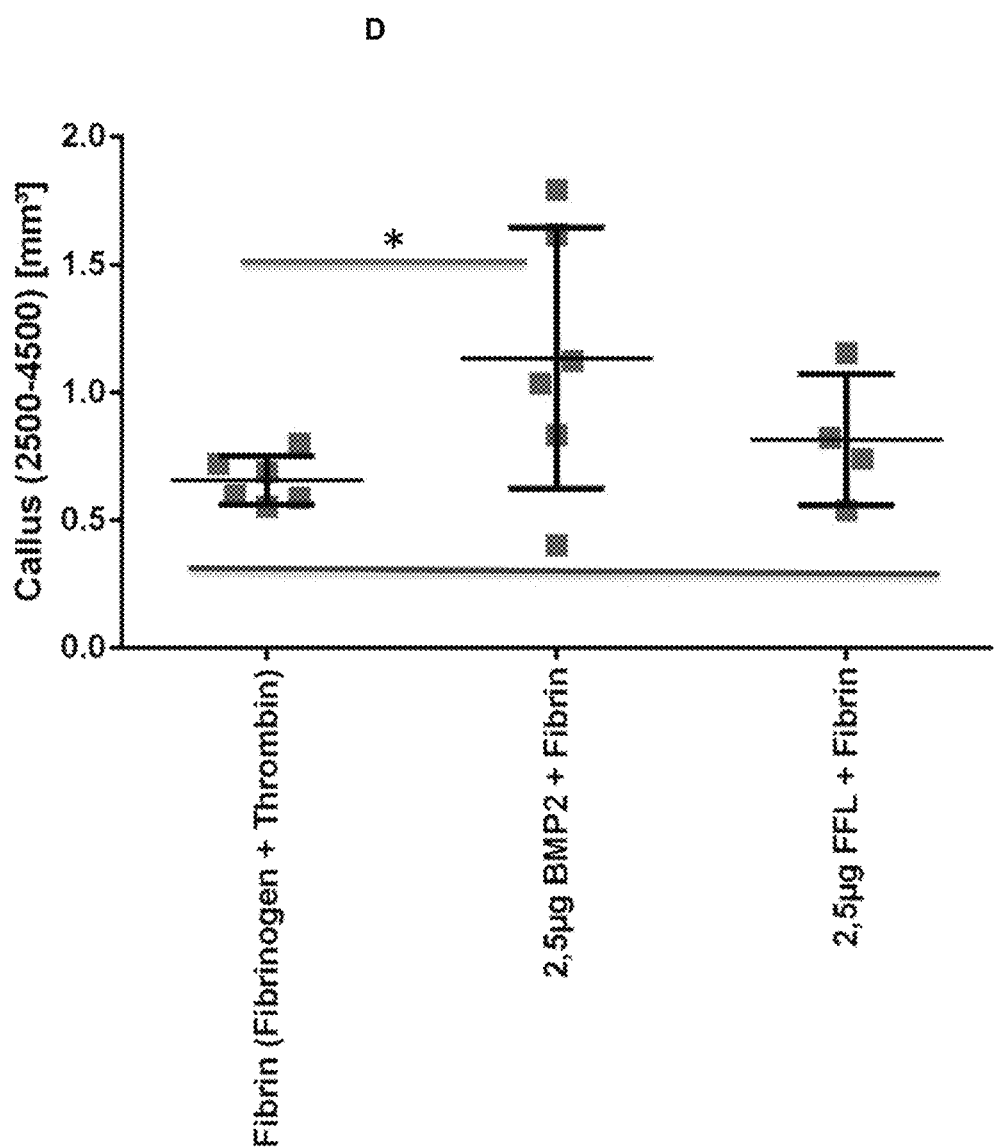

FIG. 13. BMP-2 RNA grafted onto bone implant materials—µ-CT results—whole bone. µCT 3D reconstruction and longitudinal sections obtained for all groups after 2 weeks of treatment. (A) fibrin, (B) C12-(2-3-2)/FFL cmRNA, and (C)C12-(2-3-2)/hBMP-2 cmRNA. Area of callus formation has been highlighted by setting up the same threshold values (2500-4500) in the ImageJ software for all the samples. (D) Amount of callus formation as quantified by ImageJ.

Figure 14A:
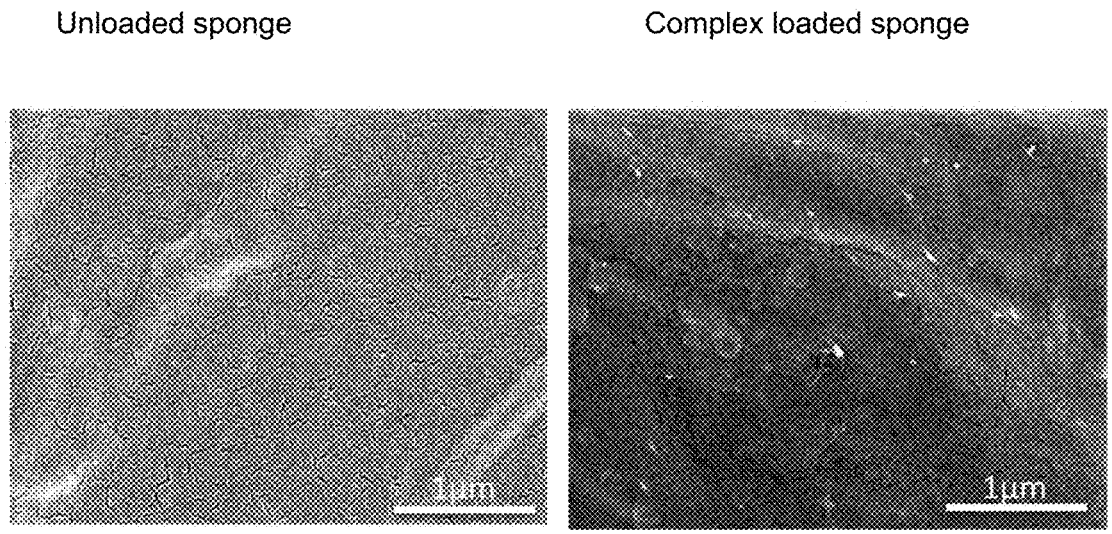
Figure 14B:
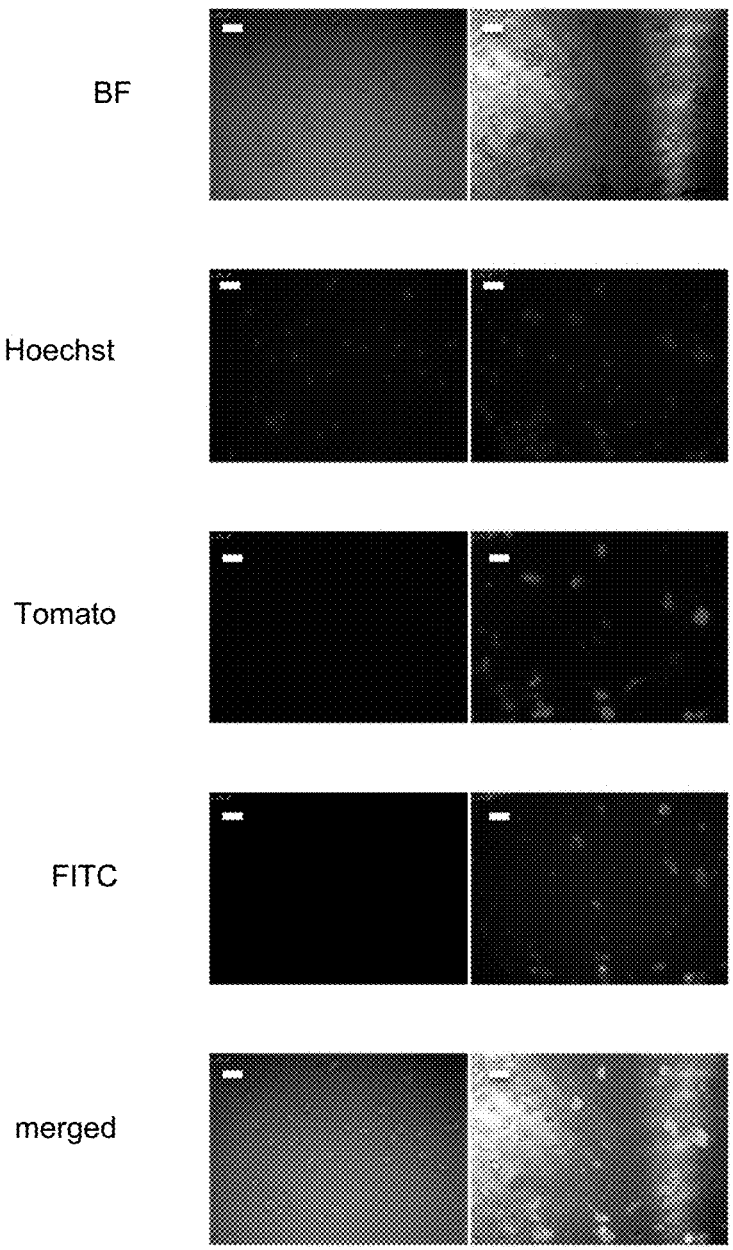
Figure 14C:
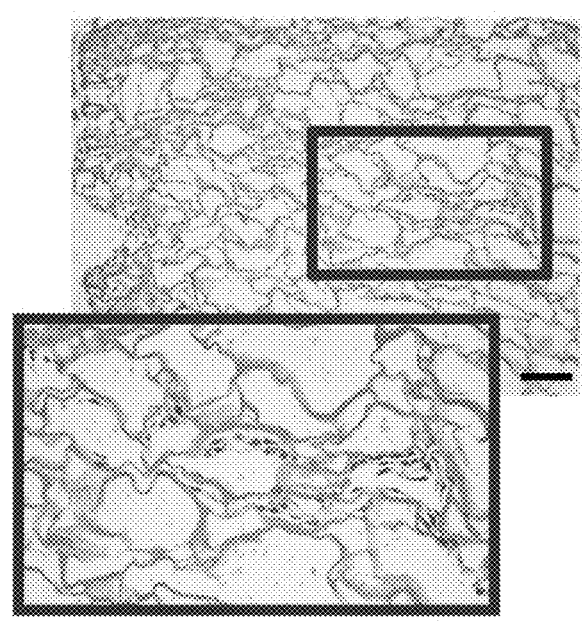

FIG. 14. Complex loading and cell seeding on collagen sponges. (A) Scanning electron microscopy of vacuum-dried collagen sponges, unloaded and loaded with Luc SNIM RNA lipoplexes (mean hydrodynamic diameter of lipoplex: 65.8 nm). (B) Fluorescence microscopy of NIH3T3 cells, 30 h after seeding on the collagen sponges loaded with tdTomato mRNA where 10% tdTomato mRNA was FITC labelled. (C) Hematoxylin staining of the NIH3T3 cells, 7 days after seeding on the collagen sponge. The nucleus of the cells were stained in dark blue with hematoxylin. Scale bar shows 100 µm. The left edge of the upper panel represents the surface of the collagen sponge.

FIG. 15. Transfection efficacy and cell viability at 48 h after seeding NIH3T3 cells on the collagen sponges loaded with eGFP mRNA-complexes. (A) Fluorescence microscopy with 4× magnification (JULY™): expression of eGFP mRNA in NIH3T3 cells. (B) FACS analysis: A clear shift of mean flourescent intensity in NIH3T3 cells transfected with 100 pg/cell eGFP mRNA, compared to untransfected cells. (C) FACS analysis: Correlation of mRNA dose with respect to transfection efficiency. (D) and (E) FACS analysis of PI staining and WST assay, respectively, indicate the cell viability around 60-70%. All data shown are mean±SD from the values of three replicates.

Figure 16:
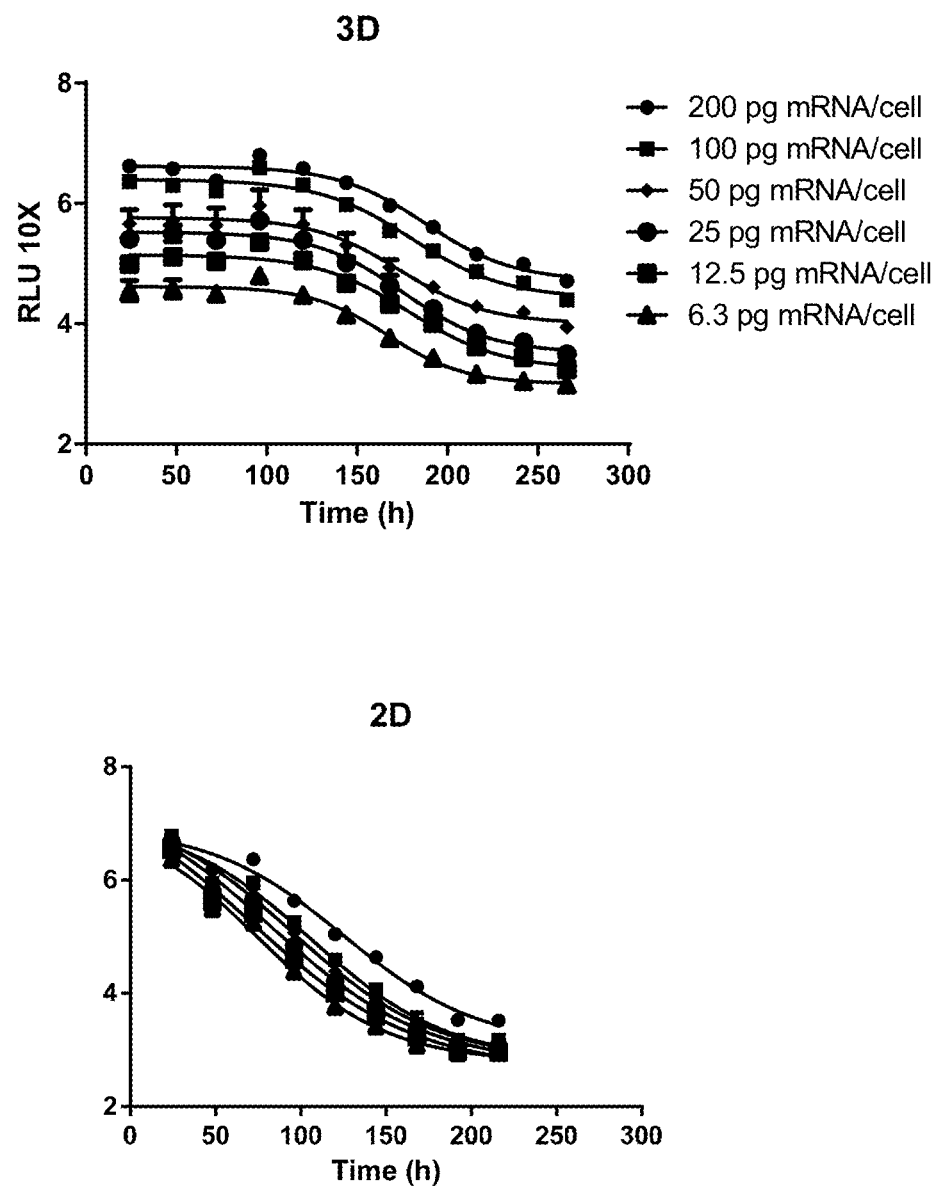

FIG. 16. Expression kinetics of Metridia luciferase mRNA in 2D versus 3D culture using NIH3T3 cells. Supernatants were collected every 24 h after transfection, and expression of Met luc was measured immediately. All data shown are mean±SD from the values of three replicates. Y axis is in logarithmic scale FIG. 17. Kinetics of Metridia luciferase expression in collagen sponges, using MSCs at different cell densities. Amount of mRNA lipoplexes used in this experiment was 50 pg/cell. Supernatants were collected every 24 h after transfection, and kept in −20° C. After 8 days, expression of Metridia luciferase was measured for all time points. Data shown are mean±SD from the values of three replicates. Y axis is in logarithmic scale.

FIG. 18. Immunohistochemistry analysis for in vivo bone regeneration. (A). Staining of mineralized bone tissue. Red rectangles show where the sponges placed in the femur defect. Black areas are highly mineralized. (B). Callus formation in periosteal area (C). Fraction of fibrous tissue formation. (D). Fraction of osteoid formation. Values compared using T-test (n=9).

Figure 19:
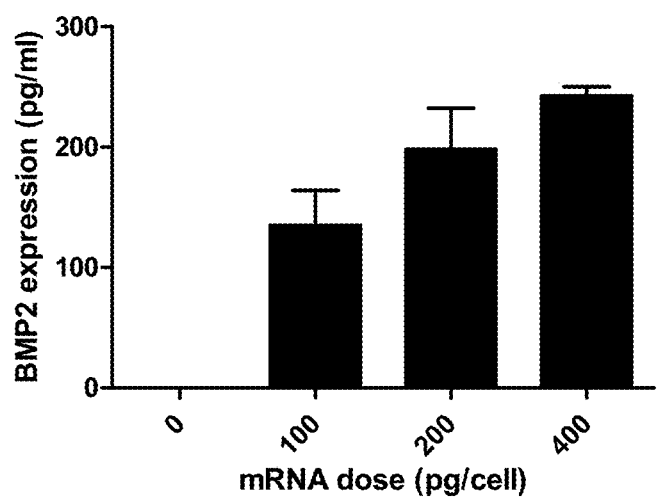

FIG. 19. Expression of hBMP2 by MSCs seeded on hBMP2 mRNA-loaded collagen sponges. Three different doses were tested. Data shown are mean±SD from the values of three replicates.

FIG. 20. In vitro bone differentiation. RT-qPCR results: Fold increase of expression of osteoblast markers at 7 and 14 days after seeding cells on hBMP2 cmRNA-loaded collagen sponges. Values are mean±SD from of three replicates (A). MC3T3-E1 cells: values were normalized to the expression of GAPDH. Data expressed as fold increase to untransfected cells in 3D. (B). MSCs: values were normalized to the expression of β-tubulin. Data expressed as fold increase to untransfected cells in 2D, and compared using multiple t-test.

Figure 21A:
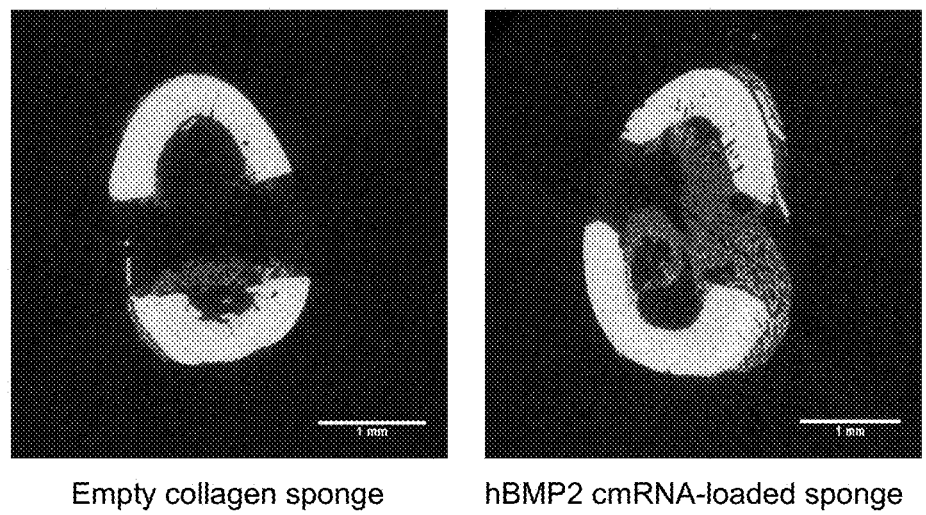

FIG. 21. In vivo bone regeneration. (A). µ-CT images of rat femur bone at 2 weeks after implantation. Red parts represent newly formed bone. (B). µ-CT analysis for evaluation of bone formation areas at 2 weeks after implantation. Values compared using t-test (n=9)

Figure 22:
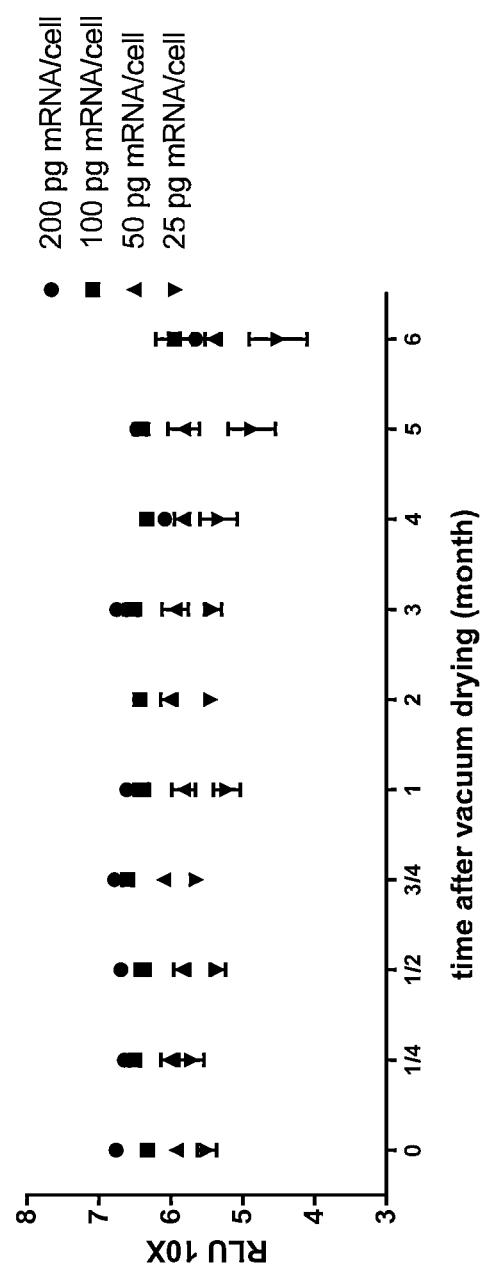

FIG. 22. Stability of vacuum-dried mRNA lipolelxes on collagen sponges. Metluc mRNA-loaded collagen sponges vacuum-dried for 2 h, then vacuum sealed and kept in RT. In different time points after vacuum-drying, plates opened and NIH3T3 cells were seeded on the sponges. Expression of Met Luc was measured 24 h after cell seeding. All data shown are mean±SD from the values of three replicates. Y axis is in logarithmic scale.

Figure 23:
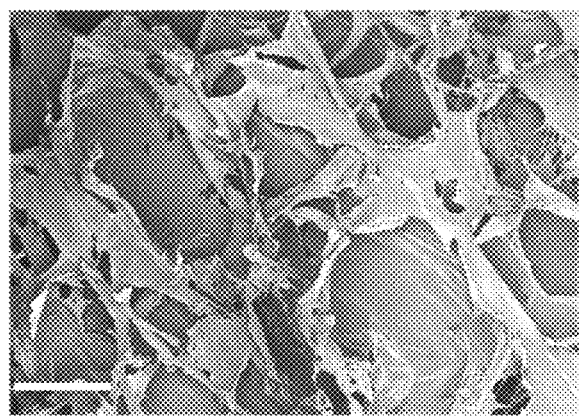
Figure 23:
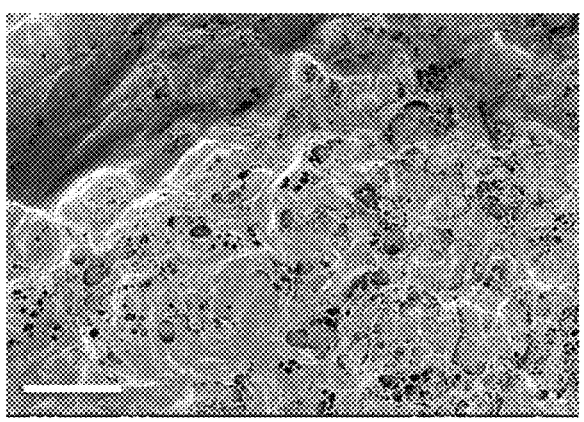

FIG. 23. SEM pictures form collagen sponges before and after vacuum-drying. Scale bars show 200 µm.

Figure 24:
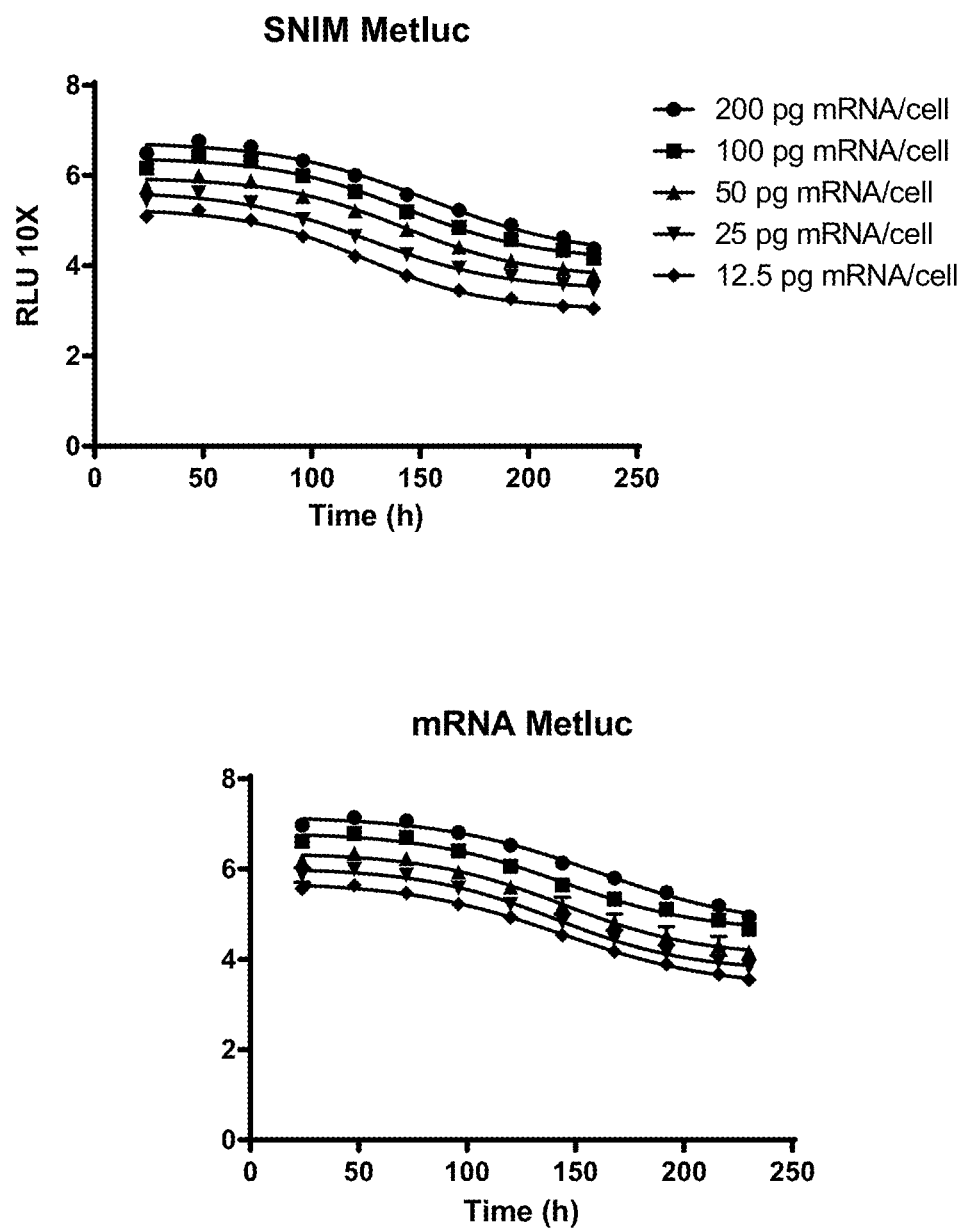

FIG. 24. Kinetics of Metluc expression post transfection either with SNIM Metluc or unmodified Metluc mRNA in NIH3T3 cells on the collagen sponges. Supernatants were collected every 24 h after transfection, and kept in −20° C. After 10 days, expression of Metridia luciferase was measured for all time points. Data shown are mean±SD of three replicates. Y axis is in logarithmic scale.

Figure 25:
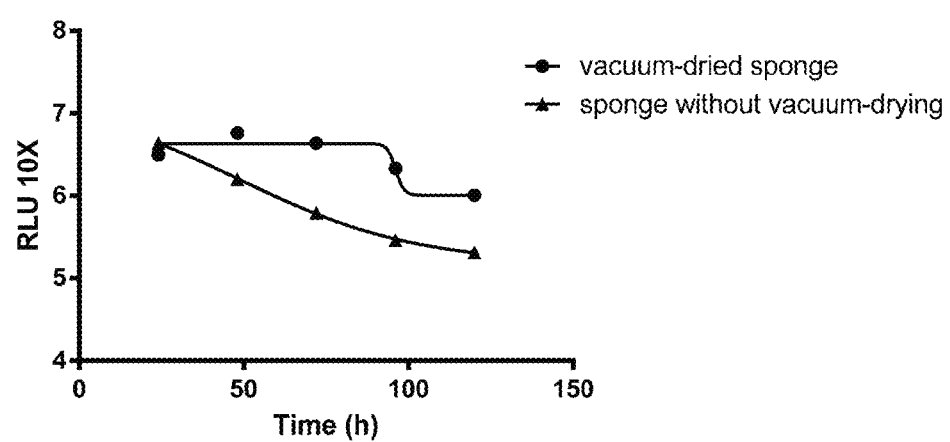

FIG. 25. Effect of vacuum-drying of sponges on kinetics of Metluc expression in NIH3T3 cells on collagen sponges. Supernatants were collected every 24 h after transfection, and kept in −20° C. After 5 days, expression of Metridia luciferase was measured for all time points. Data shown are mean±SD of three replicates. Y axis is in logarithmic scale.

Figure 26:
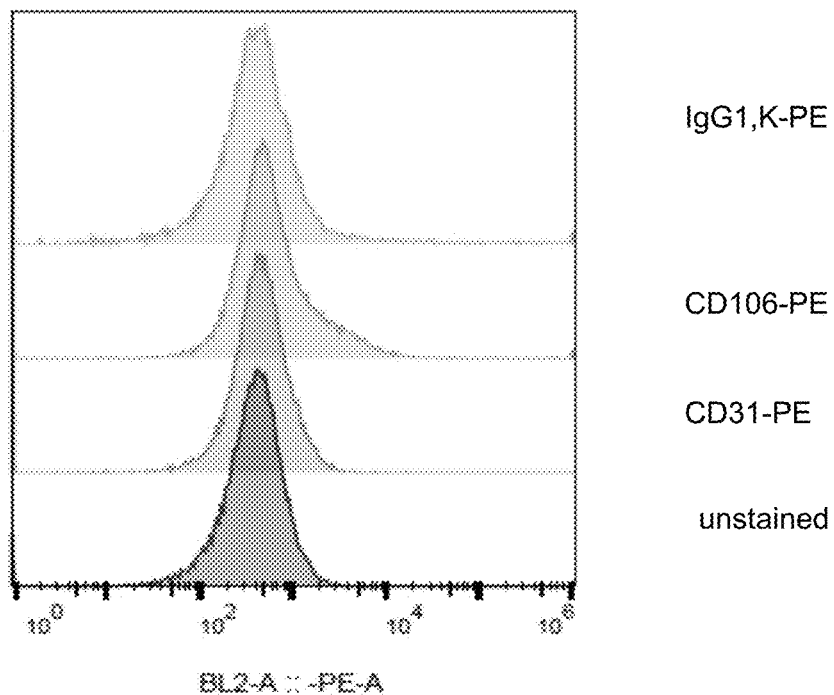

FIG. 26. FACS analysis: Investigation of positive (CD90 and CD29), and negative (CD45, CD106 and CD31) markers for MSCs after isolation from fat tissue of rat. IgM,K-FITC, IgG1,K-FITC and IgG1,K-PE have been used as controls.

Figure 27:
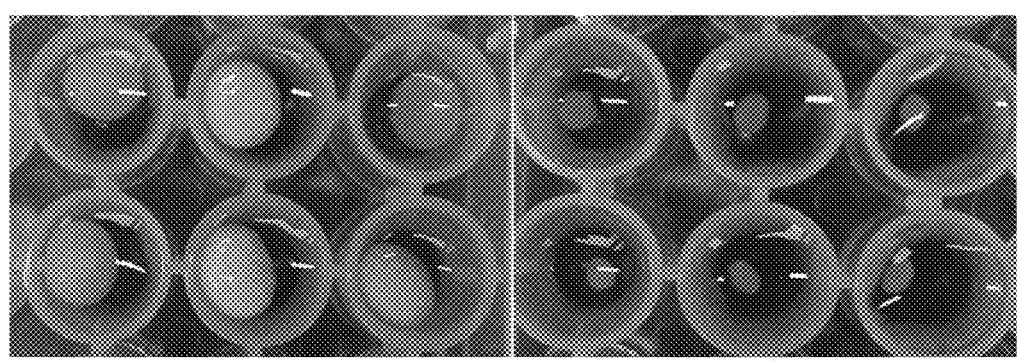

FIG. 27. Macroscopic changes is sponges' morphology during differentiation. Pictures were taken from the 96-well-plate, 7 days after seeding MSCs on the sponges.

Figure 28:
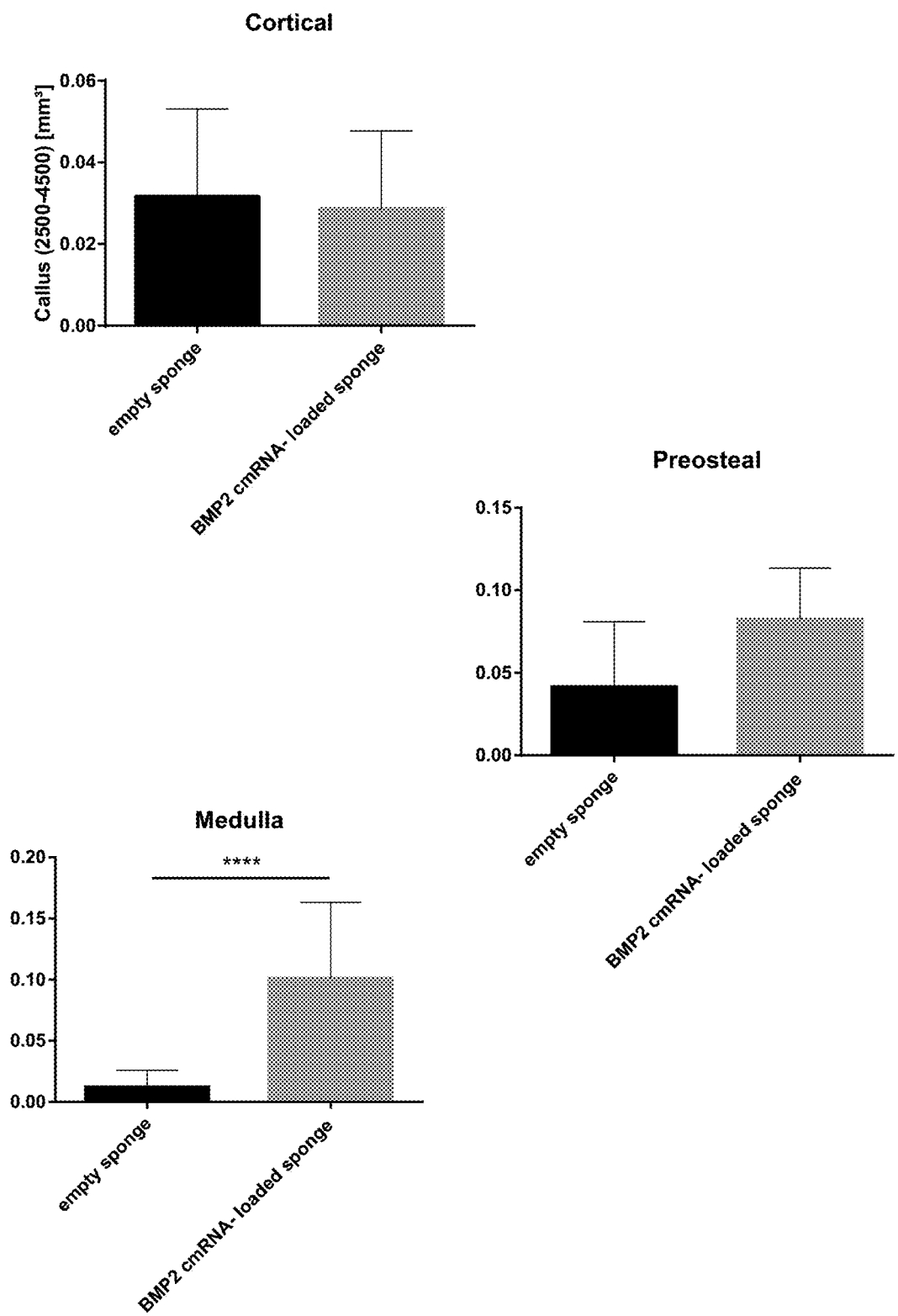

FIG. 28. In vivo osteogenic effect of collagen sponges loaded with hBMP2 cmRNA lipoplexes in different parts of bone. Values compared using T-test.

Figure 29:
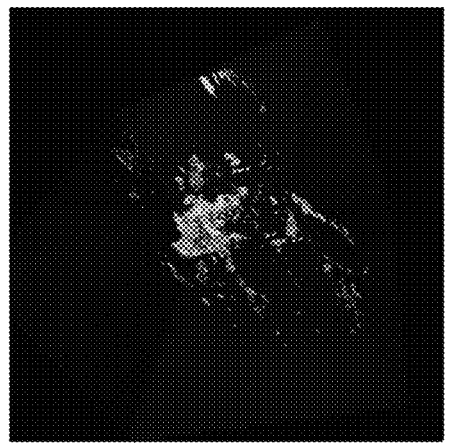
Figure 29:
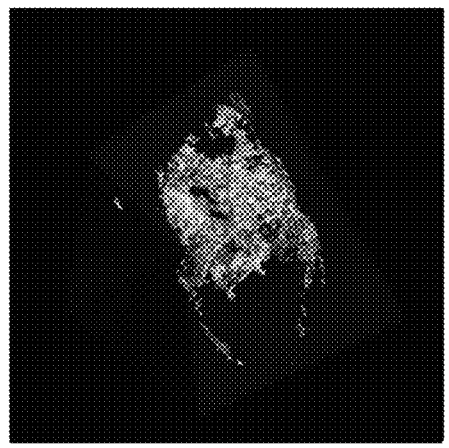

FIG. 29. µ-CT: the effect of hBMP2 cmRNA-loaded collagen sponges for bone regeneration in vivo, at two weeks after surgery. Yellow parts are newly formed bone.

FIG. 30. (A) Mineralization of Tissue significantly increases upon implants loaded with hBMP-2 coding cmRNA in the medulla of rat femurs. (B) Periostal tissue formation is significantly increased as a consequence to implantation of Collagen sponges loaded with hBMP-2 coding cmRNA. (C) Fibrous tissue per total volume (Fb.V/TV) is significantly increased upon treatment with Collagen sponges loaded with cmRNA for hBMP-2. (D) Formation of osteoids/per total volume (OV/TV) is increased upon treatment with Collagen sponges loaded with cmRNA coding for hBMP-2. (E) Less bone resorption is objected as a consequence to the implantation of Collagen sponges loaded with cmRNA coding for hBMP-2.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

Example 1

Materials & Methods (Especially Pertaining to Examples 1 to 7).

Materials. Dulbecco's Modified Eagle's Medium (DMEM), Dulbecco's Phosphate-Buffered Saline without Calcium and Magnesium (DPBS), Fetal Bovine Serum (FBS), Penicillin/Streptomycin (P/S) and Accutase solution were purchased from PAA Laboratories GmbH (Pasching, Austria). Opti-MEM medium and Collagenase type II were obtained from Gibco™ (Invitrogen, CA, USA). Ficoll-Paque™ was purchased from GE Healthcare Ltd. (CT, USA). Tetraethyl orthosilicate (TEOS), 3-(trihydroxysilyl) propylmethylphosphonate (THPMP) and branched Polyethylenimine (bPEI) were obtained from Sigma-Aldrich (MO, USA). Other reagents and materials were obtained from Sigma-Aldrich unless specified otherwise. A 24-well magnetic plate (OzBiosciences, Marseille, France) was used for magnetofection experiments.

Animals.

Female Sprague Dawley rats (250-300 g) were purchased from Charles River Laboratories (Sulzfeld, Germany) and used for both adipose and bone marrow mesenchymal stem cell isolation. The animals were euthanized by carbon dioxide asphyxia immediately before tissue collection. Procedures used were permitted by the local ethics committee and performed according to the German law for animal protection.

Isolation and Culture of Rat-Derived Mesenchymal Stem Cells.

Bone marrow mesenchymal stem cells (BMSCs) were isolated with a protocol previously described (Balmayor, Biores Open Access 2(5), 2013, 346-355). In brief, femurs and tibias were cleaned from all surrounding tissue, cut at both epiphyses and incubated in sterile DMEM containing 2.5 mg/ml collagenase type II at 37° C. and 5% $CO_2$ for 2 h. Once the bone marrow had been flushed out with complete DMEM (i.e. supplemented with 10% FBS and 1% P/S), cells were sedimented and resuspended in fresh complete DMEM. Subsequently, the mononuclear cell fraction was collected by density gradient centrifugation using Ficoll-Paque™ (500 g, 30 min), washed and resuspended in complete DMEM. Cells were plated at 3000 cells/cm$^2$. After 24 h in culture, the culture medium was replaced to remove non-adherent cells.

To isolate the adipose mesenchymal stem cells (AMSCs), fat tissue collected from the abdominal area was cut into small mm size pieces and transferred to a falcon tube containing sterile DPBS. After several washing steps with DPBS, the fat pieces were incubated in 0.5 mg/ml collagenase type 11 solution at 37° C. for 30 min. Next, complete DMEM culture medium was added to stop the collagenase action and the mixture was centrifuged at 600 g for 10 min. The obtained cell pellet was re-suspended in complete DMEM culture medium and the cell suspension was filtrated through a 40 µm cell strainer (BD Falcon, NJ, USA) and plated at 3000 cells/cm$^2$.

Both cell types, BMSCs and AMSCs, were expanded and cultured at 37° C. and 5% $CO_2$ by using complete DMEM. For transfection and differentiation experiments the cells were used up to passage 6. During cultivation, the medium was changed every third day and the cells were maintained at 37° C. and 5% $CO_2$. Characterization of both MSCs isolated was performed by following the described protocols as published by Balmayor (2013, loc. cit.).

Ex Vivo Human Adipose Tissue Culture.

Fresh human subcutaneous adipose tissue was obtained from healthy patients undergoing reconstructive surgery with written informed patient's consent approved by the local ethical committee of the University Hospital "Klinikum rechts der Isar" at the Technical University of Munich, Germany. Human adipose tissue was dissected out from skin and vessels under sterile conditions. Subsequently, tissues were carefully cut into approximately 1 mm thick slices. Next, a skin biopsy punch (3 mm) was used to punch out uniform 3 mm×1 mm circular explants following protocol described by Evans (2009, loc. cit.). Resulting tissue explants were washed three times with sterile DPBS and placed in 35 mm diameter Petri dishes. Subsequently, they were cultured at 37° C. and 5% $CO_2$ in complete DMEM for up to 7 days. Culture media changes were performed, first after 2 hours and thereafter every 24 hours of culturing, to ensure well-oxygenated conditions (Puri, J Lipid Res 48(2), 2007, 465-471).

Synthesis of Iron Oxide Silica Magnetic Nanoparticles.

Iron oxide silica core-shell magnetic nanoparticles were synthesized as previously described (Mykhaylyk, Liposomal magnetofection. In: Weissig V (ed.) Liposomes, Methods in Molecular Biology, vol. 605. Humana Press-Springer, New York 2010, 487-525; Mykhaylyk, Pharm Res 29(5), 2012, 1344-1365). First, precipitation of the Fe(II)/Fe(III) hydroxide from an aqueous solution of iron salts and transformation into magnetite "core" nanoparticles was carried out. Subsequently, the surface of the nanoparticles was stabilized by means of co-condensation of tetraethyl orthosilicate (TEOS) and 3-(trihydroxysilyl) propylmethylphosphonate (THPMP) resulting in a silicon oxide coating with surface phosphonate groups. Finally, 25-kD branched polyethylenimine aqueous solution pH7.0 was applied at a PEI-to-iron w/w ratio of 11.5% to decorate the surface of the particles. The resulting magnetic nanoparticles with a SiOx/Phosphonate-PEI coating will be further referred as SO-Mag6-115 MNPs or as MNPs. Detailed physico-chemical characterization of these nanoparticles has been reported by Mykhaylyk (loc. cit.). Briefly, the particles have mean hydrated diameter $Dh=97\pm14$ ($PDI=0.32\pm0.03$) and electrokinetic potential $\zeta=+34.1\pm2.7$ when suspended in water as determined by dynamic light scattering (DLS) using a Malvern Instruments Zetasizer Nano ZS (Herrenberg, Germany).

Generation of Chemically Modified Messenger RNA Encoding MetLuc, eGFP, Tomato and Human BMP-2.

Plasmid vectors containing codon-optimized open reading frames of *Metridia* luciferase (*Metridia longa*) and human BMP-2 mRNA were synthesized and cloned into BamHI-EcoRI sites of pVAXA120 by GeneArt (Life Technologies, CA, USA). eGFP was excised from peGFP-N1 (Clontech, CA, USA) using NotI-HindIII and cloned into EcoRI-HindIII of pVAXA120 via semi-blunt ligation. Coding sequence for Tomato was excised with NotI-KpnI from ptd Tomato-N1 (Clonetech, CA, USA) and ligated into EcoRI-KpnI sites of pVAXA120 via semi-blunt ligation. The vector pVAXA120 has been described previously (Kormann, Nat Biotechnol 29(2), 2011, 154-157) and was constructed by cloning a stretch of 120 As between PstI-NotI sites of pVAX1 (Invitrogen, CA, USA).

To generate templates for in vitro transcription (IVT), the above-mentioned plasmids DNA (pDNA) (i.e. pVAXA120-MetLuc, pVAXA120-eGFP, pVAXA120-Tomato or pVAXA120-hBMP-2) were linearized by restriction digestion with NotI. Template pDNA was further purified by chloroform ethanol precipitation. IVT was carried out with the RiboMAX™ Large Scale RNA Production System-T7 (Promega, WI, USA). For synthesis of capped mRNA, an anti-reverse cap analogue (ARCA, $m^{7,3'-O}GpppG$, Jena Biosciences, Jena, Germany) was used to ensure incorporation of cap only in the desired orientation. To generate modified mRNAs, 25 percent of cytidine-5'-triphosphate and uridine-5'-triphosphate were replaced by 5-methylcytidine-5'-triphosphate and 2-thiouridine-5'-triphosphate (Jena Biosciences, Jena, Germany). Purification of resulting modified mRNAs was performed by ammonium acetate precipitation. Integrity and sizes of the produced modified mRNAs were confirmed by native agarose gel electrophoresis.

Formation and Characterization of Transfection Complexes.

Lipoplexes and polyplexes were always freshly prepared by mixing selected lipid transfection reagents, e.g. Lipofectamine2000 (Invitrogene, CA, USA), DreamFect Gold (DF-Gold) and Dogtor (OzBiosciences, Marseille, France) or bPEI, with respective cmRNAs. The used volume-to-weight ratios of liposomal transfection reagents to cmRNA were chosen according to the manufacturers' instructions (i.e. 2 μl Lipofectamine2000 or 4 μl DF-Gold or 4 μl Dogtor, respectively, per μg mRNAs). In the case of bPEI, a 10 mg/ml solution in water was prepared and the pH was adjusted to 7.0 prior to use. Complexes were formed by mixing bPEI and cmRNA solutions at N/P=8 followed by an incubation for 20 minutes at room temperature to allow complex assembling. To prepare magnetic lipoplexes equal volumes of SO-Mag6-115 MNPs aqueous suspension (0.1 μg Fe/μl) and DF-Gold dilution (80 μl DF-Gold diluted to 100 μl with water) were mixed. Subsequently, equal volume of cmRNAs dilution (0.2 μg/μl water or 150 mM NaCl or non-supplemented Opti-MEM) was added, mixed carefully and the mixture was kept at room temperature for 20 minutes. The resulting ratio of the components in the SO-Mag6-115/DF-Gold/cmRNAs complexes was of 0.5:4:1 (iron weight/volume/weight). The complexes were characterized with regard to their mean hydrodynamic diameters (Dh), polydispersity index (PDI) and zeta potentials ($\zeta$) using DLS methods (Table 1).

Transfection Protocol in AMSCs and BMSCs.

For transfection, AMSCs and BMSCs were seeded at $1.25 \times 10^4$ cells/cm$^2$ in 24-well plates. After 24 hours incubation, cell culture medium was replaced with fresh non-supplemented Opti-MEM. 100 μl of lipoplexes or bPEI-complexes, containing 20 pg/cell cmRNAs (i.e. MetLuc, eGFP or tomato cmRNAs), were prepared as described above and added to the cells. 5 hours after transfection, medium was replaced with complete DMEM. The cells were further cultured under standard conditions for up to 10 days until results evaluation. To further increase transfection efficacy, SO-Mag6-115 MNPs were associated with lipid transfection reagent and cmRNA into magnetic SO-Mag6-115 particles/DF-Gold/cmRNAs lipoplexes at an iron weight/volume/weight ratio of 0.5:4:1 as described above. For transfection, 100 μl of magnetic lipoplexes containing 20 pg cmRNAs/cell (i.e. MetLuc, eGFP or tomato cmRNAs) were added to the AMSCs or BMSCs in culture and a magnetic field was applied by placing the cell culture plate on top of a 24-well magnetic plate for 30 minutes. Next, the magnetic plate was removed and the transfection was allowed to continue. All transfections through the entire study were performed in triplicates. To quantatively characterize the effect of magnetofection on transfection efficacy, the MAI was calculated as follows:

$$MAI = \left(\frac{AUC_{MF}}{AUC_{LF}}\right) \quad (1)$$

where AUC represents the area under the curve values for the kinetics of target protein (MetLuc and hBMP-2) expression after magnetofection (MF) and lipofection (LF), respectively.

One of the aims of the study was comparing AMSCs and BMSCs in terms of transfection efficiency. Thus, the used volume-to-weight ratios of liposomal transfection reagents to mRNA were chosen according to the manufacturers' instructions to be equal for both cell types. However, an optimization of the transfection protocol was further performed for both cells using DF-Gold-to-cmRNA ratios from 0.5 to 5 µl of the transfection reagent per µg nucleic acid at doses of 2.5, 5, 10 and 20 pg/cell. See details in FIGS. 10 to 12 and in the respective example parts.

Evaluation of the *Metridia* Luciferase Activity in Transfected Cells.

*Metridia* luciferase catalyzes the oxidation of coelenterazine to produce coelenteramide, $CO_2$ and light ($\lambda_{max}$ 480 nm). Based on this reaction, coelenterazine can be used as substrate for the detection of many secreted luciferases (Inouye, Protein Expr Purif 88(1), 2013, 150-156). In the study, native coelenterazine (Synchem OHG, Felsberg, Germany) was used to assay the MetLuc activity. Briefly, an equal volume per 50 µl of supernatant (collected from transfected cells at 5 hours, 1, 2, 3, 5 and 7 days after transfection) and coelenterazine solution (50 µM in degassed sodium phosphate buffer at pH 7.0) were mixed in a white opaque 96-well plate. Luminescence intensity was measured in light units per unit time or relative light units (RLU) at room temperature using a PerkinElmer Wallac Victor 1420 multilabel counter (MA, USA). All samples were measured in triplicates. MetLuc activity was expressed in Normalized Relative Light Units calculated using the following equation:

$$\text{Normalized } RLU = \left(\frac{RLU}{V_1}\right) \cdot V_2 \quad (2)$$

where the RLU are the values obtained from the equipment, $V_1$ corresponds to the volume of supernatant collected to perform the measurement and $V_2$ is the total supernatant volume in ml.

Enhanced Green Fluorescent Protein (eGFP) Positive Cells.

To evaluate the transfection efficiency in terms of percentage of eGFP-positive cells, transfected cells with eGFP cmRNA were analyzed by flow cytometry. For this, 24 hours after transfection the cells were washed twice with DPBS and detached by using 100 µl accutase per well of 24-well plate. Subsequently, the cell culture plate was centrifuged at 500 g for 10 minutes and the cells were resuspended in DPBS (2% FBS). Flow cytometry analyses were performed on a MACSQuant Analyzer (Miltenyi Biotech, Bergisch Gladbach, Germany) collecting at least 5,000 events per sample.

Enhanced Green Fluorescent Protein (eGFP) and Tomato Expressing Cells.

AMSCs and BMSCs transfected with eGFP and tomato cmRNAs were imaged, at 24 hours post-transfection under the fluorescence microscope (Biorevo BZ9000, Keyence, Osaka, Japan).

Cytotoxicity Screening of the Complexes of Chemically Modified mRNA.

Cytotoxicity screening was performed by transfecting AMSCs with different MetLuc cmRNA complexes followed by analysis of cell respiration activity (viability) 5 and 24 hours after transfection using a standard MTS assay performed in triplicates according to the manufacturer's instructions (CellTiter 96, Promega, WI, USA). For experimental details see herein elsewhere.

BMP-2 Production by Transfected Cells.

Lipofection and magnetofection protocols described above were used to deliver the hBMP-2 cmRNA into AMSCs. Transfections were performed using 20 or 32 µg hBMP-2 cmRNA/cell. At defined time points, levels of secreted and cell associated human BMP-2 were determined in supernatant and cell lysates, respectively, by enzyme-linked immunosorbent assay (ELISA, Quantikine, R&D Systems, MN, USA) according to the manufacturer's instructions. The absorbance was measured at 450 nm in a PerkinElmer Wallac Victor 1420 multilabel counter (MA, USA). Wavelength correction was set at 570 nm. Experiments were performed in triplicates, and the protein content was determined using a standard curve (range: 0-4000 µg/ml hBMP-2).

In addition, cells were also transfected in the presence of osteogenic medium (i.e. 2% FBS, 10 mM β-Glycerophosphate, 200 µM Ascorbic acid). The osteogenic medium was prepared without dexamethasone. Thus, relevant information could be obtained related to the osteogenic capacity of cell-released hBMP-2 in further experiments.

Transfection of hBMP-2 cmRNA into Primary Human Tissue.

Explants transfection was performed following a protocol previously described by Evans (2009, loc. cit.) with slight modifications. Briefly, washed human adipose tissue discs were placed into 48-well plates and transfected with 5 µg hBMP-2 cmRNA or tomato cmRNAs using DF-Gold lipoplexes (4 µl DF-Gold/1 µg cmRNA). 80 µl suspension containing the complexes was directly injected into the tissue discs. The plates were returned to the incubator for 1 hour. Afterwards, 500 µl fresh, non-supplemented Opti-MEM was added to each well containing transfected explants and incubation continued for further 5 hours. Culture medium was then changed to osteogenic medium and the explants were further cultured as previously described for 3 and 7 days. All transfection of the tissue explants were conducted on freshly collected tissue and under sterile conditions. Adipose tissue discs transfected with tomato cmRNAs were imaged, at 24 hours post-transfection under the fluorescence microscope (Biorevo BZ9000, Keyence, Osaka, Japan).

In Vitro Osteogenesis.

hBMP-2 cmRNA-transfected AMSCs were cultured under osteogenic stimulation to evaluate the ability of the hBMP-2 cmRNA in inducing in vitro osteogenesis. Both, lipofection and magnetofection methods were used to transfer the hBMP-2 cmRNA into the cells as previously described. 5 hours post-transfection, the medium was exchanged with osteogenic medium without dexamethasone. Transfected cells were maintained under osteogenic medium for up to 21 days and the medium was partially changed every 3 days (i.e. half volume was replaced with fresh osteogenic medium). Untransfected cells, cultivated under the same conditions, were used as a control. In vitro osteogenesis was followed by evaluating the expression of osteo-related genes and the occurrence of mineralization.

Alkaline Phosphatase (ALP) Activity.

Alkaline phosphatase activity was evaluated at days 3, 7 and 12 post-transfection. For this purpose, an alkaline phosphatase colorimetric assay (Abcam, Cambridge, UK) was used following the manufacturer's instructions.

The assay is based on the use of p-nitrophenyl phosphate (pNPP) as a phosphatase substrate. pNPP is dephosphorylated in the presence of ALP. As a result, yellow p-nitrophenol (pNP) compound is formed, which is characterized by a maximum absorbance at 405 nm. The ALP assay was performed based on the manufacturer's protocol. Briefly, transfected cells were washed twice with DPBS and subsequently incubated with assay buffer for 20 minutes at room temperature. After a good homogenization of the cell monolayer, the samples were centrifuged to remove insoluble material. pNPP solution was added to samples and control samples and incubated at room temperature for 60 minutes and protected from the light. The pNP production was determined by measuring the absorbance at 405 nm using a multilabel counter, as already described above. The pNP content values were calculated based on a standard curve. Triplicates were evaluated in all cases.

Furthermore, ALP was stained in fixed cells by incubation with the staining mixture of Fast blue B salt and Naphthol AS-MX phosphate (Cox, J Histochem Cytochem 47(11), 1999, 1443-1456) for 30 minutes at 37° C. The staining solution was washed out with DPBS and cells were analyzed under the microscope. Areas that were stained in purple were considered as positive.

Quantitative Real-Time PCR.

3, 7, 14 and 21 days after hBMP-2 cmRNA transfection, cells were washed twice with DPBS and subsequently lysed by TRIzol (Life technology, CA, USA). Total RNA was isolated based on phenol/chloroform method. RNA concentration and purity were determined spectrophotometrically using a BioPhotometer plus UV spectrophotometer (Eppendorf AG, Hamburg, Germany). First-strand cDNA was reverse-transcribed from total RNA by the use of First Strand cDNA Synthesis Kit (Thermo Scientific, MA, USA) according to the manufacturer's instructions. The expression of osteo-related genes was determined by means of real-time quantitative reverse transcription polymerase chain reaction (RT-PCR). Amplification primers are listed in the Table 2. SsoFast Eva Green Supermix (Bio-Rad Laboratories Inc., CA, USA) was used and real time PCR was carried out on a Bio-Rad CFX96 thermal cycler (Bio-Rad Laboratories Inc., CA, USA).

In the case of transfected adipose tissue, total RNA was extracted 3 and 7 days after transfection. Washed tissues were collected in RNA/ater reagent (Qiagen GmbH, Hilden, Germany) according to the manufacturer's protocol. Prior to RNA extraction, tissues were homogenized in TRIzol by the use of a handheld homogenizer (PT1200E Polytron, Kinematica GmbH, Eschbach, Germany). RNA extraction, cDNA synthesis and RT-PCRs were performed using the same protocols mentioned above for the cell. Expression levels of hBMP-2, RunX2, ALP and Coll I were analyzed. Amplification primers are listed in the Table 3.

Overall, beta-tubulin was selected as a reference gene. Data were expressed as fold induction relative to controls, i.e. untransfected cells and tissues respectively.

Alizarin Red Staining and Quantification.

14 and 21 days post-transfection, Alizarin red staining was performed to evaluate calcium deposits in the cells transfected with the hBMP-2 cmRNA complex. These calcium deposits would be indicators for osteogenic differentiation of the AMSCs. In brief, ethanol-fixed cells were incubated with Alizarin red solution (5 mg/mL in DPBS) for 15 minutes at room temperature. Stained cells were washed extensively to remove unspecific staining and/or possible precipitates. Mineralized nodules and calcium deposits are stained as red spots indicating osteogenesis. The Alizarin red dye was subsequently extracted with 100 mM cetylpyridinium chloride at room temperature for 3 hours. Absorbance was then measured at 570 nm. Experiments were performed in triplicates and the results are reported in comparison to untransfected control cells.

Statistical Analysis.

All the obtained values are reported as mean±standard deviation. Statistical analysis was performed using GraphPad Prism version 6.00, (GraphPad Software, CA, USA). Normal distribution of the data was analyzed by applying the Shapiro-Wilk test. One-way ANOVA followed by Tukey's multiple comparisons test was performed to analyze MetLuc expression of transfected cells via different transfection reagents (FIG. 2A) and flow cytometry results (FIG. 3C). In addition, Student's t test was used in the case that two independent samples were analyzed. All statistical analysis was performed following the recommendations of the software used. Probabilities of $p<0.05$ were considered as significant. Area under the curve (AUC) values were calculated by using Origin Pro 9G Software (Microcall software; OriginLab Corp, MA, USA).

Production of Chemically Modified mRNAs.

cmRNAs encoding eGFP, Tomato, MetLuc and human BMP-2 were produced using a published protocol (Kormann, loc. cit.). Molecular size and quality of the produced cmRNAs were analyzed by agarose gel electrophoresis (FIG. 1). All cmRNAs were of expected size and no degradation (lack of smearing) or additional by-products (extra bands of unexpected size) could be detected.

MTS Assay.

The cell monolayer was treated with 200 µl/well of MTS reagent solution (5:1 ratio in serum-free MEM without phenol red) and incubated for 3 h, light-protected under standard culture conditions. 100 µl medium from each well were transferred into a 96-well plate and the absorbance was determined at 490 nm in a PerkinElmer Wallac Victor 1420 multilabel counter (MA, USA). Latex rubber was used for induction of cell death (positive control) (Balmayor, 2013, loc. cit.). Untreated cells were used as a negative control (i.e. 100% cell viability).

CmRNA Formulations for In Vivo Testing.

C12-(2-3-2)/cmRNAs Lipoid Formulations.

A cationic lipid (referred to as "012-(2-3-2)") was prepared by mixing 100 mg N,N'-Bis(2-aminoethyl)-1,3-propanediamine (0.623 mmol) with 575.07 mg 1,2-Epoxydodecane (3.12 mmol, (N−1) eq. where N is 2× amount of primary amine plus 1× amount secondary amine per oligo (alkylene amine)) and mixed for 96 h at 80° C. under constant shaking. Lipid particles were formulated using cationic lipid C12-(2-3-2), helper lipids DOPE and cholesterol and PEG-lipid DMPE-PEG 2k at the molar ratios 8:5.29:4.41:0.88. Briefly, proper volumes of each lipid stock solution were combined in absolute ethanol to achieve concentrations of 50, 20, 20 and 20 mg/ml respectively. The final volume was adjusted to 200 µl. Liposome formation was achieved by rapid solvent exchange. Subsequently, 200 µl liposome mixture was mixed with 800 µl of cmRNAs (i.e. hBMP-2 cmRNA or FFL cmRNA) in a citrate buffer. Final cmRNAs concentration was fixed at 200 µg/ml with an N/P ratio of 17. After 30 min of incubation at RT lipoplexes were dialyzed against water overnight.

Fibrin Clots Containing C12-(2-3-2)/cmRNAs Lipoids for In Vivo Testing.

Fibrin clots containing the C12-(2-3-2)/cmRNA complexes were prepared immediate before implantation. Therefore, C12-(2-3-2)/hBMP-2 cmRNA and 012-(2-3-2)/FFL cmRNA complexes, both containing 2.5 µg cmRNA were mixed independently with 50 µl fibrinogen (3000 KIU/mL, Tissucol, Baxter, Unterschleißheim, Germany) and lyophilize. The fibrinogen-cmRNA powder was rehydrated with sterile water 30 min before starting the surgical procedure. After complete homogenization, the fibrinogen-C12-(2-3-2)/cmRNAs were mixed with 50 µl thrombin (4U/mL, Tissucol, Baxter, Unterschleißheim, Germany) and allowed to clot for 2 min. As a control, a fibrin clot was obtained following the same procedure mentioned above in the complete absence of cmRNAs.

Non-Critical Size Defect: hBMP-2 cmRNA Application—for In Vivo Testing.

A transcortical 3 mm non-critical size bone defect was created under sterile conditions. The bone defect was generated bilaterally in the middle of the femur diaphysis of 18 male Sprague-Dawley rats (Charles River Laboratories, Sulzfeld, Germany). The rats weighing between 650 and 750 g were randomised and divided into three groups (n=6 each): Fibrin (i.e. control group); Fibrin+2.5 µg FFL cmRNA and Fibrin+2.5 µg hBMP-2 cmRNA.

Anaesthesia was induced by intramuscular injection of a mixture of 110 mg/kg ketamine (Ketanest S, 25 mg/ml, Pfizer, Karlsruhe, Germany) and 12 mg/kg xylazin (Rompun, 20 mg/ml, Bayer, Leverkusen, Germany). A 3 mm drill hole was created in the middle of the femur shaft and irrigated with 0.9% sodium chloride solution (B-Braun, Melsungen, Germany). According to the groups, the defect was filled with 100 µl fibrin clot produced immediately before implantation. Thus, clots were transferred from the eppendorf tubes with a forceps and placed into the bone defect ensuring complete closure.

The rats received carprofen (rimadyl, Pfizer, Karlsruhe, Germany) (4 mg/kg) s.c. once a day for four days as an analgesic treatment.

Two weeks after the surgery the rats were sacrificed in general anesthesia by an overdose of pentobarbital (120 mg/kg, Eutha77, Essex Pharma, Hamburg, Germany) by intracardiac injection. The femora were harvested and stored in formalin solution (neutral buffered, 10%, Sigma-Aldrich, MO, USA) for 24 hours. Subsequently, the samples were transferred to 80% ethanol until further processing.

Micro Computer Tomography (µCT) Analysis—for In Vivo Testing.

All explanted femora were subjected to Micro Computer Tomography analysis (µCT) (µCT 40; Scanco Medical AG, Bassersdorf, Switzerland). The settings used for the measurements are described as follows. The increment was set on 157 µm with an angle of 0°. The voxel size of the images was set on 8000 µm with a total number of slices of 665. Hence, each sample was investigated in a total interval of 5.32 mm in the longitudinal direction. The integration time of the beam was set on the maximum of 300 ms and three data sets for each measuring point have been detected (the mean value of those is being used for the subsequent calculations). The µCT equipment was calibrated once a week with a hydroxyapatite phantom.

Mineralized bone and trabecular callus structures were analysed by a 3D segmentation algorithm using the software ImageJ (National Institutes of Health, MD, USA). The µCT data sets were transferred into a 3D layer set by a Plugin called KHK_microCT kindly provided by Prof. Karl Heinz Kunzelmann (Department of Operative/Restorative Dentistry, Ludwig-Maximilians-University of Munich, Germany). To separate the density levels of mineralized bone and callus, a grey-scale threshold was introduced and set between the values of 2500-4500 for the two density intervals that have been investigated. Another Plugin called BoneJ® was subsequently used for 3D imaging and quantification of the callus structure. The only numeric value that has been taken into account was the bone volume (BV) to compare the amounts of newly formed callus of each specimen. The amounts were automatically transferred into metric values by the KHK_microCT plugin, mentioned above. Detailed 3D images of the callus structure were obtained by the built-in plugin called "3D viewer".

Example 2. Optimization of the DF-Gold-to-mRNA Ratio for Transfection in AMSCs and BMSCs In order to further optimize the transfection protocol for AMSCs and BMSCs using mRNA lipoplexes with DF-Gold, different parameters were considered. DF-Gold-to-mRNA v/w ratio from 0.5 to 5 µl of the enhancer per µg nucleic acid at doses of 2.5, 5, 10 and 20 pg/cell were investigated. The results are shown in FIGS. 10 and 11. For both cells types, a dose of 20 µg mRNA/cell was found to be optimal. In addition, 5 µl DF-Gold/µg mRNA in AMSCs and 2 µl DF-Gold/µg mRNA in BMSCs was found as the best amount of enhancer to be used.

Example 3. Efficient cmRNA Delivery to the Stem Cells by Lipo- & Magnetofection

Firstly, the efficiency of different reagents to transfect adipose-derived stem cells (AMSCs) with cmRNAs was investigated. FIG. 2A shows the expression kinetics of Metridia luciferase for up to 120 hours after transfection. For all tested reagents, maximum expression was obtained 24 hours post-transfection. bPEI was the least efficient reagent among all and no significant expression was observed with bPEI for any of the measured time points ($p>0.05$). The different lipid based reagents differed in the resulting MetLuc expression kinetics. Whereas highest expression was observed with Lipofectamine2000 after 24 hours ($p<0.0001$), it was the most short lived with low MetLuc activity at 48 hours or later time points. On the other hand, DreamFect Gold (DF-Gold) and Dogtor, though somewhat less efficient at 24 hours time point compared to Lipofectamine2000, maintained MetLuc expression up to 120 hours. Besides transfection efficiency, cytotoxicity of different transfection reagents in AMSCs was also tested. MetLuc cmRNA complexes with Lipofectamine2000 were the most toxic with cell viability reduced to less than 75% within 5 hours (FIG. 2B). DF-Gold and bPEI complexes resulted in mild cytotoxicity with more than 80% cell viability at both the measured time points. No statistically significant difference was observed between cell viability for DF-Gold-transfected cells and untransfected control 24 hours post-transfection ($p=0.06$).

Based on desirable features of longer transgene expression (up to 120 hrs post transfection) and low cytoxicity, DF-Gold was selected to transfect mesenchymal stem cells (AMSCs and BMSCs) with cmRNAs. The dose of cmRNAs per cell was optimized for both cell types. The results revealed 20 pg/cell as the optimal dose for transfection. The data are presented in FIG. 10 and FIG. 11. The DF-Gold-to-cmRNA v/w ratio was fixed to be 4 (manufacturer's instructions) for a more accurate comparison between AMSCs and BMSCs. Nevertheless, this ratio was also refined for both cell types. The results indicated a v/w ratio of 5 for AMSCs and of 2 for BMSCs (FIG. 10 and FIG. 11).

Since plasmid DNA (pDNA) is the commonly used non-viral vector for gene transfer, MetLuc expression was compared after transfection with either MetLuc cmRNA or its plasmid counterpart (pVAXA120-MetLuc). Even though the target protein seems to be higher expressed 24 hours after pDNA lipofection of the cells, starting from 48 hours until the end of the observation time at 120 h, cmRNA expression remained high in this context as compared to pDNA that decreased dramatically. Without being bound by theory, the persistent expression could be an evidence for a better mRNA protection against degradation and an indication for the stabilization of the cmRNA, for example due to the respective lipoplexes used in accordance with the invention (e.g. DF-Gold™/cmRNA).

Efficacies of the target protein expression after lipofection of the pDNA and cmRNA, both coding for MetLuc, were compared (FIG. 2C). 24 hours post-transfection, transfection efficiency was almost twice higher for pDNA-transfected AMSCs (p=0.005). However, between 48 hours and 120 hours after transfection, levels of MetLuc expression was significantly higher for the cells transfected with the cmRNA (p=0.0002) and remained significantly higher up to 120 hours post-transfection (p=0.007). Areas under the "pDNA" and "cmRNA" curves, $AUC_{pDNA}=1.71 \cdot 10^8$ (Normalized RLU·h) and $AUC_{cmRDNA}=1.68 \cdot 10^8$ (Normalized RLU·h), calculated by integrating the data between zero and 120 h time points showed that cmRNA delivery can result in "bioavailability" of the target protein similar to that achieved after pDNA delivery.

To further increase the efficiency of cmRNA transfection, magnetofection was employed. For this purpose, PEI-decorated iron oxide core-silica shell magnetic nanoparticles (i.e. SO-Mag6-115) were used. The SO-Mag6-115 nanoparticles were characterized by approximately 96±14 nm in hydrodynamic diameter and a highly positive zeta potential of 34±3 mV. The magnetic nanoparticles appeared visually stable in aqueous suspension. No sedimentation was observed in water, 150 mM NaCl or cell culture medium. In addition, the nanoparticles presented a clear response to the externally applied magnetic field.

In magnetofection experiments, BMSCs were transfected in a side-by-side comparison to AMSCs. Magnetofection resulted in a significant increase in transfection efficiency for both cell types compared to the lipofection (FIG. 3). Flow cytometry analysis of eGFP-transfected cells at 24 hours post-transfection, revealed 59.7% (AMSCs) and 73.2% (BMSCs) positive cells (FIG. 3C). In contrast, only 37.5% (AMSCs) and 38.9% (BMSCs) cells resulted positive for eGFP when lipofection was performed (i.e. DF-Gold as transfection reagent). Representative histograms are shown in FIG. 12. This flow cytometry data was in, accordance with the data of fluorescence microscopy and MetLuc assay (FIGS. 3A, B and D). FIG. 3A clearly shows higher percent of transfected BMSCs expressing the tomato protein when magnetofection was used to transfer tomato cmRNA into the cells. Similar patterns were observed after delivery of the cmRNA coding for the eGFP, fluorescence microscopy pictures of AMSCs and BMSCs expressing eGFP are shown in FIG. 3B. Similarly, FIG. 3D shows a significantly higher expression of MetLuc at 24 hours post-transfection both by the AMSCs and BMSCs transfected via magnetofection with MetLuc cmRNA (p<0.0001).

A clearly more pronounced effect of magnetofection over BMSCs was obtained. The MAI for both cell types is given in FIG. 3D. 4.4-fold and 2.4-fold increases (MAIs) in MetLuc activity were determined for BMSCs and AMSCs, respectively. These data give an evidence of the significant enhancement of the protein expression in both MSCs types when magnetofection was used.

Example 4. Enhanced Secretion of hBMP-2 by Transfected Stem Cells

Transfections of hBMP-2 cmRNA were performed in Opti-MEM medium as well as in the presence of osteogenic medium due to the importance of osteogenic conditions in the forthcoming experiments. Interestingly, transfections performed in Opti-MEM with further medium change to osteogenic medium after 5 hours did not appear to jeopardize the transfection efficiency (FIG. 4A). Significantly lower hBMP-2 expression was observed when transfection was performed in the presence of osteogenic medium (p<0.05). FIG. 4B shows the content of secreted and cell associated hBMP-2 quantified in cell lysates and supernatants of transfected cells at different time points after transfection. Significantly higher hBMP-2 levels were detected in the samples from transfected cells compared to untransfected controls (p<0.001). Maximum hBMP-2 expression was observed 48 hours after transfection. Intracellular levels of hBMP-2 significantly decreased after 48 hours (p=0.007). Despite the high intracellular levels of hBMP-2, transfected AMSCs secreted significantly higher hBMP-2 levels up to 7 days post-transfection (FIGS. 4B and C) (p=0.0008). FIGS. 4B and C present the hBMP-2 levels in samples from magnetofected cells. The total cell-produced hBMP-2 was around 700 pg/µg cmRNA (FIG. 4C). This represents 6-fold increase (MAI) compared to hBMP-2 levels achieved after lipofection (FIG. 4C). The higher levels of hBMP-2 observed with magnetofection are consistent with higher transfection efficiencies and expression observed for cmRNAs coding for eGFP reporter (FIG. 3B, FIG. 12), MetLuc (FIG. 3D) and Tomato (FIG. 3A). Worth to mention is the fact that also the intracellular levels of hBMP-2 in transfected cells also increased considerably with magnetofection (p<0.0003). In FIG. 4B, it can be observed that the intracellular amount of hBMP-2 was almost the same as the secreted hBMP-2 at 24 hours post-transfection (p=0.8). After this time point, transfected cells were able to secrete significantly higher amounts of hBMP-2 compared to levels quantified in the cell lysate (p<0.001).

Example 5. hBMP-2 cmRNA Delivery Induced In Vitro Osteogenesis in AMSCs

As a first indication of in vitro osteogenesis, hBMP-2 transfected AMSCs were assessed for alkaline phosphatase (ALP) activity. 12 days after hBMP-2 cmRNA transfer, increased ALP expression could be confirmed in transfected cells (FIGS. 5A and B). Quantification of ALP activity demonstrated that significant increase was observed as early as 7 days and persisted until day 12 for transfected cells in comparison to control groups (FIG. 5B, p<0.01).

Subsequently, expression of osteogenesis related genes was quantified at different time points by real time PCR (FIG. 5C-H). For both lipofection and magnetofection groups, expression of RunX2, Osterix, ALP, Coll I, Ospeopontin and Osteocalcin increased over time compared to untransfected. Interestingly, RunX2, ALP and OPN showed significantly higher expression in the magnetofection group when compared with the lipofection at 14 days post-transfection. Especially in the case of OPN, magnetofection resulted in a continuous high expression after 14 days. On the other hand, the decrease on RunX2 expression was observed only after 14 days for the magnetofection group.

Alizarin red staining (FIGS. 6B and C) showed that the number of calcified nodules in the transfected groups was markedly higher than in untransfected cells (FIG. 6A). In addition, after lipofection, staining was clearly more intense at lower hBMP-2 cmRNA dose (i.e. 20 pg/cell, FIG. 6C). This corresponds to the optimized dose obtained by titration experiments with MetLuc cmRNA (FIG. 10). At higher dose of 32 pg/cell, mineralization was visibly poorer (FIG. C to the right). However, it became stronger when magnetofection was used for cmRNA transfer (FIG. 6B). Quantitative analysis of the alizarin red staining confirmed those results. FIG. 6D shows significantly higher mineralization for the lower dose group (20 pg/cell) in comparison with higher dose (32 pg/cell) when lipoplexes were used (p<0.0001). Mineralization increased with time of culture for the cells transfected with 20 μg hBMP-2 cmRNA. By using magnetofection for the higher dose group, significantly higher mineralization was detected (p=0.04 for 14 days and p=0.007 for 21 days, FIG. 6D). Moreover, it was clearly noticed as early as 14 days post-transfection.

Example 6. Transfection of Human Adipose Tissue Induced In Vitro Gene Expression Human adipose tissue was transfected with DF-Gold/tomato N1 cmRNA or DF-Gold/hBMP-2 cmRNA complexes. As shown in FIG. 7A, a large number of cells within the fat discs became tomato N1 positive after transfection. For hBMP-2 transfected discs, RT-PCR revealed over 4-fold increase in hBMP-2 expression for the transfected tissue in comparison to untreated explants (FIG. 7B). In addition, an increase in expression of bone related genes such as RunX2, Osterix and Coll I was clearly observed in transfected tissue cultured under osteogenic conditions compared to the controls. In the case of ALP and Coll I, their expression increased significantly from 3 days to 7 days post-transfection (p<0.001).

Example 7. BMP-2 cmRNA Approximately Doubles Bone Formation within Two Weeks In Vivo FIG. 13 A-C shows the μCT 3D reconstruction and longitudinal sections for all studied groups after 2 weeks of treatment. Indication of neo-bone formation can be observed in the μCT sections of the C12-(2-3-2)/hBMP-2 cmRNA group. In contrast, no indications of new bone formation were observed in the fibrin or C12-(2-3-2)/FFL cmRNA groups. This model was used to determine the influence of the hBMP-2 cmRNA in the spontaneous bone healing process. FIG. 13 D shows a quantitative analysis on the amount of callus formation for all groups. This μCT data showed significant increase in callus formation after 2 weeks in the animals treated with fibrin containing C12-(2-3-2)/hBMP-2 cmRNA (p<0.05) as compared to control groups. No significant difference was found between fibrin and fibrin containing C12-(2-3-2)/FFL cmRNA groups. In those groups, no significant callus formation was observed.

The obtained μCT results demonstrate the therapeutic effect of hBMP-2 cmRNA on bone healing. In those animals treated with hBMP-2 cmRNA a stimulation of in vivo osteogenesis was clearly observed. In contrast, for the animal treated with an unspecific cmRNA (i.e. FFL cmRNA) no osteogenesis was observed. This demonstrates that hBMP-2 cmRNA mediates the therapeutic expression of hBMP-2 at the site of the bone defect causing osteogenesis to occur.

Further Materials and Methods (Especially Pertaining to Examples 8 to 14).
Materials.

Dulbecco's Modified Eagle's Medium (DMEM), alpha Minimum essential medium (α-MEM), Dulbecco's Phosphate-Buffered Saline without Calcium and Magnesium (DPBS), Fetal Bovine Serum (FBS), Penicillin/Streptomycin (P/S), 0.05% Trypsine-EDTA and collagenase type I and II were purchased from Gibco by Life Technologies GmbH (Darmstadt, Germany).

Helper lipids including 1,2-dipalmitoyl-sn-glycero-3-phosphocholine (DPPC) and Cholesterol were supplied by Avanti Polar Lipids INC, (AL, USA). Other required materials for complex preparation, such as ethanol and 1,2-Dimyristoyl-sn-glycerol, methoxypolyethylene Glycol (DMG-PEG) 2 kD were purchased from CarlRoth (Karlsruhe, Germany) and Nof America Corporation (NY, USA), respectively. Collagen sponges with the trade name "KOLLAGEN Resorb™" were provided by Resorba (Nurenburg, Germany). Other reagents and materials were obtained from Sigma-Aldrich, unless specified otherwise.

Complex Preparation.

A cationic lipid, C12-(2-3-2) (provided by ethris GmbH and also known as "C12 EPE"), has been used as a non-viral transfection agent, along with DPPC and cholesterol as helper lipids and DMG-PEG2k as pegylated lipid.

RNA complexes were formed at RNA concentration of 200 μg/ml and N/P ratio of 8, which stand for molar ratios of amino group of lipid to phosphate group of RNA. Complexes were induced to self-assemble by rapid injection of ethanoic solution of lipid phase inside the aqueous phase containing cmRNA, using insulin syringes, followed by 15 sec vortex at high speed, and 30 min incubation at RT. The synthesized lipoplexes were dialyzed against double distilled water, using dialysis cassettes with molecular weight cut-off of 7 kDa (Pierce, USA), with a single water exchange after 30 minutes followed by dialysis overnight.

Measurement of Particle Size and Zeta Potential.

Particle size of lipoplexes were measured by laser light scattering, using a Zetasizer (Malvern Instruments, Worcester, UK). 750 μl of complexes were filled into a clean disposable cuvette cell and a total of 30 and 300 runs were performed for particle sizing and estimation of surface charge, respectively.

*Metridia* Luciferase Assay.

Kinetics of expression of a reporter mRNA, *Metridia* luciferase, was used to test the quality of collagen sponges for sustained mRNA delivery. For this, cell culture supernatant was collected every 24 h post transfection, and replaced with new media. The collected media was either proceeded immediately for measurement, or frozen in −20° C. until the last day of experiment to measure samples collectively. To quantify Met luc expression, 80 μl of supernatant was gently mixed, in black 96-well plates (Costar, NY, USA), with 30 μl of 0.05 mM Coelenterazine (Synchem, Felsberg, Germany) and measured, using a luminescence reader (Wallac Victor, Perkin-Elmer Life Sciences) in triplicates.

Isolation and Expansion of Rat Mesenchymal Stem Cells (MSCs).

Rat bone marrow mesenchymal stem cells (BMSCs) were provided by ethris GmbH. Adipose mesenchymal stem cells (AMSCs) were isolated form the fat tissue of a male rat. In this procedure, fat tissue was cut into millimeter sized pieces and transferred to a falcon tube (Corning Inc., NY, USA) containing sterile DPBS and washed several times with DPBS. Next, fat pieces were incubated in a collagenase type II solution (0.4 mg/ml) at humidified 37° C. for 30 min. Then, collagenase activity was stopped by adding complete DMEM culture medium (DMEM containing 10% v/v FBS and 1% v/v Penicillin/streptomycin), and the mixture was centrifuged at 600 g for 10 min. The upper fat layer was collected and re-suspended in complete DMEM culture medium. In the next step, the cell suspension was filtrated through a 40 μm cell strainer (Corning Inc., NY, USA), and plated in T75 cm flask (Corning Inc., NY, USA) and placed in humidified 37° C. and 5% CO2 in complete DMEM [20]. To remove the non-adherent cells the media was changed the following day. The cells were expanded with cell densities 1500-3000 cells/cm² and the media changed every three days. In this study, MSCs were used until passage 6.

Experimental Setup.

Collagen sponges were cut in small pieces (6 mm in diameter) using a puncher (VBS Lochzange, Nr. 19970181). The pieces were placed in the wells of a sterile flat bottom, polypropylene uncoated 96-well-plate (Eppendorf, Hamburg, Germany). 50 µl of lipoplexes in sucrose (2%), as a lyoprotective, were added drop wise to each piece and incubated for 90 min at RT to be completely soaked by the sponges. Loaded sponges then were moved to a high vacuum (Martin Christ Gefriertrocknungsanlagen GmbH, Osterode am Harz, Germany) and dried there for at least 2 h at 0.05 mbar. After that, sponges were either used for seeding cells or vacuum-sealed and kept at RT until use. In case of cell seeding, desired cell density in 50 µl complete media (complete DMEM for NIH3T3 and MSC cells) was added to every sponge followed by 30 min incubation at humidified 37° C. and 5% CO2. During incubation time, cells had to be seeded on collagen sponges as they could not adhere and grow on polypropylene uncoated plate. Then, 200 µl complete media were added to the wells and plates incubated in cell culture incubator.

Whole procedure performed under sterile condition using laminar hood (BDK Luft and reinraumtechnik GmbH, Sonnenbuhl-Genkingen, Germany). Moreover, plastic materials were avoided due to high electrostatic charge of collagen sponges.

Effectiveness of cmRNA Transfer.

FACS analysis was performed to characterize the effectiveness of cmRNA transfection in the 3D system. For this, each sponge was incubated with 300U/ml collagenase type I in Hanks' balanced salt solution (HBSS) with Calcium and Magnesium for 4 to 7 h. During incubation time, sponges were visually investigated for several times to ensure complete collagen digestion. Cells were centrifuged at 500 g for 5 min, followed by washing with DPBS. In the next step, cells were incubated for 5 min at 37° C. with 10 µl 0.05% Trypsin-EDTA to accelerate detachment of cells. Detachment was stopped by adding 90 µl of DPBS containing 2% FBS to each well.

FACS analysis was carried out using Attune NxT flow cytometer (Life technologies, NY, USA). Before each experiment, the machine was calibrated using calibration beads (Molecular probes, Life technologies, NY, USA). Cell debris was excluded from analysis by using forward- and side-scatter gating. Untransfected cells cultured under 2D and 3D condition were used as a negative controls to adjust fluorescence channel to detect eGFP fluorescence. The data, obtained from triplicates, was analyzed with FlowJo_V10 software.

Determination of Cell Death/Survival.

Cell viability was evaluated using propidium iodide staining, and WST assay. For both assays, vacuum-dried collagen sponges loaded with different doses of eGFP cmRNA complexes were used. 10,000 NIH3T3 cells per sponge were seeded in complete DMEM media and incubate at humidified 37° C. and 5% CO2 for 48 h.

For live-dead staining, cells were prepared for FACS analysis as described earlier. Then, 1:1000 dilution of 1 mg/ml stock of propidium iodide solution was added to each well exactly before measurement.

Cell survival was assessed also by WST reaction assay according to manufacture's instructions (colorimetric cell viability kit II (WST-1), Promokine, Heidelberg, Germany). Before adding the WST reagent, supernatant was pipetted up and down for three times to get a homogenized solution out of sponges in each well. Then 100 µl of supernatant was transferred to a new cell culture 96-well-plate (Corning Inc., NY, USA) for measurement. The supernatant from untransfected wells was used as blank. Absorbance was measured at 450 nm using a multiple spectrophotometric reader (Wallac Victor, Perkin-Elmer Life Sciences, MA, USA), in triplicates.

Secretion of hBMP-2 by MSCs Cultivated on hBMP2-cmRNA-Loaded Collagen Matrices.

Medium samples from MSC transfected with different doses of hBMP2 cmRNA lipoplexes were collected 24 h after transfection, and the concentration of hBMP-2 was measured with a human BMP-2 ELISA kit following manufacturer's instructions (R&D Systems, Minneapolis, MN). Experiments were performed in triplicates, and the protein content was determined using a standard curve ($r^2$=0.99).

Scanning Electron Microscopy.

Scanning electron microscopy (SEM) was used to characterize the morphology of collagen sponges and evaluate loading mRNA complexes on that. All samples were coated with Gold and Palladium with ratio of 60/40, using a sputter coater (Edwards sputter coater S150B, HHV Ltd, West Sussex, UK). Then, SEM was carried out using a Zeiss-Leo DSM 982 Gemini (FELMI-ZFE, Graz, Austria) at 1.2 kV.

Hematoxylin Staining of Cells Seeded on the Collagen Sponges.

24 h after seeded NIH3T3 cells on collagen sponges, cells were fixed with 4% formaldehyde in phosphate-buffered saline (PBS), PH 7.4, overnight at RT. Then collagen sponge were dehydrated and embedded in paraffin. Collagens' sections (7 µmm) were deparaffinized, and stained with Hematoxylin according to standard protocols.

RNA Isolation, and Reverse Transcriptase Real-Time Polymerase Chain Reaction (RT-PCR).

7 and 14 days after seeding cells on the hBMP-2 loaded collagen sponges, appropriate volume of collagenase I in Hanks' balanced salt solution (HBSS) was added to each well to reach the final concentration of 300 U/ml of collagenase type I. Then, plates were incubated for 4 to 7 hours at humidified 37° C. and 5% CO2. When the collagen sponges were entirely dissolved, cells were centrifuged at 500 g for 5 min, supernatant removed and cells subsequently lysed by TRIzol reagent (Ambion by life technologies, Darmstadt, Germany) for total RNA isolation, following manufacture's instruction.

RNA concentration and purity were determined with NanoDrop 2000C spectrophotometer (Thermo Scientific, DE, USA). First-strand cDNA was reverse-transcribed from 450 ng of total RNA by the use of First Strand cDNA Synthesis Kit (Thermo Scientific, Darmstadt, Germany), following manufacturer's instructions. For each of the hBMP2 transfected and untransfected groups, 15 sponges were used, and the lysed cells were pooled together for RNA isolation.

To evaluate the expression of osteo-related genes, soAdvanced Universal SYBR Green Supermix (Bio-Rad, Munich Germany) was used to perform quantitative realtime PCR (n=3). PCR was carried out on a Light Cycler 96 thermal cycler (Roche, Mannheim, Germany). The expression levels of target genes were normalized to that of GAPDH (in case of MC3T3-E1 cells), and beta-tubulin (for MSCs). The data are expressed as fold induction relative to controls, i.e. untransfected MC3T3-E1cells in 3D, and untransfected MSCs in 2D culture. Primer sequences were listed from 5' to 3' as follows:

Mouse Primers for Bone Regeneration Experiment on MC3T3-E1 Cells:

| Gene | Forward primer (SEQ ID No.) | Reverse primer (SEQ ID No.) |
| --- | --- | --- |
| ALP | gtgccctgactgaggctgtc (32) | ggatcatcgtgtcctgctcac (33) |
| OCN | ccgggagcagtgtgagctta (34) | tagatgcgtttgtaggcggtc (35) |
| GAPDH | gcacagtcaaggccgagaat (36) | gccttctccatggtggtgaa (37) |

Rat primers for bone regeneration experiment on MSCs:

| Gene | Forward primer (SEQ ID No.) | Reverse primer (SEQ ID No.) |
| --- | --- | --- |
| RUNX2 | ccgtgtcagcaaaacttctttt (38) | gctcacgtcgctcatcttg (39) |
| OSX | cccaactgtcaggagctagag (40) | gatgtggcggctgtgaat (41) |
| OCN | acggcagcttcagctttg (42) | gaggcagagagagggaacag (43) |
| ALP | tggaacactgggtcccata (44) | gacctggtcttccctccaa (45) |
| β-tubulin | ctgatgagcagggcgagt (46) | tccgagaagttcttaagcctca (47) |

In Vitro Bone Differentiation.

Collagen sponges were loaded with 3 µg hBMP2 mRNA lipoplexes in 2% sucrose and vacuum-dried as described previously. In the next step, 30,000 freshly isolated rat AMSCs, in 50 µl DMEM, were seeded on each collagen sponge and incubated for 30 min at 37° C. in a humidified atmosphere of 5% CO2, to ensure the cell adherence to the collagen sponges. Then, 250 µl Osteogenic Medium (DMEM+2% FBS+10 mM ß-Glycerophosphate+200 µM L-Ascorbic acid+1% Pen-Strp) was added to each well. Half of the media was renewed every two to three days. Negative controls including untransfected cells in 3D (seeded on collagen sponges) and 2D (seeded on the normal cell culture flask) were treated exactly like transfected cells in 3D. 7 and 14 days post seeding, cells were investigated for expression of osteogenic markers by RT-PCR.

In Vivo Bone Differentiation.

An in vivo implantation experiment was design, following the Guidelines for the Care and Use of Laboratory Animals (National Research Council (US) Committee, National Academies Press (US), 2011). In total 9 Sprague-Dawley rats (6-month-old males, average weight 600 to 700 g; Janvier, Le Genest-St-Isles, France) were used. In each rat, femur defect in the left leg was treated with empty collagen sponge (as negative control), and the right femur defect was cured with 2.5 µg hBMP2 cmRNA-loaded sponge. To avoid infection and alleviate pain during and after the operation, routine antibiotics and analgesics were prescribed, and animals were anesthetized using a combination of Medetomidin (Domitor®, Orion pharma, Espoo, Finland; 135 µg/kg), Midazolam (Dormicum®, Unterhaching, Germany; 2.5 mg/kg) and Fentanyl (Duragesic®, Beerse, Belgium; 5 µg/kg).

After shaving and disinfecting, small skin incisions were made in lateral external area. A full-thickness bone defect was created in the central part of the femur bone using a bone drill with a 2-mm outer diameter.

After applying the scaffolds into the defects, a polyvinyl membrane was used to cover the implant area to minimize the effect of any pericranium self-renewal capacity. Finally, 4-0 vicryl sutures were used to close the pericranium and the overlying skin. The rats were scarified at 2 weeks, using natrium pentobarbital (Narcoren®, Merial GmbH, Hallbergmoos, Germany; 400 mg/kg), and samples were collected for µCT and histologic analysis.

µ-Computed Tomography (µ-CT) Analysis.

Three dimensional x-ray micro-computed tomography (µ-CT) imaging was performed to quantify bone formation, using µCT 40 (Scanco Medical, Bassersdorf, Switzerland). Bone volume was measure to compare the amounts of newly formed callus of each specimen (defects treated with empty collagen sponges and defects treated with hBMP2 cmRNA-loaded collagen sponges).

Histological Observation of Rat Femur Defects.

Qualitative and morphological aspects of bone regeneration have been analyzed by means of histological preparation. Femurs were dehydrated in a grades series of ethanol from 40% to 100% and embedded in metacrylate resin (Technovit 7200, Heraeus Kulzer GmbH, Wehrheim, Germany). Thin ground sections (ca. 30 µm) were prepared and stained with Levai Laczko staining and evaluated under a light microscope [Donath K. and Breuner G., J. Oral Pathology (II), 1982, 318-326; Laczko J. and Levai G. (31), Mikroskopie, 1975, 1-4].

Statistical Analysis.

All statistical analyses were performed using GraphPad Prism version 6.05 for windows (GraphPad Software Inc., San Diego, CA). Statistical significance was determined using t-test and multiple t-test. $P<0.05$ was considered significant.

Example 8. Further, Alternative, cmRNA Complex Formation with C12-(2-3-2)

A cationic lipid, provided by Ethris GmbH, has been used as a non-viral vector, to make a stable lipoplex with cmRNA, based on electrostatic interaction between the positive amino groups of lipid and negative phosphate groups of cmRNA (Anderson, Human amino groups of lipid and negative phosphate groups of cmRNA (Anderson, Human Gene Therapy 14, 2003, 191-202). To stabilized the lipoplex structure and reduce the leakage, Ethris lipid was supplied with two helper lipids entitled 1,2-dipalmitoyl-sn-glycero-3-phosphocholine (DPPC) and Cholesterol (Anderson, Drug Delivery 11, 2004, 33-39; Liang, Journal of Colliod and Interface Science 278, 2004, 53-62). At the end, 1,2-Dimyristoyl-sn-glycerol, methoxypolyethylene Glycol (DMG-PEG) 2 kD was added to the lipid mix to provide a PEGylated liposome. It is already well known that PEGylation improves the physico-chemical characteristic of liposome formulation by increasing water solubility, protecting from enzymatic degradation, and limiting immunogenic and antigenic reactions (Milla, Current Drug Metabolism 13, 2012, 105-119). Final N/P ratios for entire ethanoic lipid mixture were 8/50.29/4.41/0.88 standing for molar ratios of amino group of C12-(2-3-2)/DPPC/Cholesterol/DMG-PEG, respectively, to one phosphate group of cmRNA molecule. Biophysical characteristics of the cmRNA lipoplexes has been tabulated in Table 6. Hydrodynamic diameter for all the products are roughly around 50 nm with poly dispersity index close to 0.1, which indicate a homogeneous product. Besides, total surface charges for all complexes were slightly positive, close to neutral.

Example 9. cmRNA Complexes Loading and Cell Seeding on Collagen Sponges

Prior to loading on the collagen sponges, 2% sucrose was added to the cmRNA lipoplex solutions a lyoprotectant. Lyoprotectants maintain the integrity of the biological system during dehydration in vacuum-drying process (Kannan, Journal of Liposome Research, 2014, 1-9). Visualizing sponges by scanning electron microscopy (SEM) showed that a vacuum-dried collagen sponge, containing 2% sucrose, resembled a closed cage with smaller pores, compared to that before vacuum-drying (FIG. 23.).

To ensure the possibility of loading cmRNA lipoplexes on the sponges, cmRNA-loaded sponges were investigated by SEM, and lipoplexes containing cmRNA were detected on the collagen sponges (FIG. 14.A).

To investigate cmRNA loading as well as cell transfection on the collagen sponges, sponges were loaded with 2 µg of tdTomato cmRNA lipoplexes, where 10% of tdTomato cmRNAs were covalently FITC-conjugated. The dispersity of cells and cmRNA lipoplexes on the sponges as well as transfection efficacy were visualized, using Leica DMi8 fluorescent microscope (Leica microsystems, Heerbrugg, Switzerland) 30 h after seeding NIH3T3 cells. As shown in FIG. 14.B, cells were transfected and expressed tdTomato protein (red spots), mostly in locations with the high cmRNA accumulation (green spots).

For investigation of cell behavior on the 3D matrix, immigration of NIH3T3 cells into the collagen sponges was confirmed by hematoxylin staining of a vertical cut of a sponge, seven days after seeding NIH3T3 cells. From FIG. 1C, it becomes evident that cells are able to immigrate into the sponge and use the entire matrix for growing and signaling, which more likely resembles an in vivo-like situation.

Firstly, it was shown that cells can grow within the collagen sponges 3D matrices. Other studies also proved collagen sponges as a suitable 3D scaffold for cell culturing, which can in turn improve cell signaling and cellular behavior, and have influence on gene expression in the cells (Chevallay, Medical and Biological Engineering and Computing 38, 2000, 211-218). Then, a uniform distribution of cmRNA lipoplexes and cells were visible using SEM and fluorescent microscopy with fluorescent-labeled cmRNAs (FIG. 14.).

Example 10. Transfection Efficacy and Cell Viability on Collagen Sponges

Figure 15A:
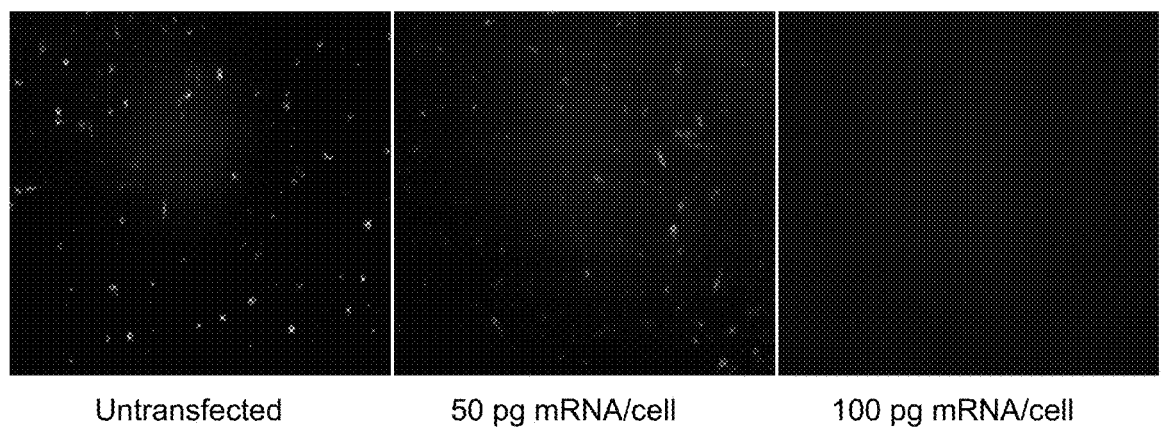
Figure 15B:
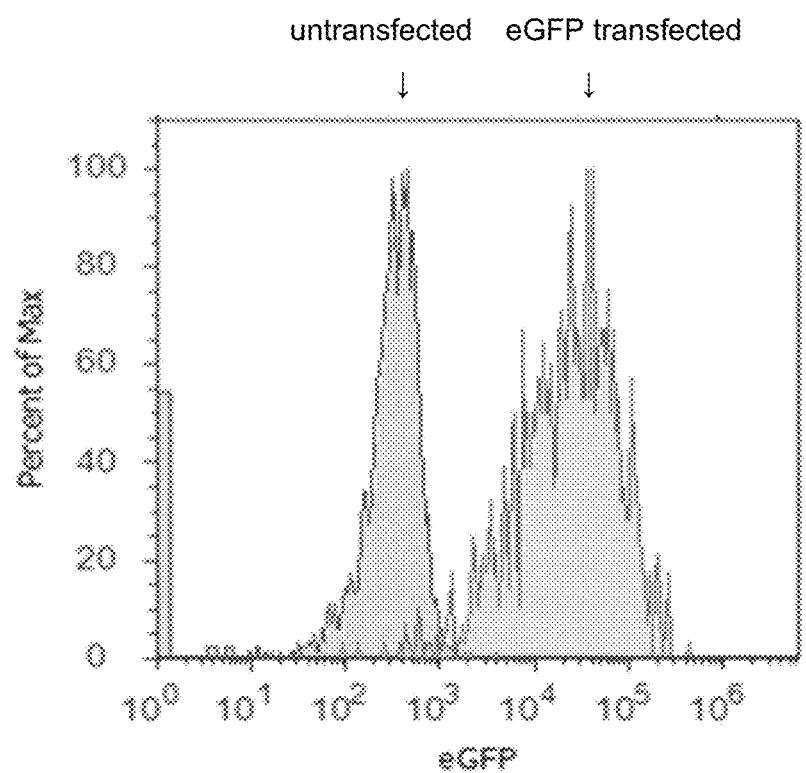
Figure 15C:
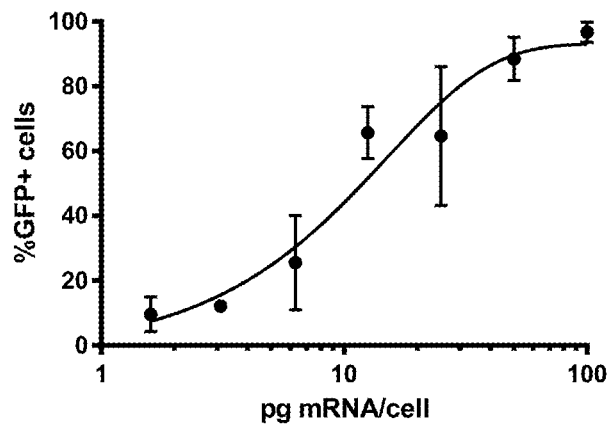

To verify the efficacy and safety of cell transfection on collagen sponges, expression of eGFP cmRNA, in NIH3T3 cell line was assessed at 48 h after transfection. Firstly, positive eGFP expressing cells were visualized using JULY™ fluorescence microscope (Baker and Baker Ruskinn, USA) (FIG. 15A). To quantify these results, FACS analysis was performed and a significant increase in the mean fluorescence intensity in transfected cells was observed. (FIG. 15B). In dose-response experiments, up to 100% transfection efficiencies were observed with using higher cmRNA amounts per cell (FIG. 15C).

Figure 15D:
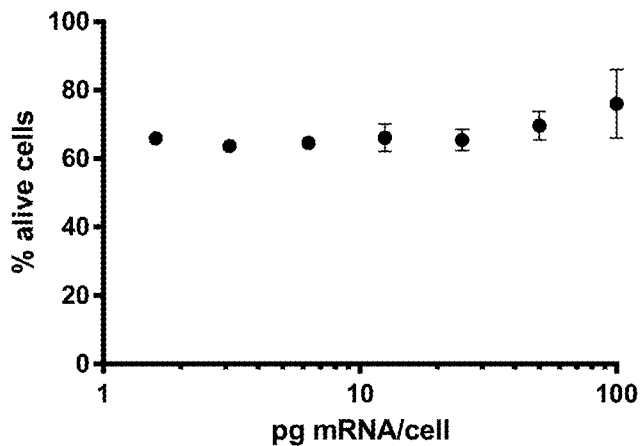
Figure 15E:
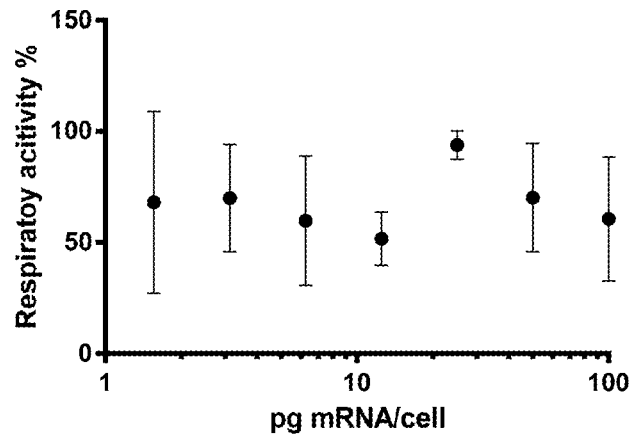

In clinical settings, not only transfection efficiency but also cellular toxicity becomes a deciding factor. Consequently, in addition to GFP expression, cell viability was also quantified at 48 h post transfection, in two independent experiments, using two different methods, namely PI staining followed by FACS analysis, and WST assay. Comparable results with cell viabilities in the range of 60-70% were obtained with both methods (FIGS. 15D and E). Unlike transfection efficiency, where a dose dependent increase in efficacy was observed, cell viability appeared to be dose independent.

Quantification of eGFP cmRNA transfection efficacy on the collagen sponges by FACS analysis proved a remarkable high efficacy of our technology, which reaches to 100% transfected cells (FIGS. 15B and C).To validate our technology for clinical approaches, cell viability was also assessed, and a dose-independent cell viability around 60-70% was observed, which was acceptable for our both in vitro and in vivo approaches. (FIGS. 15D and E). The dose independency in cell-viability assays could be the results of the uniform cell distribution within the 3D matrix, which can closely resemble an in vivo situation, and improve cell signaling and proliferation (Mueller-Klieser, American Journal of Physiology-Cell Physiology 273, 1997, C1109-C1123), in the way that cells can tolerate even high doses of cmRNA complexes. This dose-independent trend in cell viability will be particularly beneficial when the general efficacy is low and higher doses of cmRNAs are needed.

Example 11. Collagen Sponges Function as Depots for Sustained cmRNA Delivery

To investigate whether collagen sponges can provide a sustained cmRNA delivery system, expression kinetics of Metridia luciferase (Met luc) cmRNAs in NIH3T3 cells were measured every 24 h, and compared in 2D and 3D culture (FIG. 16).

Based on the results, collagen sponges showed the properties of a sustained cmRNA delivery system with a plateau of protein expression for six following days. In addition, in contrast of 2D cell culture that showed almost no expression after 8 days, cmRNA-loaded collagen sponges showed a relative high protein expression even after 11 days, with higher cmRNA doses.

Similar results have been obtained by loading unmodified mRNA-containing lipoplexes on the collagen sponges (FIG. 24). However, the system lost its retard delivery efficiency when non vacuum-dried collagen sponges were used (FIG. 25). This provides the evidences that vacuum-drying is an essential and critical step to provide a sustained cmRNA delivery system in our setting.

Figure 17:
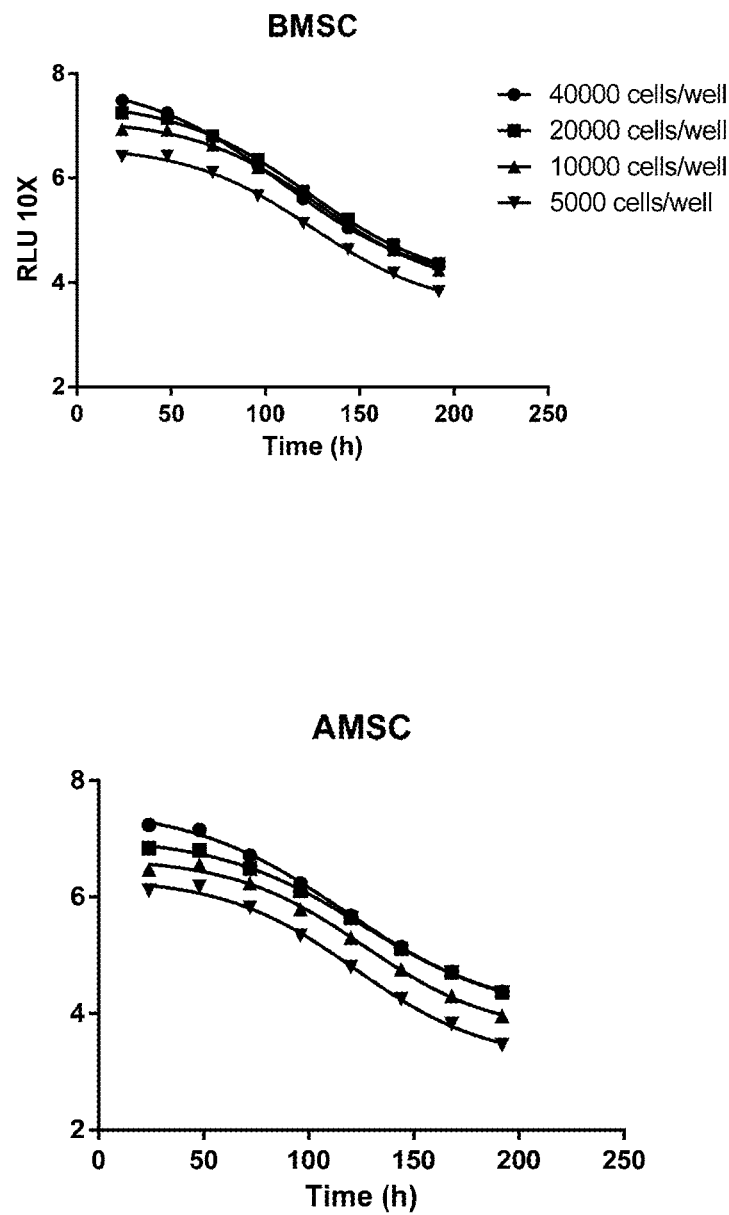

In the next step, the system was tested for primary cells using rat mesenchymal stem cells (MSCs) isolated from bone marrow (BMSCs) and adipose tissue (AMSCs). Using both cell types, kinetics of Met luc expression was determined by seeding increasing number of cells on lipoplex-loaded collagen sponges. As shown in FIG. 17, regardless of cell density, MSCs seeded on the complex-loaded collagen sponges, revealed a prolonged protein expression for at least four following days. Since no significant increase in Met luc expression was observed for higher cell densities (>10000 cell/sponge), further experiments were performed using between 10-20,000 cells/sponge.

Kinetics of expression of *Metridia* luciferase cmRNA were measured to assess the ability of collagen sponges for sustained cmRNA delivery, using cell line (FIG. 16) and primary cells with various cell densities (FIG. 17), and also modified and unmodified mRNAs (FIG. 24). Based on the kinetics results, vacuum-dried cmRNA-loaded collagen sponges provide a robust sustained delivery system for cmRNAs, which is independent form RNA modifications, cell type and cell density; even for primary cells which are more sensitive to the contact inhibition and cell density [21]. Such a system will be very advantageous in case of lack of the source of cells and patient samples, when a switch to a low cell density is also feasible. To have such a retard delivery system, vacuum-drying seems to have a critical role, whereas expression of cmRNAs in non-dried sponges drop more promptly (FIG. 25). The prolonged cmRNA delivery after vacuum-drying could without being bound by therapy be due to the closed-cage structure of vacuum-dried collagen sponges (FIG. 23), where imprisoned lipoplexes need time to either get in contact with cells or release from the matrix [10]. The uniform distribution of the vacuum-dried cmRNA lipoplexes on the collagen sponges (FIG. 14A.) can be another reason for the steady state expression for several days, without peaks of transfection efficacy or burst release (Lee, Biomaterials 32, 2011, 744-752).

Vacuum-drying had another substantial influence too, where cmRNA complexes on the vacuum-dried collagen sponges were stable at least for 6 months at RT (FIG. 22; see also example 14). This considerable shelf life for the very sensitive mRNA molecule has been achieved for the first time in this study. This can in turn increase the availability and ease of use of the potential cmRNA therapeutics, and bring cmRNAs closer to the clinical applications.

When our technology was well optimized for delivery of reporter cmRNAs in to cell line as well as primary cells, our system was tested to investigate a physiological effect, namely bone formation, using hBMP2 cmRNA.

Example 12. In Vitro Cell Differentiation

To validate the performance of the sustained cmRNA delivery system for a physiological effect, two in vitro bone differentiation experiments were designed with two different cells, namely MC3T3-E1 and MSCs, using hBMP2 cmRNA lipoplexes (Lee, Biomaterials 32, 2011, 744-752; Meine, Biomaterials 27, 2006, 4993-5002; Kim, Biomaterials 28, 2007, 1830-1837).

To confirm bone differentiation in osteoblast like cells (MC3T3-E1), 7 and 14 days after seeding the cells on hBMP2 cmRNA-loaded collagen sponges, reverse transcription polymerase chain reaction (RT-qPCR) was performed to quantify the expression of osteogenic markers (OCN, and ALP). Untransfected cells, seeded on unloaded collagen sponges, were used as negative control. As shown in FIG. 20.A, both markers strongly expressed in both time points, and the expressions increased by day 14.

In the next step, the same setting was used to perform in vitro bone differentiation using MSCs. Firstly, freshly isolated MSCs were evaluated for the positive and negative markers, using FACS analysis (FIG. 26). Then, MSCs were seeded on the collagen sponges loaded with hBMP2 cmRNA lipoplexes. At 24 h post transfection, hBMP2 expression was quantified in the supernatant, using ELISA (FIG. 19). 7 and 14 days later, expression of osteogenic markers (RUNX2, OSX, OCN, and ALP) were detected, using RT-qPCR. Unexpectedly, all markers were highly expressed, not only in transfected but also in untransfected MSCs seeded on the 3D collagen scaffold. Therefore, an untransfected MSCs culture in a conventional 2D setting (standard cell culture cultivation in a petri-dish), treated exactly like cells in 3D (with respect to medium and washes), was chosen as the negative control to normalize the expression of differentiation markers observed in cells in 3D. As presented in FIG. 20B, cultivation in a 3D collagen matrix alone significantly upregulates the expression of osteogenic markers in MSCs.

Figure 20A:
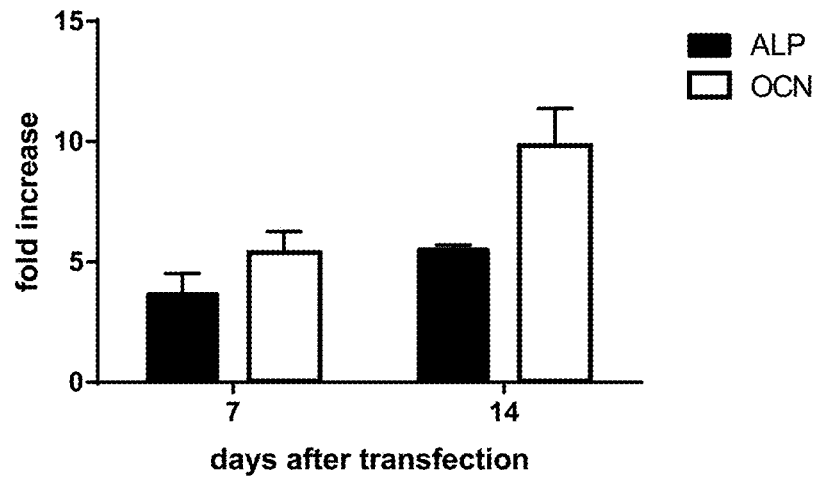

In vitro bone differentiation was performed using osteoblast like cell line (MC3T3-E1) and MSCs, seeded on the hBMP2 cmRNA-loaded collagen sponges [10, 19] (FIG. 20). In case of MC3T3-E1 cells, hBMP2 mRNA had a significant effect in triggering bone formation, as expressions of osteogenic markers were several fold higher in transfected cells compared to untransfected cells seeded on 3D collagen scaffolds (FIG. 20A).

Figure 20B:
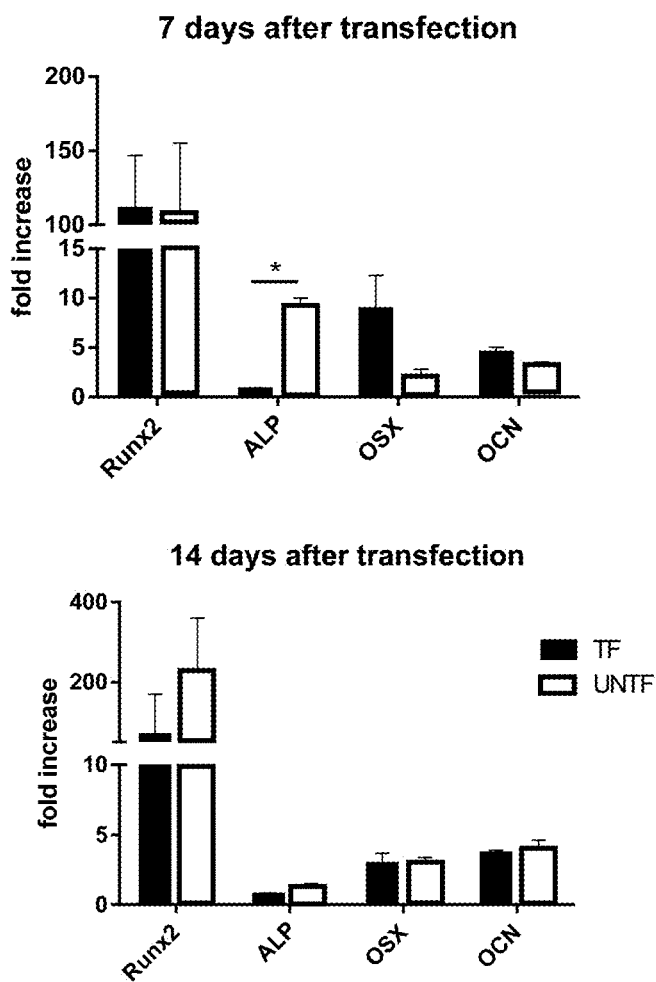

On the contrary, there was almost no significant difference in expression of osteogenic markers between hBMP2 transfected and untransfected MSCs on the collagen sponges (FIG. 20B). However, expression of hBMP2 from MSCs seeded on the hBMP2 cmRNA-loaded collagen sponge was previously detected, using ELISA (FIG. 19). According to this data, collagen sponges themselves can trigger bone regeneration in MSCs in vitro. Previously, it also has been shown that collagen sponges can initiate Chondrogenesis (Bosnakovski, Biotechnology and Bioengineering 93, 2006, 1152-1163). Another explanation for this phenomenon goes through the dramatic macroscopic changes in transfected and untransfected collagen sponges containing MSCs (FIG. 27). By day 7, sponges loaded with hBMP2 appeared more fluffy and expanded in size, while unloaded sponges condensed and shrunk over time. Since MSCs were too confluent in the unloaded shrunk sponges, they would lose their multipotency and start to reprogram to the terminally differentiated cells (Sekiya, Stem Cells 20, 2002, 530-541; Coulter, PNAS 97, 2000, 3213-3218), and as they were growing in the osteogenic medium, an osteogenic differentiation would be most probable.

Example 13. In Vivo Cell Differentiation

Figure 21B:
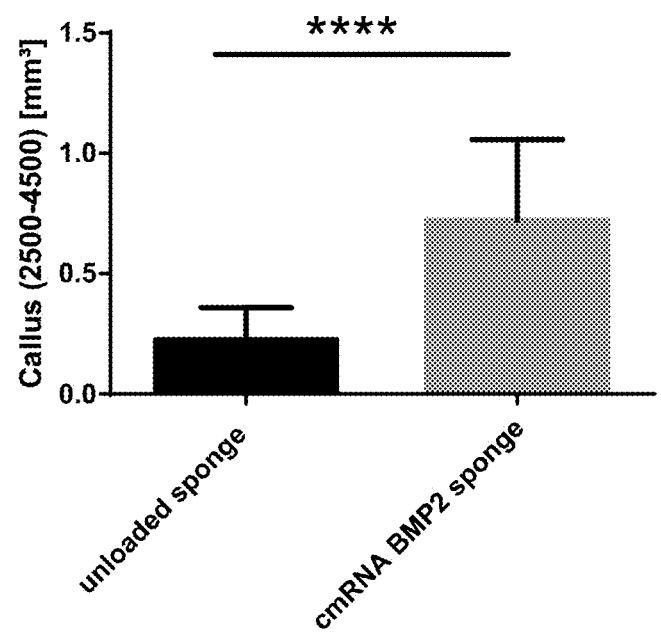

In vivo bone regeneration activity was evaluated by a rat femur defect model. hBMP2 cmRNA-loaded and unloaded vacuum-dried collagen sponges were applied to femur defects of two groups of animals, as the experimental and control group, respectively. In details, the prepared sponges were implanted in to 2-mm diameter bone defects, created in the central part of rat femur bones. To visualize and quantify bone healing, a micro-computed tomography (μ-CT) scan was taken two weeks after surgery. As presented in FIG. 21A, more newly formed bone was found in the hBMP2 cmRNA treated group. Quantification of the results also proved that hBMP2 cmRNA-loaded collagen sponges could significantly increase bone regeneration compare to empty collagens (FIG. 21B). The effect of hBMP2 on callus formation is also well visible in the 3D scanning model of μ-CT (FIG. 29). Going into more details, further analysis with p-CT in different parts of the bone (periosteal, cortical, and medulla) revealed the highest bone regeneration in the medullary area (FIG. 27), where lots of bone marrow stem cells do exist.

Figure 18A:
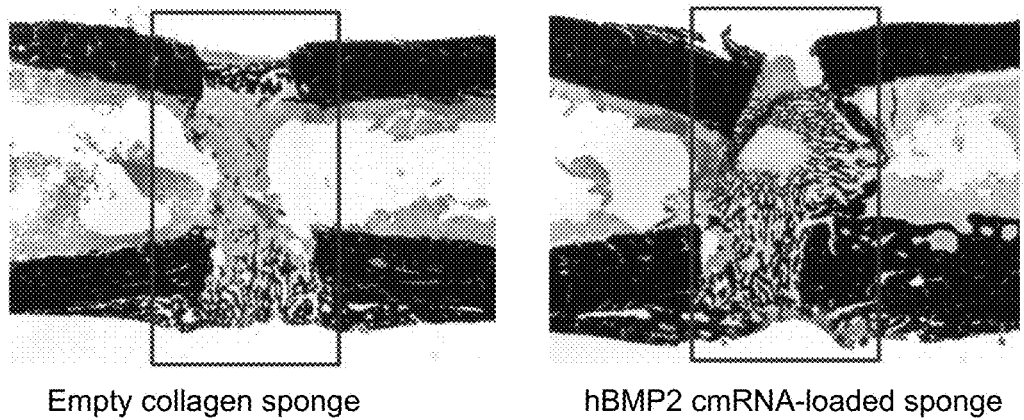
Figure 18B:
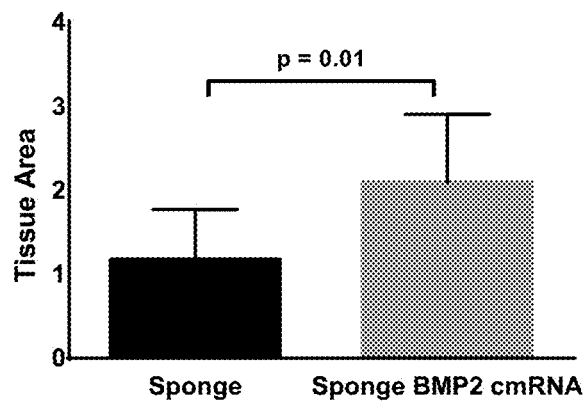

To validate newly formed bone, Immunohistochemistry also was carried out at week 2, and higher mineralized bone tissues were found in the hBMP2 cmRNA treated group. Similar to μ-CT results, highly mineralized areas (dark black in the immunohistochemistry images) were observed mostly in the medullary parts of bones (FIG. 18.A). Moreover, histological analysis in the periosteal area showed a significant increase in callus formation in hBMP2 cmRNA treated group compared to control (FIG. 18.B). Further analysis, proved that significantly more fibrous tissues were created in the group treated with hBMP2 cmRNA-loaded sponges, compared to group treated with empty sponges (FIG. 18.C). In bone healing process, fibrous tissues can trigger a trend toward osteoid formation, and bone regeneration (Luellmann-Rauch, De BoeckSupèrrieur, 2008). Accordingly, FIG. 18D present more osteoid formation in hBMP2 cmRNA treated group.

To test our cmRNA delivery system in the preclinical level, cmRNA-loaded collagen sponges have been applied for in vivo bone formation, using hBMP2 cmRNA. In vivo bone formation effect of chemically modified BMP2 cmRNA complexes with PEI has recently been published (Elangovan loc. cit.).

In this study, however, hBMP2 cmRNA lipoplexes with half size of PEI complexes were used (Table 6), which can improve in vitro cellular uptake as well as in vivo pharmacokinetics and biodistribution (Lee, Biomaterials 32, 2011, 744-752; Albanese, Annual Review of Biomedical Engineering 14, 2012, 1-16). Then the hBMP2 cmRNA lipoplexes were stabilized on collagen sponges by vacuum drying and formed ready-to-use bioproducts. At the end, the efficacy of our bioproducts was evaluated with an animal model, to prove the functionality of our technology in hBMP2 cmRNA delivery for in vivo bone regeneration.

Various studies proved the effect of BMP2 protein in bone tissue engineering, using different carriers (Meinel, Biomaterials 27, 2006, 4993-5002; Kempen, Biomaterials 30, 2009, 2816-2825). However, currently collagen is the only FDA approved carrier for recombinant hBMP2. Consequently, the efficiency of collagen, as a carrier for stabilized hBMP2 cmRNAs, was investigated in this study.

To perform the in vivo experiment, loaded and unloaded collagen sponges implanted into the rat femur defects. Two weeks later, rats were sacrificed and bone formation was evaluated, using μ-CT and immunohistochemistry. The obtained results were similar to that of in vitro bone regeneration in MC3T3-E1 cells. Both μ-CT results and Immunohistochemistry showed significantly higher bone formation in the defects treated with hBMP2 cmRNA loaded collagens, compared to empty collagens (FIGS. 21, 18A and B, and FIG. 29). Further analysis in different parts of bone (periosteal, cortical and medulla) proved that the maximum bone formation took place in the medullary area (FIG. 28, FIG. 21 A, and FIG. 18 A). Although, for an ideal tissue engineering, new bones should be created mostly in the cortical area, such a medullary bone formation here is due to placement of collagen sponges in the bone defects. In our study, loaded and unloaded collagen sponges were placed in the whole bone defect (and not just in the cortical part). Since medullary area contains much more BMSCs compare to other parts of bone, maximum bone formation happened there. In other words, to see a cortical bone formation, hBMP2 cmRNA-loaded collagen sponges should be placed just in the cortical area, which is not feasible in a rat models, due to small size of rats' bones. Other publications, treating the same animal model with recombinant BMP2 protein, also showed more bone formation in medulla compared to cortical, at 2 weeks. However, more cortical bone formation was observed in 4 weeks (Keibl, Injury 42, 2011, 814-820). Therefore, additional experiments in later time points could be useful for investigation of bone regeneration in cortical area.

Figure 18C:
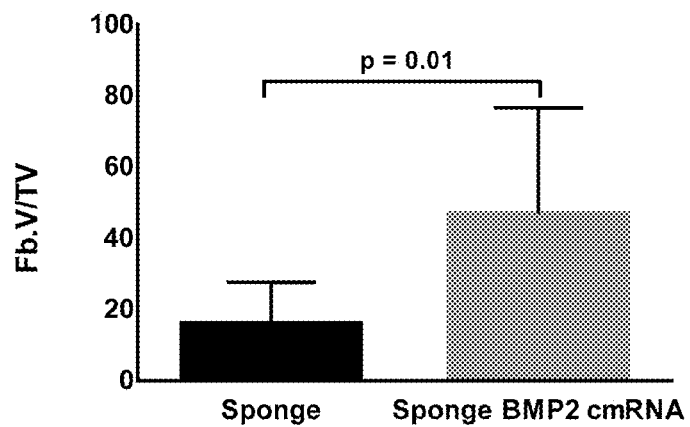
Figure 18D:
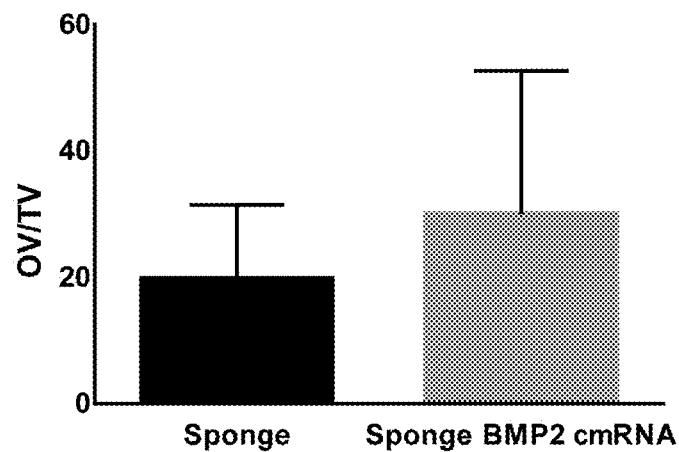

Further histological analysis proved that significantly more fibrous tissues were created in the hBMP2 treated group (FIG. 18C). This can also be considered as a sign of bone tissue formation, as in bone healing process, fibrous tissues can follow a trend to functional fibrous tissue and then toward osteoid formation (Luellmann-Rauch, De Boeck Supèrrieur, 2008). Likewise, more osteoid formation was detected in the hBMP2 cmRNA treated group (FIG. 18D).

These results were different from what have been seen in the in vitro bone regeneration using MSCs, where hBMP2 cmRNA-loaded and unloaded collagen sponges worked almost the same for bone formation (FIG. 20B). This difference could be due to differences in the in vitro and in vivo circumstance, as a great deal of factors could influence on the effect of BMPs and collagen sponges for bone regeneration in vivo, such as presence of small molecules, growth factors and cytokines (Lynch, Journal of Periodontology 62, 1991, 710-716; Wan, PNASA 105, 2008, 868-691; Mountziaris, Tissue Engineering Part B: Reviews 14, 2008, 179-186).Such factors are missing in the in vitro situation, and thus in vivo results may not exactly follow in vitro ones. Accordingly, collagen sponges, and other carriers described herein, may be pre-loaded not only with desired cmRNA lipoplexes, but also with small molecules and cytokines, which can enhance the immigration of MSCs inside the sponges (Xu, Oncology Reports 23, 2010, 1561-1567; Wu, Stem Cell Reviews and Reports 8, 2012, 243-250), and thus improve the transfection efficacy.

Further Results of Bone Histomorphometry:

After necropsy femur bones were harvested, freed from surrounding soft tissue and subsequently fixed in 4% paraformaldehyde (PFA) for 24 hours. Next, samples were dehydrated in by immersing in graded alcohols and xylene and finally embedded in methylmethacrylate (MMA). Subsequently micromilled cross-sections were prepared and stains according to the protocol of Von Kossa, Toluidine Blue and Tartrate Resistant Acid Phosphatase (TRAcP) were prepared.

The drill hole area was divided in four theoretically areas for histomorphometry. Namely:
- the periostal area surrounding the drill hole (M1),
- the area of the visible drill hole within the compacta in which the implant was placed (M2),
- the area of the drill hole within the bone marrow in which part of the implant was as well placed (M3)
- and a defined area surrounding the drill hole area within in the bone marrow in which the implant was placed (M4).

Figure 30A:
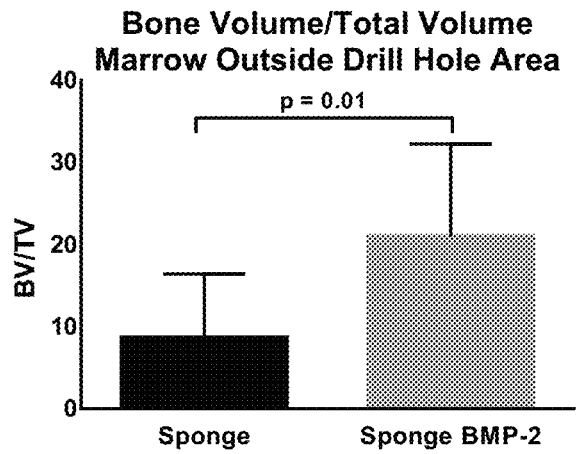
Figure 30B:
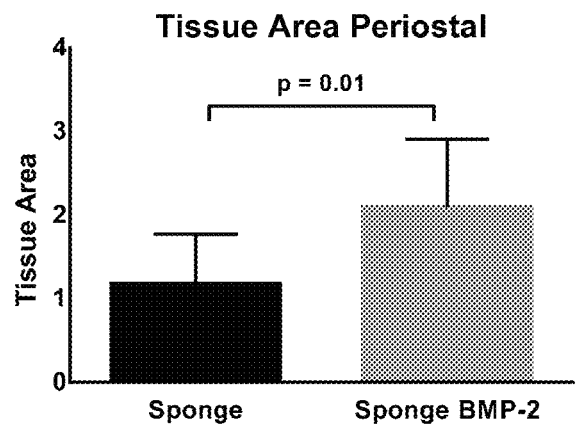
Figure 30C:
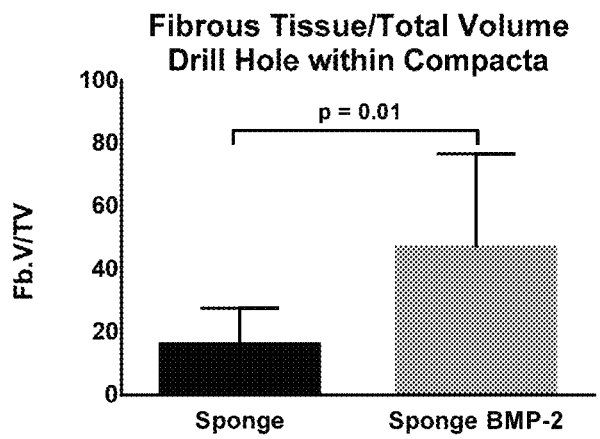
Figure 30D:
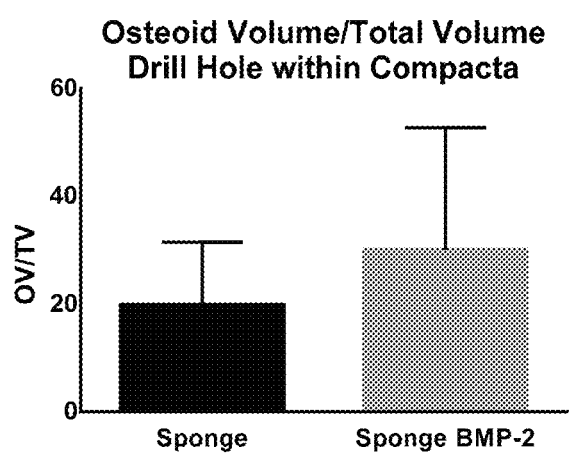
Figure 30E:
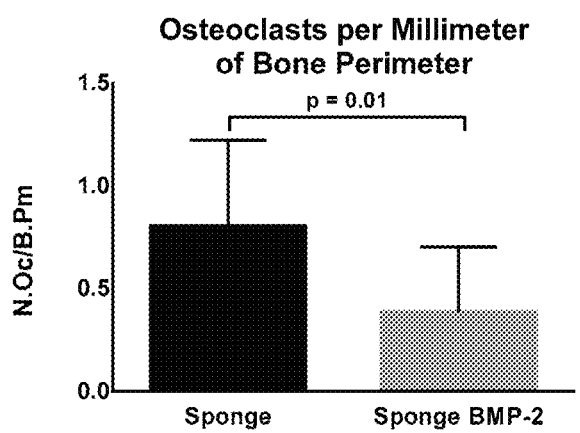
Figure 26:
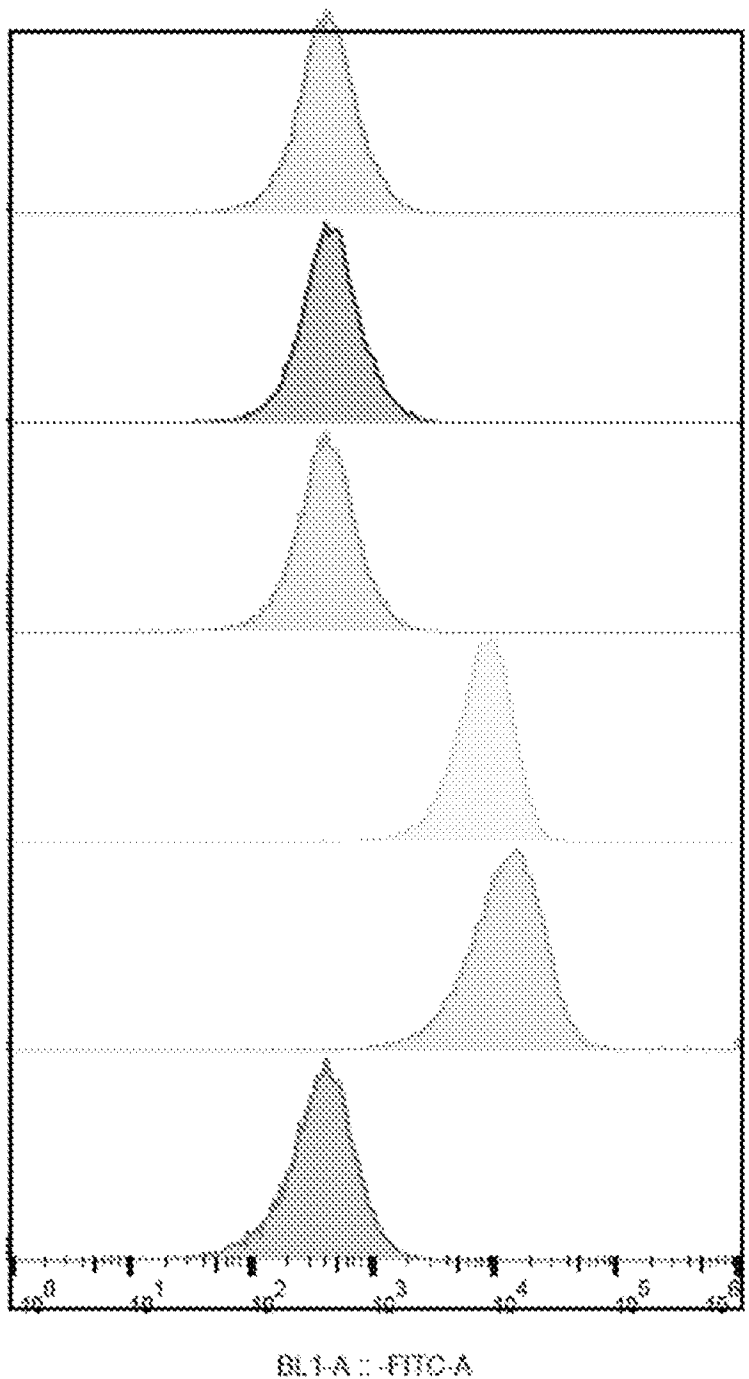

Von Kossa stained slices were examined for exhibiting mineralized tissue, indicating formation of new bone. Using this procedure significantly ($p=0.01$ using Mann-Whitney's U-Test) higher amount of mineralized tissue per tissue volume (BV/TV) was found in the area M4 in the drill hole which implanted with Collagen sponges loaded with cmRNA coding for hBMP-2, indicating enhanced bone formation at the outer surface of the implant in the bone marrow. Formation of bone was expected at this localization though hemopoetic stem cells would most likely have most intensive contact to the implant at the periphery surface (FIG. 30A).

The periostal area surrounding the drill hole (M1) exhibited higher amount of tissue in total in bones implanted with hBMP-2 coding cmRNA-loaded sponges than in bones merely implanted with empty sponges, indicating increased osteogenic activity as a consequence to overexpression of functional hBMP-2 (FIG. 30.B).

Examination of toluol blue stained slices exhibited significantly higher fibrous tissue in in the area of drill holes within the compacta (M2) upon the implantation of Collagen sponges loaded with hBMP-2 coding cmRNA (FIG. 30.C). Moreover, not only higher fibrous tissue was objected, but also increased formation of the fibrous tissue towards osteoids (FIG. 30.D), indicating higher formation of the extracellular matrix in means as precursors of new developing bone tissue.

TRAcP staining exhibited significantly less osteoclasts per millimeter of bone perimeter (N.Oc/B.Pm) within the compacta area (M2) upon treatment with Collagen sponges loaded with cmRNA coding hBMP-2, indicating less bone resorption due to inflammatory processes in the bone surface of the drill hole (FIG. 30.E).

Example 14. Stability Assay of Vacuum-Dried cmRNA Lipoplexes on Collagen Sponges Long-term stability assessment was performed to estimate the shelf life of vacuum-dried cmRNA lipoplexes on collagen sponges as bio-products. For this purpose, 96-well plates containing vacuum-dried Met luc cmRNA lipoplexes on collagen sponges, were vacuum-sealed and stored at RT. At certain time points, one of the plates was used to seed NIH3T3 cells on the sponges. 24 h post cell seeding, expression of *Metridia* luciferase was measured. The expressions from plates stored for different time points were then compared to that of the plate which had been used directly after vacuum-drying (time point=0). As shown in FIG. 9, regardless of the applied cmRNA doses, vacuum-dried cmRNA complexes on the collagen sponges are stable at least for 6 months at RT.

The present invention refers to the following tables:

TABLE 1

Characteristics of the DF-Gold/hBMP-2 cmRNA lipoplexes and SO-Mag6-115/DF-Gold/hBMP-2 cmRNA magnetic lipoplexes formulated at an iron-to-cmRNA ratio (w/w) of 0.5:1. Each value represents the mean ± SD (n = 30).

| Complex | Assembling medium | Mean hydrated diameter Dh (nm) | Polydispersity index, PDI | Electrokinetic potential ξ (mV) |
|---|---|---|---|---|
| Lipoplexes | Water | 104 ± 2 | 0.36 ± 0.008 | +57.4 ± 0.6 |
| Magnetic lipoplexes | | 146 ± 12 | 0.39 ± 0.008 | +53.7 ± 1.4 |
| Lipoplexes | 150 mM NaCl | 121 ± 2 | 0.37 ± 0.002 | +50.4 ± 4.4 |
| Magnetic lipoplexes | | 219 ± 3 | 0.5 ± 0.03 | +54.2 ± 1.9 |
| Lipoplexes | Opti-MEM | 471 ± 49 | 0.23 ± 0.01 | +14.1 ± 1.1 |
| Magnetic lipoplexes | | 398 ± 56 | 0.21 ± 0.03 | +8.7 ± 1.3 |

TABLE 2

Description of designed rat primers used in the qRT-PCR assay.

| Gene | Forward and reverse primers (SEQ ID No.) | Fragment length (bp) |
|---|---|---|
| Rat runt-related transcription factor 2, RunX2 (NM_053470.2) | For: ccgtgtcagcaaaacttctttt (5)<br>Rev: gctcacgtcgctcatcttg (6) | 96 |
| Rat alkaline phosphatase, ALP (NM_013059.1) | For: tggaacactgggtoccata (7)<br>Rev: gacctggtettccaccaa (8) | 68 |
| Rat osterix, Osx (AY177399.1) | For: cccaactgtcaggagctagag (9)<br>Rev: gatgtggcggctgtgaat (10) | 78 |
| Rat collagen type I alpha 1, CollIa1 (NM_053304.1) | For: tgcttgaagacctatgtgggta (11)<br>Rev: aaaggcagcatttggggtat (12) | 71 |
| Rat bone gamma-carboxyglutamate protein, Bglap or OCN (NM_013414.1) | For: acggcagcttcagctttg (13)<br>Rev: gaggcagagagagggaacag (14) | 63 |
| Rat osteopontin, OPN (M99252.1) | For: atcgacagtcaggcgagttc (15)<br>Rev: gctgtgaaactcgtggctct (16) | 60 |
| Rat tubulin beta 2A class IIa, Tubb2a (NM_001109119.1) | For: ctgatgagcagggcgagt (17)<br>Rev: tccgagaagttcttaagcctca (18) | 62 |

TABLE 3

Description of designed human primers used in the qRT-PCR assay.

| Gene | Forward and reverse primers (SEQ ID No.) | Fragment length (bp) |
|---|---|---|
| Human bone morphogenetic protein 2, BMP2 (NM_001200) | For: ccccctacatgctagacctgt (19)<br>Rev: cactcgtttctggtagttcttcc (20) | 150 |
| Human runt-related transcription factor 2, RunX2 V2 (NM_001015051.3) | For: tgcctaggcgcatttcaggtgc (21)<br>Rev: tgaggtgactggcggggtgt (22) | 149 |
| Human alkaline phosphatase, ALP V1 (NM_000478.4) | For: acgtggctaagaatgtcatc (23)<br>Rev: ctggtaggcgatgtcctta (24) | 475 |
| Human collagen, type I, alpha 1, COL1A1 (NM_000088.3) | For: cagccgcttcacctacagc (25)<br>Rev: tmgtattcaatcactgtcttgcc (26) | 83 |
| Human tubulin beta 2A class IIa, Tubb2a (NM_001069.2) | For: gagggcgaggacgaggctta (27)<br>Rev: tctaacagaggcaaaactgagcacc (28) | 122 |

TABLE 4

Examples of suitable modifications in the cmRNA to be employed.

| Name | Base modification (5-position) | Sugar modification (2'-position) | Naturally in mRNA |
|---|---|---|---|
| Uridine | | | |
| 5-methyluridine 5'-triphosphate (m5U) | $CH_3$ | — | no |
| 5-idouridine 5'-triphosphate (I5U) | I | — | no |
| 5-bromouridine 5'-triphosphate (Br5U) | Br | — | no |
| 2-thiouridine 5'-triphosphate (S2U) | S (in 2 position) | — | no |
| 4-thiouridine 5'-triphosphate (S4U) | S (in 4 position) | — | no |
| 2'-methyl-2'-deoxyuridine 5'-triphosphate (U2'm) | — | $CH_3$ | yes |
| 2'-amino-2'-deoxyuridine 5'-triphosphate (U2'NH2) | — | $NH_2$ | no |
| 2'-azido-2'-deoxyuridine 5'-triphosphate (U2'N3) | — | $N_3$ | no |
| 2'-fluoro-2'-deoxyuridine 5'-triphosphate (U2'F) | — | F | no |
| Cytidine | | | |
| 5-methylcytidine 5'-triphosphate (m5C) | $CH_3$ | — | yes |
| 5-idocytidine 5'-triphosphate (I5U) | I | — | no |
| 5-bromocytidine 5'-triphosphate (Br5U) | Br | — | no |
| 2-thiocytidine 5'-triphosphate (S2C) | S (in 2 position) | — | no |
| 2'-methyl-2'-deoxycytidine 5'-triphosphate (C2'm) | — | $CH_3$ | yes |
| 2'-amino-2'-deoxycytidine 5'-triphosphate (C2'NH2) | — | $NH_2$ | no |
| 2'-azido-2'-deoxycytidine 5'-triphosphate (C2'N3) | — | $N_3$ | no |
| 2'-fluoro-2'-deoxycytidine 5'-triphosphate (C2'F) | — | F | no |
| Adenosine | | | |
| N6-methyladenosine 5'-triphosphate (m6A) | $CH_3$ (in 6 position) | — | yes |
| N1-methyladenosine 5'-triphosphate (m1A) | $CH_3$ (in 1 position) | — | no |
| 2'-O-methyladenosine 5'-triphosphate (A2'm) | — | $CH_3$ | yes |
| 2'-amino-2'-deoxyadenosine 5'-triphosphate (A2'NH2) | — | $NH_2$ | no |
| 2'-azido-2'-deoxyadenosine 5'-triphosphate (A2'N3) | — | $N_3$ | no |
| 2'-fluoro-2'-deoxyadenosine 5'-triphosphate (A2'F) | — | F | no |
| Guanosine | | | |
| N1-methylguanosine 5'-triphosphate (m1G) | $CH_3$ (in 1 position) | — | no |
| 2'-O-methylguanosine 5'-triphosphate (G2'm) | — | $CH_3$ | yes |
| 2'-amino-2'-deoxyguanosine 5'-triphosphate (G2'NH2) | — | $NH_2$ | no |
| 2'-azido-2'-deoxyguanosine 5'-triphosphate (G2'N3) | — | $N_3$ | no |
| 2'-fluoro-2'-deoxyguanosine 5'-triphosphate (G2'F) | — | F | no |

TABLE 5

Database entries for nucleotide and amino acid sequences of BMPs.

| Target | Nucleotide Acc. Nr. (NCBI) | Protein Acc. Nr. (NCBI) |
|---|---|---|
| hBmp1 transcript variant 1 | NM_001199 (18-Oct-2014) | NP_001190 (11-MAY-2014) |
| hBmp1 transcript variant 3 | NM_006129 (18-Oct-2014) | NP_006120 (11-MAY-2014) |
| hBmp2 mRNA | NM_001200 (23-Oct-2014) | NP_001191 (03-MAY-2014) |
| hBmp3 mRNA | NM_001201 (23-Oct-2014) | NP_001192 (26-FEB-2014) |

TABLE 5-continued

Database entries for nucleotide and amino acid sequences of BMPs.

| Target | Nucleotide Acc. Nr. (NCBI) | Protein Acc. Nr. (NCBI) |
|---|---|---|
| hBmp4 transcript variant 1 | NM_001202 (23-Oct-2014) | NP_001193 (03-MAY-2014) |
| hBmp4 transcript variant 2 | NM_130850 (23-Oct-2014) | NP_570911 (27-APR-2014) |
| hBmp4 transcript variant 3 | NM_130851 (23-Oct-2014) | NP_570912 (27-APR-2014) |
| hBmp5 mRNA | NM_021073 (23-Oct-2014) | NP_066551 (26-JAN-2014) |
| hBmp6 mRNA | NM_001718 (23-Oct-2014) | NP_001709 (20-APR-2014) |
| hBmp7 mRNA | NM_001719 (23-Oct-2014 | NP_001710 (25-MAY-2014) |
| hBmp8a mRNA | NM_181809 (11-Oct-2014) | NP_861525 (26-FEB-2014) |
| hBmp8b mRNA | NM_001720 (5-Oct-2014) | NP_001711 (26-FEB-2014) |
| hBmp10 mRNA | NM_014482 (23-Oct-2014) | NP_055297 (03-MAY-2014) |
| hBmp15 mRNA | NM_005448 (23-Oct-2014) | NP_005439 (03-MAY-2014) |

TABLE 6 mRNA complexes' characteristics.

| mRNA Complex | Mean Hydrodynamic Diameter (nm) | SD Hydrodynamic Diameter (nm) | Poly Dispersity Index (PDI) | Zetta Potential (mV) |
|---|---|---|---|---|
| eGFP | 45.86 | 0.34 | 0.061 | 0.82 |
| Met luc | 69.95 | 0.26 | 0.177 | 0.464 |
| hBMP2 | 51.84 | 0.84 | 0.094 | 0.27 |

The present invention refers to the following (additional) references:

1. Balmayor, Stem Cell Therapy for Bone Disorders. In: Chase L G, Vemuri M C (eds.) Mesenchymal Stem Cell Therapy. Humana Press, New York 2012, 101-116
2. Carmona, Bone Health and Osteoporosis: A Report of the Surgeon General 2004, U.S. Department of Health and Human Services, Office of the Surgeon General, Rockville, MD
3. Dimitriou, Injury 36(12), 2005, 1392-1404
4. Einhorn, Clin Orthop Relat Res 355, 1998, 7-21
5. Tanner, J R Soc Interface 5, 2010, 541-557
6. Tanner, Proc Inst Mech Eng H 224(12), 2010, 1359-1372
7. Mourino, Expert Opin Drug Deliv 10(10), 2013, 1353-1365
8. Romagnoli, Clin Cases Miner Bone Metab 10(3), 2013, 155-161
9. Bessa, J Tissue Eng Regen Med 2(2-3), 2008, 81-96
10. Bessa, J Tissue Eng Regen Med 2(1), 2008, 1-13
11. Urist, Clin Orthop Relat Res 53, 1967, 243-283
12. Yamaguchi, Endocr Rev 21(4), 2000, 393-411
13. Keibl, Injury 42(8), 2011, 814-820
14. Katagiri, J Cell Biol 127(6 Pt 1), 1994, 1755-1766
15. Shekaran, Bone regeneration using an alpha 2 beta 1 integrin-specific hydrogel as a BMP-2 delivery vehicle. Biomaterials, 2014
16. Evans, Adv Drug Deliv Rev 64(12), 2012, 1331-1340
17. Lu, J Biomater Sci Polym Ed 23(1-4), 2012, 509-526
18. Chang, Neurosurgery 65, 2009, 75-81
19. Park, Gene Ther 10(13), 2003, 1089-1098
20. Van Tendeloo, Curr Opin Mol Ther 9(5), 2007, 423-431
21. Holtkamp, Blood 108(13), 2006, 4009-4017
22. Kormann, Nat Biotechnol 29(2), 2011, 154-157
23. Mays, J Clin Invest 123(3), 2013, 1216-1228
24. Balmayor, Biores Open Access 2(5), 2013, 346-355
25. Evans, Eur Cell Mater 18, 2009, 96-111
26. Puri, J Lipid Res 48(2), 2007, 465-471
27. Mykhaylyk, Liposomal magnetofection. In: Weissig V (ed.) Liposomes, Methods in Molecular Biology, vol. 605. Humana Press-Springer, New York 2010, 487-525
28. Mykhaylyk, Pharm Res 29(5), 2012, 1344-1365
29. Inouye, Protein Expr Purif 88(1), 2013, 150-156
30. Cox, J Histochem Cytochem 47(11), 1999, 1443-1456
31. Lakshmipathy, Stem cells 22(4), 2004, 531-543
32. Evans, Tissue Eng 13(8), 2007, 1987-1993
33. Dragoo, Plast Reconstr Surg 115(6), 2005, 1665-1673

The invention claimed is:

1. A method of treating or preventing a bone disease, bone disorder or bone injury comprising administering to a patient in need thereof a pharmaceutical composition comprising (i) a polyribonucleotide (RNA) with a sequence which encodes a bone morphogenetic protein (BMP); and (ii) a component comprising an oligo (alkylene amine) being a cationic lipidoid having the structure of formula (IV):

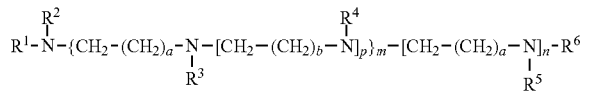

wherein the variables a, b, p, m, n and $R^1$ to $R^6$ are defined as follows:
 a is 1 and b is 2;
 p is 1,
 m is 1 and n is 1; and
 $R^1$ to $R^6$ are independently of each other hydrogen, —$CH_2$—CH(OH)—$R^7$, —CH($R^7$)—$CH_2$—OH, —$CH_2$—$CH_2$—(C=O)—NH—$R^7$, or —$CH_2$—$R^7$, wherein $R^7$ is C3-C18 alkyl or C3-C18 alkenyl having one C—C double bond; provided that one of $R^1$, $R^2$, $R^5$, and $R^6$ is hydrogen; and wherein one or more of the nitrogen atoms indicated in formula (IV) may be protonated.

2. The method of claim 1, wherein said BMP is BMP-2 or BMP-7.

3. The method of claim 1, wherein said RNA forms a complex with said cationic lipidoid.

4. The method of claim 1, wherein said RNA is delivered in vivo.

5. The method of claim 1, wherein said RNA is delivered ex vivo into cells which are to be introduced into said patient.

6. The method of claim 1, wherein said RNA is administered into or in close proximity to the tissue of said patient in which induction of bone growth is desired.

7. The method of claim 5, wherein said cells are mesenchymal stem cells (MSCs) or osteoprogenitor cells.

8. The method of claim 7, wherein said MSCs are adipose-derived mesenchymal stem cells (AMSCs) or bone marrow-derived MSCs (BMSCs).

9. The method of claim 1, wherein the pharmaceutical composition further comprises a matrix or scaffold to which said RNA has been added or into which said RNA has been loaded.

10. The method of claim 9, wherein said matrix or scaffold comprises collagen and/or fibrin.

11. The method of claim 9, wherein said matrix or scaffold is vacuum-dried.

12. The method of claim 5, wherein said cells have been seeded on a matrix or scaffold.

13. The method of claim 9, wherein said matrix or scaffold is transplanted into the bone of said patient.

14. The method of claim 1, wherein the RNA is chemically modified, and wherein 25% of the cytidines of said chemically modified RNA are 5-methylcytidines (m5C) and 25% of the uridines of said chemically modified RNA are 2-thiouridines (s2U).

15. The method of claim 1, wherein said RNA is a single-stranded RNA.

16. The method of claim 1, wherein said pharmaceutical composition further comprises one or more of cholesterol, DPPC, DOPE and PEG-lipids.

17. The method of claim 1, wherein said pharmaceutical composition further comprises (i) DOPE, cholesterol and DMPE-PEG (2k); or
(ii) DPPC, cholesterol and DMG-PEG (2k).

18. The method of claim 17, wherein the molar ratios of said lipidoid and (i) or (ii) are 8/5.3/4.4/0.9 or 8:5.29:4.41:0.88.

19. A method of treating or preventing a bone disease, bone disorder or bone injury comprising administering to a patient in need thereof a pharmaceutical composition comprising (i) a polyribonucleotide (RNA) with a sequence which encodes a bone morphogenetic protein (BMP); (ii) dipalmitoyl phosphatidylcholine (DPPC) and (iii) a component comprising an oligo (alkylene amine) being a cationic lipidoid having the structure of formula (IV):

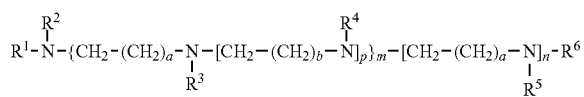

(IV)

wherein the variables a, b, p, m, n and R1 to R6 are defined as follows:
a is 1 and b is 2;
p is 1,
m is 1 and n is 1; and
$R^1$ to $R^6$ are independently of each other hydrogen, $-CH_2-CH(OH)-R^7$, $-CH(R^7)-CH_2-OH$, $-CH_2-CH_2-(C=O)-O-R^7$, $-CH_2-CH_2-(C=O)-NH-R^7$ or $-CH_2-R^7$, wherein $R^7$ is C3-C18 alkyl or C3-C18 alkenyl having one C—C double bond; provided that one of $R^1$, $R^2$, $R^5$, and $R^6$ is hydrogen; and wherein one or more of the nitrogen atoms indicated in formula (IV) may be protonated.

20. A method of treating or preventing a bone disease, bone disorder or bone injury comprising administering to a patient in need thereof a pharmaceutical composition comprising (i) a polyribonucleotide (RNA) with a sequence which encodes a bone morphogenetic protein (BMP); and (ii) a component comprising an oligo (alkylene amine) prepared by mixing N,N'-Bis (2-aminoethyl)-1,3-propanediamine with 1,2-Epoxydodecane in a molar ratio of 1:5, and wherein the cationic lipidoid thus obtained has being a cationic lipidoid having the structure of formula (IV):

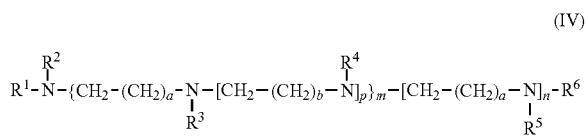

(IV)

wherein the variables a, b, p, m, n and $R^1$ to $R^6$ are defined as follows:
a is 1 and b is 2;
p is 1,
m is 1 and n is 1; and
$R^1$ to $R^6$ are independently of each other selected from hydrogen, $CH_2-CH$ (OH)$-R^7$, and $-CH(R^7)-CH_2-OH$, wherein $R^7$ is C10 alkyl; provided that five of $R^1$ to $R^6$ are selected from $CH_2-CH(OH)-R^7$ and $-CH(R^7)-CH_2-OH$, and one of $R^1$, $R^2$, $R^5$, and $R^6$ is hydrogen; and wherein one or more of the nitrogen atoms indicated in formula (IV) may be protonated.

* * * * *

UNITED STATES PATENT AND TRADEMARK OFFICE
CERTIFICATE OF CORRECTION

Page 1 of 2

PATENT NO. : 12,263,229 B2
APPLICATION NO. : 15/525701
DATED : April 1, 2025
INVENTOR(S) : Elizabeth Balmayor et al.

It is certified that error appears in the above-identified patent and that said Letters Patent is hereby corrected as shown below:

In the Drawings

Replace Figure 26 on Sheet 32 with the Replacement Figure 26 shown on the attached drawing sheet.

Signed and Sealed this
Sixteenth Day of September, 2025

Coke Morgan Stewart
*Acting Director of the United States Patent and Trademark Office*

SEQUENCE LISTING

```
<160> NUMBER OF SEQ ID NOS: 47

<210> SEQ ID NO 1
<211> LENGTH: 1191
<212> TYPE: DNA
<213> ORGANISM: Homo sapiens
<220> FEATURE:
<221> NAME/KEY: CDS
<222> LOCATION: 1..1191
<223> OTHER INFORMATION: /transl_table=1

<400> SEQUENCE: 1 atg gtg gcc ggg acc cgc tgt ctt cta gcg ttg ctg ctt ccc cag gtc      48
Met Val Ala Gly Thr Arg Cys Leu Leu Ala Leu Leu Leu Pro Gln Val
1               5                   10                  15 ctc ctg ggc ggc gcg gct ggc ctc gtt ccg gag ctg ggc cgc agg aag      96
Leu Leu Gly Gly Ala Ala Gly Leu Val Pro Glu Leu Gly Arg Arg Lys
            20                  25                  30 ttc gcg gcg gcg tcg tcg ggc cgc ccc tca tcc cag ccc tct gac gag     144
```

```
            Phe Ala Ala Ala Ser Ser Gly Arg Pro Ser Ser Gln Pro Ser Asp Glu
                     35                  40                  45 gtc ctg agc gag ttc gag ttg cgg ctg ctc agc atg ttc ggc ctg aaa            192
Val Leu Ser Glu Phe Glu Leu Arg Leu Leu Ser Met Phe Gly Leu Lys
 50                  55                  60 cag aga ccc acc ccc agc agg gac gcc gtg gtg ccc ccc tac atg cta            240
Gln Arg Pro Thr Pro Ser Arg Asp Ala Val Val Pro Pro Tyr Met Leu
 65                  70                  75                  80 gac ctg tat cgc agg cac tca ggt cag ccg ggc tca ccc gcc cca gac            288
Asp Leu Tyr Arg Arg His Ser Gly Gln Pro Gly Ser Pro Ala Pro Asp
                     85                  90                  95 cac cgg ttg gag agg gca gcc agc cga gcc aac act gtg cgc agc ttc            336
His Arg Leu Glu Arg Ala Ala Ser Arg Ala Asn Thr Val Arg Ser Phe
                    100                 105                 110 cac cat gaa gaa tct ttg gaa gaa cta cca gaa acg agt ggg aaa aca            384
His His Glu Glu Ser Leu Glu Glu Leu Pro Glu Thr Ser Gly Lys Thr
                    115                 120                 125 acc cgg aga ttc ttc ttt aat tta agt tct atc ccc acg gag gag ttt            432
Thr Arg Arg Phe Phe Phe Asn Leu Ser Ser Ile Pro Thr Glu Glu Phe
130                 135                 140 atc acc tca gca gag ctt cag gtt ttc cga gaa cag atg caa gat gct            480
Ile Thr Ser Ala Glu Leu Gln Val Phe Arg Glu Gln Met Gln Asp Ala
145                 150                 155                 160 tta gga aac aat agc agt ttc cat cac cga att aat att tat gaa atc            528
Leu Gly Asn Asn Ser Ser Phe His His Arg Ile Asn Ile Tyr Glu Ile
                    165                 170                 175 ata aaa cct gca aca gcc aac tcg aaa ttc ccc gtg acc aga ctt ttg            576
Ile Lys Pro Ala Thr Ala Asn Ser Lys Phe Pro Val Thr Arg Leu Leu
                    180                 185                 190 gac acc agg ttg gtg aat cag aat gca agc agg tgg gaa agt ttt gat            624
Asp Thr Arg Leu Val Asn Gln Asn Ala Ser Arg Trp Glu Ser Phe Asp
                    195                 200                 205 gtc acc ccc gct gtg atg cgg tgg act gca cag gga cac gcc aac cat            672
Val Thr Pro Ala Val Met Arg Trp Thr Ala Gln Gly His Ala Asn His
                    210                 215                 220 gga ttc gtg gtg gaa gtg gcc cac ttg gag gag aaa caa ggt gtc tcc            720
Gly Phe Val Val Glu Val Ala His Leu Glu Glu Lys Gln Gly Val Ser
225                 230                 235                 240 aag aga cat gtt agg ata agc agg tct ttg cac caa gat gaa cac agc            768
Lys Arg His Val Arg Ile Ser Arg Ser Leu His Gln Asp Glu His Ser
                    245                 250                 255 tgg tca cag ata agg cca ttg cta gta act ttt ggc cat gat gga aaa            816
Trp Ser Gln Ile Arg Pro Leu Leu Val Thr Phe Gly His Asp Gly Lys
                    260                 265                 270 ggg cat cct ctc cac aaa aga gaa aaa cgt caa gcc aaa cac aaa cag            864
Gly His Pro Leu His Lys Arg Glu Lys Arg Gln Ala Lys His Lys Gln
                    275                 280                 285 cgg aaa cgc ctt aag tcc agc tgt aag aga cac cct ttg tac gtg gac            912
Arg Lys Arg Leu Lys Ser Ser Cys Lys Arg His Pro Leu Tyr Val Asp
290                 295                 300 ttc agt gac gtg ggg tgg aat gac tgg att gtg gct ccc ccg ggg tat            960
Phe Ser Asp Val Gly Trp Asn Asp Trp Ile Val Ala Pro Pro Gly Tyr
305                 310                 315                 320 cac gcc ttt tac tgc cac gga gaa tgc cct ttt cct ctg gct gat cat           1008
His Ala Phe Tyr Cys His Gly Glu Cys Pro Phe Pro Leu Ala Asp His
                    325                 330                 335 ctg aac tcc act aat cat gcc att gtt cag acg ttg gtc aac tct gtt           1056
Leu Asn Ser Thr Asn His Ala Ile Val Gln Thr Leu Val Asn Ser Val
                    340                 345                 350
```

```
aac tct aag att cct aag gca tgc tgt gtc ccg aca gaa ctc agt gct       1104
Asn Ser Lys Ile Pro Lys Ala Cys Cys Val Pro Thr Glu Leu Ser Ala
        355                 360                 365 atc tcg atg ctg tac ctt gac gag aat gaa aag gtt gta tta aag aac       1152
Ile Ser Met Leu Tyr Leu Asp Glu Asn Glu Lys Val Val Leu Lys Asn
370                 375                 380 tat cag gac atg gtt gtg gag ggt tgt ggg tgt cgc tag                   1191
Tyr Gln Asp Met Val Val Glu Gly Cys Gly Cys Arg
385                 390                 395

<210> SEQ ID NO 2
<211> LENGTH: 1296
<212> TYPE: DNA
<213> ORGANISM: Homo sapiens
<220> FEATURE:
<221> NAME/KEY: CDS
<222> LOCATION: 1..1296
<223> OTHER INFORMATION: /transl_table=1

<400> SEQUENCE: 2 atg cac gtg cgc tca ctg cga gct gcg gcg ccg cac agc ttc gtg gcg        48
Met His Val Arg Ser Leu Arg Ala Ala Ala Pro His Ser Phe Val Ala
1               5                   10                  15 ctc tgg gca ccc ctg ttc ctg ctg cgc tcc gcc ctg gcc gac ttc agc        96
Leu Trp Ala Pro Leu Phe Leu Leu Arg Ser Ala Leu Ala Asp Phe Ser
                20                  25                  30 ctg gac aac gag gtg cac tcg agc ttc atc cac cgg cgc ctc cgc agc       144
Leu Asp Asn Glu Val His Ser Ser Phe Ile His Arg Arg Leu Arg Ser
            35                  40                  45 cag gag cgg cgg gag atg cag cgc gag atc ctc tcc att ttg ggc ttg       192
Gln Glu Arg Arg Glu Met Gln Arg Glu Ile Leu Ser Ile Leu Gly Leu
        50                  55                  60 ccc cac cgc ccg cgc ccg cac ctc cag ggc aag cac aac tcg gca ccc       240
Pro His Arg Pro Arg Pro His Leu Gln Gly Lys His Asn Ser Ala Pro
65                  70                  75                  80 atg ttc atg ctg gac ctg tac aac gcc atg gcg gtg gag gag ggc ggc       288
Met Phe Met Leu Asp Leu Tyr Asn Ala Met Ala Val Glu Glu Gly Gly
                85                  90                  95 ggg ccc ggc ggc cag ggc ttc tcc tac ccc tac aag gcc gtc ttc agt       336
Gly Pro Gly Gly Gln Gly Phe Ser Tyr Pro Tyr Lys Ala Val Phe Ser
            100                 105                 110 acc cag ggc ccc cct ctg gcc agc ctg caa gat agc cat ttc ctc acc       384
Thr Gln Gly Pro Pro Leu Ala Ser Leu Gln Asp Ser His Phe Leu Thr
        115                 120                 125 gac gcc gac atg gtc atg agc ttc gtc aac ctc gtg gaa cat gac aag       432
Asp Ala Asp Met Val Met Ser Phe Val Asn Leu Val Glu His Asp Lys
130                 135                 140 gaa ttc ttc cac cca cgc tac cac cat cga gag ttc cgg ttt gat ctt       480
Glu Phe Phe His Pro Arg Tyr His His Arg Glu Phe Arg Phe Asp Leu
145                 150                 155                 160 tcc aag atc cca gaa ggg gaa gct gtc acg gca gcc gaa ttc cgg atc       528
Ser Lys Ile Pro Glu Gly Glu Ala Val Thr Ala Ala Glu Phe Arg Ile
                165                 170                 175 tac aag gac tac atc cgg gaa cgc ttc gac aat gag acg ttc cgg atc       576
Tyr Lys Asp Tyr Ile Arg Glu Arg Phe Asp Asn Glu Thr Phe Arg Ile
            180                 185                 190 agc gtt tat cag gtg ctc cag gag cac ttg ggc agg gaa tcg gat ctc       624
Ser Val Tyr Gln Val Leu Gln Glu His Leu Gly Arg Glu Ser Asp Leu
        195                 200                 205 ttc ctg ctc gac agc cgt acc ctc tgg gcc tcg gag gag ggc tgg ctg       672
Phe Leu Leu Asp Ser Arg Thr Leu Trp Ala Ser Glu Glu Gly Trp Leu
210                 215                 220
```

```
gtg ttt gac atc aca gcc acc agc aac cac tgg gtg tcc aat ccg cgg    720
Val Phe Asp Ile Thr Ala Thr Ser Asn His Trp Val Val Asn Pro Arg
225                 230                 235                 240 cac aac ctg ggc ctg cag ctc tcg gtg gag acg ctg gat ggg cag agc    768
His Asn Leu Gly Leu Gln Leu Ser Val Glu Thr Leu Asp Gly Gln Ser
                245                 250                 255 atc aac ccc aag ttg gcg ggc ctg att ggg cgg cac ggg ccc cag aac    816
Ile Asn Pro Lys Leu Ala Gly Leu Ile Gly Arg His Gly Pro Gln Asn
            260                 265                 270 aag cag ccc ttc atg gtg gct ttc ttc aag gcc acg gag gtc cac ttc    864
Lys Gln Pro Phe Met Val Ala Phe Phe Lys Ala Thr Glu Val His Phe
        275                 280                 285 cgc agc atc cgg tcc acg ggg agc aaa cag cgc agc cag aac cgc tcc    912
Arg Ser Ile Arg Ser Thr Gly Ser Lys Gln Arg Ser Gln Asn Arg Ser
    290                 295                 300 aag acg ccc aag aac cag gaa gcc ctg cgg atg gcc aac gtg gca gag    960
Lys Thr Pro Lys Asn Gln Glu Ala Leu Arg Met Ala Asn Val Ala Glu
305                 310                 315                 320 aac agc agc agc gac cag agg cag gcc tgt aag aag cac gag ctg tat   1008
Asn Ser Ser Ser Asp Gln Arg Gln Ala Cys Lys Lys His Glu Leu Tyr
                325                 330                 335 gtc agc ttc cga gac ctg ggc tgg cag gac tgg atc atc gcg cct gaa   1056
Val Ser Phe Arg Asp Leu Gly Trp Gln Asp Trp Ile Ile Ala Pro Glu
                340                 345                 350 ggc tac gcc gcc tac tac tgt gag ggg gag tgt gcc ttc cct ctg aac   1104
Gly Tyr Ala Ala Tyr Tyr Cys Glu Gly Glu Cys Ala Phe Pro Leu Asn
            355                 360                 365 tcc tac atg aac gcc acc aac cac gcc atc gtg cag acg ctg gtc cac   1152
Ser Tyr Met Asn Ala Thr Asn His Ala Ile Val Gln Thr Leu Val His
        370                 375                 380 ttc atc aac ccg gaa acg gtg ccc aag ccc tgc tgt gcg ccc acg cag   1200
Phe Ile Asn Pro Glu Thr Val Pro Lys Pro Cys Cys Ala Pro Thr Gln
385                 390                 395                 400 ctc aat gcc atc tcc gtc ctc tac ttc gat gac agc tcc aac gtc atc   1248
Leu Asn Ala Ile Ser Val Leu Tyr Phe Asp Asp Ser Ser Asn Val Ile
                405                 410                 415 ctg aag aaa tac aga aac atg gtg gtc cgg gcc tgt ggc tgc cac tag   1296
Leu Lys Lys Tyr Arg Asn Met Val Val Arg Ala Cys Gly Cys His
                420                 425                 430

<210> SEQ ID NO 3
<211> LENGTH: 396
<212> TYPE: PRT
<213> ORGANISM: Homo sapiens
<220> FEATURE:
<223> OTHER INFORMATION: [CDS]:1..1191 from SEQ ID NO 1

<400> SEQUENCE: 3

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
        50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
```

```
                85                  90                  95
His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 4
<211> LENGTH: 431
<212> TYPE: PRT
<213> ORGANISM: Homo sapiens
<220> FEATURE:
<223> OTHER INFORMATION: [CDS]:1..1296 from SEQ ID NO 2

<400> SEQUENCE: 4

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
```

```
                50                  55                  60
Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His Arg Glu Phe Arg Phe Asp Leu
145                 150                 155                 160

Ser Lys Ile Pro Glu Gly Glu Ala Val Thr Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 5
<211> LENGTH: 21
<212> TYPE: DNA
<213> ORGANISM: Artificial Sequence
<220> FEATURE:
<223> OTHER INFORMATION: forward primer
```

<400> SEQUENCE: 5
ccgtgtcagc aaaacttctt t                                              21

<210> SEQ ID NO 6
<211> LENGTH: 19
<212> TYPE: DNA
<213> ORGANISM: Artificial Sequence
<220> FEATURE:
<223> OTHER INFORMATION: reverse primer

<400> SEQUENCE: 6
gctcacgtcg ctcatcttg                                                 19

<210> SEQ ID NO 7
<211> LENGTH: 19
<212> TYPE: DNA
<213> ORGANISM: Artificial Sequence
<220> FEATURE:
<223> OTHER INFORMATION: forward primer

<400> SEQUENCE: 7
tggaacactg ggtcccata                                                 19

<210> SEQ ID NO 8
<211> LENGTH: 19
<212> TYPE: DNA
<213> ORGANISM: Artificial Sequence
<220> FEATURE:
<223> OTHER INFORMATION: reverse primer

<400> SEQUENCE: 8
gacctggtct tccctccaa                                                 19

<210> SEQ ID NO 9
<211> LENGTH: 21
<212> TYPE: DNA
<213> ORGANISM: Artificial Sequence
<220> FEATURE:
<223> OTHER INFORMATION: forward primer

<400> SEQUENCE: 9
cccaactgtc aggagctaga g                                              21

<210> SEQ ID NO 10
<211> LENGTH: 18
<212> TYPE: DNA
<213> ORGANISM: Artificial Sequence
<220> FEATURE:
<223> OTHER INFORMATION: reverse primer

<400> SEQUENCE: 10
gatgtggcgg ctgtgaat                                                  18

<210> SEQ ID NO 11
<211> LENGTH: 22
<212> TYPE: DNA
<213> ORGANISM: Artificial Sequence
<220> FEATURE:
<223> OTHER INFORMATION: forward primer

<400> SEQUENCE: 11
tgcttgaaga cctatgtggg ta                                             22

<210> SEQ ID NO 12
<211> LENGTH: 20

```
<212> TYPE: DNA
<213> ORGANISM: Artificial Sequence
<220> FEATURE:
<223> OTHER INFORMATION: reverse primer

<400> SEQUENCE: 12
aaaggcagca tttggggtat                                              20

<210> SEQ ID NO 13
<211> LENGTH: 18
<212> TYPE: DNA
<213> ORGANISM: Artificial Sequence
<220> FEATURE:
<223> OTHER INFORMATION: forward primer

<400> SEQUENCE: 13
acggcagctt cagctttg                                                18

<210> SEQ ID NO 14
<211> LENGTH: 20
<212> TYPE: DNA
<213> ORGANISM: Artificial Sequence
<220> FEATURE:
<223> OTHER INFORMATION: reverse primer

<400> SEQUENCE: 14
gaggcagaga gagggaacag                                              20

<210> SEQ ID NO 15
<211> LENGTH: 20
<212> TYPE: DNA
<213> ORGANISM: Artificial Sequence
<220> FEATURE:
<223> OTHER INFORMATION: forward primer

<400> SEQUENCE: 15
atcgacagtc aggcgagttc                                              20

<210> SEQ ID NO 16
<211> LENGTH: 20
<212> TYPE: DNA
<213> ORGANISM: Artificial Sequence
<220> FEATURE:
<223> OTHER INFORMATION: reverse primer

<400> SEQUENCE: 16
gctgtgaaac tcgtggctct                                              20

<210> SEQ ID NO 17
<211> LENGTH: 18
<212> TYPE: DNA
<213> ORGANISM: Artificial Sequence
<220> FEATURE:
<223> OTHER INFORMATION: forward primer

<400> SEQUENCE: 17
ctgatgagca gggcgagt                                                18

<210> SEQ ID NO 18
<211> LENGTH: 22
<212> TYPE: DNA
<213> ORGANISM: Artificial Sequence
<220> FEATURE:
<223> OTHER INFORMATION: reverse primer

<400> SEQUENCE: 18
```
tccgagaagt tcttaagcct ca                                                22

<210> SEQ ID NO 19
<211> LENGTH: 21
<212> TYPE: DNA
<213> ORGANISM: Artificial Sequence
<220> FEATURE:
<223> OTHER INFORMATION: forward primer

<400> SEQUENCE: 19 cccctacat gctagacctg t                                                  21

<210> SEQ ID NO 20
<211> LENGTH: 23
<212> TYPE: DNA
<213> ORGANISM: Artificial Sequence
<220> FEATURE:
<223> OTHER INFORMATION: reverse primer

<400> SEQUENCE: 20
cactcgtttc tggtagttct tcc                                               23

<210> SEQ ID NO 21
<211> LENGTH: 22
<212> TYPE: DNA
<213> ORGANISM: Artificial Sequence
<220> FEATURE:
<223> OTHER INFORMATION: forward primer

<400> SEQUENCE: 21
tgcctaggcg catttcaggt gc                                                22

<210> SEQ ID NO 22
<211> LENGTH: 20
<212> TYPE: DNA
<213> ORGANISM: Artificial Sequence
<220> FEATURE:
<223> OTHER INFORMATION: reverse primer

<400> SEQUENCE: 22
tgaggtgact ggcggggtgt                                                   20

<210> SEQ ID NO 23
<211> LENGTH: 20
<212> TYPE: DNA
<213> ORGANISM: Artificial Sequence
<220> FEATURE:
<223> OTHER INFORMATION: forward primer

<400> SEQUENCE: 23
acgtggctaa gaatgtcatc                                                   20

<210> SEQ ID NO 24
<211> LENGTH: 19
<212> TYPE: DNA
<213> ORGANISM: Artificial Sequence
<220> FEATURE:
<223> OTHER INFORMATION: reverse primer

<400> SEQUENCE: 24
ctggtaggcg atgtcctta                                                    19

<210> SEQ ID NO 25
<211> LENGTH: 19
<212> TYPE: DNA
<213> ORGANISM: Artificial Sequence

```
<220> FEATURE:
<223> OTHER INFORMATION: forward primer

<400> SEQUENCE: 25
cagccgcttc acctacagc                                                    19

<210> SEQ ID NO 26
<211> LENGTH: 25
<212> TYPE: DNA
<213> ORGANISM: Artificial Sequence
<220> FEATURE:
<223> OTHER INFORMATION: reverse primer

<400> SEQUENCE: 26
ttttgtattc aatcactgtc ttgcc                                             25

<210> SEQ ID NO 27
<211> LENGTH: 20
<212> TYPE: DNA
<213> ORGANISM: Artificial Sequence
<220> FEATURE:
<223> OTHER INFORMATION: forward primer

<400> SEQUENCE: 27
gagggcgagg acgaggctta                                                   20

<210> SEQ ID NO 28
<211> LENGTH: 25
<212> TYPE: DNA
<213> ORGANISM: Artificial Sequence
<220> FEATURE:
<223> OTHER INFORMATION: reverse primer

<400> SEQUENCE: 28
tctaacagag gcaaaactga gcacc                                             25

<210> SEQ ID NO 29
<211> LENGTH: 1674
<212> TYPE: DNA
<213> ORGANISM: Artificial Sequence
<220> FEATURE:
<223> OTHER INFORMATION: Sequence of uncapped hBmp2 mRNA when the vector
      is linearized with XbaI

<400> SEQUENCE: 29
gagaataact tgcgcacccc actttgcgcc ggtgcctttg ccccagcgga gcctgcttcg       60
ccatctccga gccccaccgc ccctccactc ctcggccttg cccgacactg agacgctgtt      120
cccagcgtga aaagagagac tgcgcggccg gcacccggga aaggaggag gcaaagaaaa       180 ggaacggaca ttcggtcctt gcgccaggtc ctttgaccag agtttttcca tgtgtgacgct    240 cttttcaatgg acgtgtcccc gcgtgcttct tagacggact gcggtctcct aaaggtcggc    300
caccatggtc gccggcacca gatgtctgct ggctctgctg ctgcctcagg tgctgctggg    360
cggagctgcc ggactggtgc ctgagctggg cagaagaaag ttcgccgctg ccagctctgg    420
cagacccagc agccagcctt ccgacgaggt gctgagcgag ttcgagctgc ggctgctgag    480
catgttcggc ctgaagcaga ggccaccccc agcagagat gccgtggtgc cccctacat      540 gctggacctg tacagacggc acagcggaca gcctggaagc cctgcccctg accacagact    600
ggaaagagcc gccagccggg ccaacaccgt gcggagcttt caccacgagg aaagcctgga    660
agaactgccc gagacaagcg gcaagaccac ccggcggttc ttttttcaacc tgtcctccat    720 ccccaccgaa gagttcatca ccagcgccga actccaggtg ttccgcgagc agatgcagga    780
```

```
cgccctgggc aacaacagct catttcacca ccggatcaac atctacgaga tcatcaagcc    840
cgccaccgcc aacagcaagt tccccgtgac ccggctgctg gacacccggc tggtcaacca    900
gaacgccagc agatgggaga gcttcgacgt gaccctgcc gtgatgagat ggaccgccca     960
gggccacgcc aaccacggct tgtggtgga agtggcccac ctggaagaga agcagggcgt    1020
gtccaagcgg cacgtgcgga tcagcagaag cctgcaccag gacgagcaca gctggtccca   1080
gatccggccc ctgctggtca ccttcggcca cgatggcaag ggccaccccc tgcacaagag   1140
agagaagcgg caggccaagc acaagcagcg gaagcggctg aagtccagct gcaagcggca   1200 cccctgtac gtggacttca gcgacgtggg ctggaacgac tggatcgtgg ccctcccgg    1260 ctaccacgcc ttctactgcc acggcgagtg ccccttcccc ctggccgacc acctgaacag   1320
caccaaccac gccatcgtgc agaccctggt caacagcgtg aactccaaga tccccaaggc   1380
ctgctgcgtg cccaccgagc tgagcgccat cagcatgctg tacctggacg agaacgagaa   1440
ggtggtgctg aagaactacc aggacatggt ggtggaaggc tgtggctgta gatgatacag   1500
caaaattaaa tacataaata tatatataga attctgcaga aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaag cggccgctcg agtc          1674
```

<210> SEQ ID NO 30
<211> LENGTH: 1661
<212> TYPE: DNA
<213> ORGANISM: Artificial Sequence
<220> FEATURE:
<223> OTHER INFORMATION: Sequence of uncapped hBmp2 mRNA when the vector
      is linearized with NotI

<400> SEQUENCE: 30

```
gagaataact tgcgcacccc actttgcgcc ggtgcctttg ccccagcgga gcctgcttcg     60
ccatctccga gccccaccgc ccctccactc ctcggccttg cccgacactg agacgctgtt    120
cccagcgtga aagagagac tgcgcggccg gcacccggga aaggaggag gcaaagaaaa      180 ggaacggaca ttcggtcctt gcgccaggtc ctttgaccag agttttttcca tgtggacgct   240 cttcaatgg acgtgtcccc gcgtgcttct tagacggact gcggtctcct aaaggtcggc    300
caccatggtc gccggcacca gatgtctgct ggctctgctg ctgcctcagg tgctgctggg   360
cggagctgcc ggactggtgc ctgagctggg cagaagaaag ttcgccgctg ccagctctgg   420
cagacccagc agccagcctt ccgacgaggt gctgagcgag ttcgagctgc ggctgctgag   480
catgttcggc ctgaagcaga ggcccacccc cagcagagat gccgtggtgc cccctacat    540 gctggacctg tacagacggc acagcggaca gcctggaagc cctgcccctg accacagact   600
ggaaagagcc gccagccggg ccaacaccgt gcggagcttt caccacgagg aaagcctgga   660
agaactgccc gagacaagcg gcaagaccac ccggcggttc tttttcaacc tgtcctccat   720
ccccaccgaa gagttcatca ccagcgccga actccaggtg ttccgcgagc agatgcagga   780
cgccctgggc aacaacagct catttcacca ccggatcaac atctacgaga tcatcaagcc   840
cgccaccgcc aacagcaagt tccccgtgac ccggctgctg gacacccggc tggtcaacca   900
gaacgccagc agatgggaga gcttcgacgt gaccctgcc gtgatgagat ggaccgccca    960
gggccacgcc aaccacggct tgtggtgga agtggcccac ctggaagaga agcagggcgt   1020
gtccaagcgg cacgtgcgga tcagcagaag cctgcaccag gacgagcaca gctggtccca  1080
gatccggccc ctgctggtca ccttcggcca cgatggcaag ggccaccccc tgcacaagag  1140
```

```
agagaagcgg caggccaagc acaagcagcg gaagcggctg aagtccagct gcaagcggca    1200
ccccctgtac gtggacttca gcgacgtggg ctggaacgac tggatcgtgg ccctcccgg     1260 ctaccacgcc ttctactgcc acggcgagtg ccccttcccc ctggccgacc acctgaacag    1320
caccaaccac gccatcgtgc agaccctggt caacagcgtg aactccaaga tccccaaggc    1380
ctgctgcgtg cccaccgagc tgagcgccat cagcatgctg tacctggacg agaacgagaa    1440
ggtggtgctg aagaactacc aggacatggt ggtggaaggc tgtggctgta gatgatacag    1500
caaaattaaa tacataaata tatatataga attctgcaga aaaaaaaaa aaaaaaaaa     1560 aaaaaaaaaa aaaaaaaaaa aaaaaaaaa aaaaaaaaa aaaaaaaaa aaaaaaaaa       1620 aaaaaaaaaa aaaaaaaaaa aaaaaaaaa aaaaaaaag c                         1661
```

<210> SEQ ID NO 31
<211> LENGTH: 1489
<212> TYPE: DNA
<213> ORGANISM: Artificial Sequence
<220> FEATURE:
<223> OTHER INFORMATION: Sequence of uncapped hBmp7 mRNA when the vector
      is linearized with NotI

<400> SEQUENCE: 31

```
gagacccaag ctggctagcg tttaaactta agcttggtac cgagctcgga tccgccacca    60
tgcacgtacg cagtcttagg gctgctgccc cacacagctt tgtggccctg tgggcacccc    120
tctttctgct taggtctgct cttgccgact tttcactgga caacgaggtc cattcctcat    180
ttatccaccg tcgactgaga agccaagaga ggcgggaaat gcagcgcgag attttgtcta    240
tcctgggatt gccccataga cctcgtcccc atctccaagg gaaacacaac tctgctccca    300
tgttcatgct ggatctgtac aatgccatgg cagtggagga aggtggtggc ccaggaggac    360
agggcttctc ctatccgtac aaggccgtct tttccaccca aggtccaccg ttggcgagtc    420
tccaggattc ccatttcctg accgatgcgg acatggtgat gtcattcgtg aacctggtgg    480
aacacgacaa agagttcttt caccccaggt atcaccacag agagttccgc ttcgacttga    540
gtaaaatccc tgagggagaa gccgttactg ccgccgagtt tcgcatttac aaggactaca    600
ttcgggagag gttcgataac gaaaccttcc ggatatccgt gtatcaggtg ctgcaagagc    660
atctggggag agagtccgat ctcttcctcc tggacagtag gacactgtgg gcgtctgagg    720
aaggctggct tgtgttcgac ataactgcca cgagcaatca ctgggttgta aacccaaggc    780
ataacctggg gcttcagctg tctgtcgaga cactggatgg gcagagcatc aatcccaaac    840
tggctgggtt gatcggacgc catggtccac agaacaaaca gcctttcatg gtagctttct    900
ttaaggccac agaagtgcac tttcggagta ttcggagcac tggcagcaaa cagagaagcc    960
agaatagatc caagacccct aagaatcagg aagccctgcg gatggcaaat gtggcggaga    1020
atagcagctc agatcagaga caggcttgca agaagcatga actgtatgtg tcttttcgag    1080
atctcggatg gcaggactgg attatcgcac cagagggcta tgctgcctac tattgcgaag    1140
gcgagtgcgc atttcctctg aacagctaca tgaacgcaac caatcatgcc attgtccaaa    1200
cactcgttca cttcatcaat ccggaaactg tgcctaaacc ctgttgtgca cctacgcagc    1260
tgaacgctat atctgttctg tactttgacg attcatccaa cgtcatcctc aagaagtacc    1320
gcaatatggt tgtccgagca tgcggctgtc actgagaatt cctgcagaaa aaaaaaaaa    1380 aaaaaaaaaa aaaaaaaaa aaaaaaaaa aaaaaaaaa aaaaaaaaa aaaaaaaaa        1440 aaaaaaaaaa aaaaaaaaa aaaaaaaaa aaaaaaagc                            1489
```

<210> SEQ ID NO 32
<211> LENGTH: 20
<212> TYPE: DNA
<213> ORGANISM: Artificial Sequence
<220> FEATURE:
<223> OTHER INFORMATION: forward mouse primer

<400> SEQUENCE: 32
gtgccctgac tgaggctgtc                                         20

<210> SEQ ID NO 33
<211> LENGTH: 21
<212> TYPE: DNA
<213> ORGANISM: Artificial Sequence
<220> FEATURE:
<223> OTHER INFORMATION: reverse mouse primer

<400> SEQUENCE: 33
ggatcatcgt gtcctgctca c                                       21

<210> SEQ ID NO 34
<211> LENGTH: 20
<212> TYPE: DNA
<213> ORGANISM: Artificial Sequence
<220> FEATURE:
<223> OTHER INFORMATION: forward mouse primer

<400> SEQUENCE: 34
ccgggagcag tgtgagctta                                         20

<210> SEQ ID NO 35
<211> LENGTH: 21
<212> TYPE: DNA
<213> ORGANISM: Artificial Sequence
<220> FEATURE:
<223> OTHER INFORMATION: reverse mouse primer

<400> SEQUENCE: 35
tagatgcgtt tgtaggcggt c                                       21

<210> SEQ ID NO 36
<211> LENGTH: 20
<212> TYPE: DNA
<213> ORGANISM: Artificial Sequence
<220> FEATURE:
<223> OTHER INFORMATION: forward mouse primer

<400> SEQUENCE: 36
gcacagtcaa ggccgagaat                                         20

<210> SEQ ID NO 37
<211> LENGTH: 20
<212> TYPE: DNA
<213> ORGANISM: Artificial Sequence
<220> FEATURE:
<223> OTHER INFORMATION: reverse mouse primer

<400> SEQUENCE: 37
gccttctcca tggtggtgaa                                         20

<210> SEQ ID NO 38
<211> LENGTH: 21
<212> TYPE: DNA
<213> ORGANISM: Artificial Sequence
<220> FEATURE:

```
<223> OTHER INFORMATION: forward rat primer

<400> SEQUENCE: 38
ccgtgtcagc aaaacttctt t                                              21

<210> SEQ ID NO 39
<211> LENGTH: 19
<212> TYPE: DNA
<213> ORGANISM: Artificial Sequence
<220> FEATURE:
<223> OTHER INFORMATION: reverse rat primer

<400> SEQUENCE: 39
gctcacgtcg ctcatcttg                                                 19

<210> SEQ ID NO 40
<211> LENGTH: 21
<212> TYPE: DNA
<213> ORGANISM: Artificial Sequence
<220> FEATURE:
<223> OTHER INFORMATION: forward rat primer

<400> SEQUENCE: 40
cccaactgtc aggagctaga g                                              21

<210> SEQ ID NO 41
<211> LENGTH: 18
<212> TYPE: DNA
<213> ORGANISM: Artificial Sequence
<220> FEATURE:
<223> OTHER INFORMATION: reverse rat primer

<400> SEQUENCE: 41
gatgtggcgg ctgtgaat                                                  18

<210> SEQ ID NO 42
<211> LENGTH: 18
<212> TYPE: DNA
<213> ORGANISM: Artificial Sequence
<220> FEATURE:
<223> OTHER INFORMATION: forward rat primer

<400> SEQUENCE: 42
acggcagctt cagctttg                                                  18

<210> SEQ ID NO 43
<211> LENGTH: 20
<212> TYPE: DNA
<213> ORGANISM: Artificial Sequence
<220> FEATURE:
<223> OTHER INFORMATION: reverse rat primer

<400> SEQUENCE: 43
gaggcagaga gagggaacag                                                20

<210> SEQ ID NO 44
<211> LENGTH: 19
<212> TYPE: DNA
<213> ORGANISM: Artificial Sequence
<220> FEATURE:
<223> OTHER INFORMATION: forward rat primer

<400> SEQUENCE: 44
tggaacactg ggtcccata                                                 19
```

```
<210> SEQ ID NO 45
<211> LENGTH: 19
<212> TYPE: DNA
<213> ORGANISM: Artificial Sequence
<220> FEATURE:
<223> OTHER INFORMATION: reverse rat primer

<400> SEQUENCE: 45
gacctggtct tccctccaa                                                    19

<210> SEQ ID NO 46
<211> LENGTH: 18
<212> TYPE: DNA
<213> ORGANISM: Artificial Sequence
<220> FEATURE:
<223> OTHER INFORMATION: forward rat primer

<400> SEQUENCE: 46
ctgatgagca gggcgagt                                                     18

<210> SEQ ID NO 47
<211> LENGTH: 22
<212> TYPE: DNA
<213> ORGANISM: Artificial Sequence
<220> FEATURE:
<223> OTHER INFORMATION: reverse rat primer

<400> SEQUENCE: 47
tccgagaagt tcttaagcct ca                                                22
```